United States Patent
Roberts et al.

(10) Patent No.: US 9,682,966 B2
(45) Date of Patent: Jun. 20, 2017

(54) KAPPA OPIOID LIGANDS

(71) Applicant: The Scripps Research Institute, La Jolla, CA (US)

(72) Inventors: Edward Roberts, Fallbrook, CA (US); Miguel A. Guerrero, San Diego, CA (US); Mariangela Urbano, Del Mar, CA (US); Hugh Rosen, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 14/421,932

(22) PCT Filed: Aug. 16, 2013

(86) PCT No.: PCT/US2013/055313
§ 371 (c)(1),
(2) Date: Feb. 16, 2015

(87) PCT Pub. No.: WO2014/028829
PCT Pub. Date: Feb. 20, 2014

(65) Prior Publication Data
US 2015/0210673 A1 Jul. 30, 2015

Related U.S. Application Data

(60) Provisional application No. 61/683,861, filed on Aug. 16, 2012.

(51) Int. Cl.
| | |
|---|---|
| A61P 25/04 | (2006.01) |
| A61K 31/4545 | (2006.01) |
| A61P 37/02 | (2006.01) |
| A61K 31/435 | (2006.01) |
| A61P 25/28 | (2006.01) |
| C07D 405/14 | (2006.01) |
| C07D 413/14 | (2006.01) |
| C07D 401/04 | (2006.01) |
| C07D 211/58 | (2006.01) |

(52) U.S. Cl.
CPC .......... *C07D 405/14* (2013.01); *C07D 211/58* (2013.01); *C07D 401/04* (2013.01); *C07D 413/14* (2013.01)

(58) Field of Classification Search
CPC .. C07D 413/14; C07D 405/14; C07D 211/58; C07D 401/04
USPC ........................................................ 546/152
See application file for complete search history.

(56) References Cited

U.S. PATENT DOCUMENTS

| | | | |
|---|---|---|---|
| 5,565,408 A | * | 10/1996 | Hagen .................... A01N 25/32 504/104 |
| 6,284,769 B1 | | 9/2001 | Dunn et al. |
| 6,323,212 B1 | | 11/2001 | Nagase et al. |
| 6,562,827 B1 | | 5/2003 | Lubisch et al. |
| 7,479,559 B2 | | 1/2009 | Brodney et al. |
| 2008/0275048 A1 | | 11/2008 | Frost et al. |
| 2011/0118261 A1 | | 5/2011 | Allen et al. |

FOREIGN PATENT DOCUMENTS

| | | | |
|---|---|---|---|
| WO | WO2011025799 | * | 3/2011 |
| WO | WO-2012/076674 A1 | | 6/2012 |
| WO | WO-2014/028829 A1 | | 2/2014 |

OTHER PUBLICATIONS

Chemical Abstracts STN Database Record for RN 412355-81-8, entered on May 8, 2002.*
Chemical Abstracts STN Database Record for RN 1284380-23-9, entered on Apr. 24, 2011.*
McCurdy; Burgers Medicinal Chemistry, Drug Discovery and Development, 7th ed., John Wiley and Sons, New York, 2010, 569-735.*
Chemical Abstracts STN Database Record for RN 1308001-82-2, entered on Jun. 9, 2011.*
Chemical Abstracts STN Database Record for RN 1307960-70-8, entered on Jun. 9, 2011.*
Chemical Abstracts STN Database Record for RN 1307736-52-2, entered on Jun. 8, 2011.*
Chemical Abstracts STN Database Record for RN 1378971-21-1, entered on Jun. 15, 2012.*
Chemical Abstracts STN Database Record for RN 1378517-29-3, entered on Jun. 14, 2012.*
Chemical Abstracts STN Database Record for RN 1308001-85-5, entered on Jun. 9, 2011.*
Chemical Abstracts STN Database Record for RN 1304879-64-8, entered on Jun. 3, 2011.*
Chemical Abstracts STN Database Record for RN 1157007-46-9, entered on Jun. 14, 2009.*Chemical Abstracts STN Database Record for RN 1154666-59-7, entered on Jun. 9, 2009.*
"International Application Serial No. PCT/US2013/055313, International Search Report mailed Jan. 16, 2014", 4 pgs.
"International Application Serial No. PCT/US2013/055313, Written Opinion mailed Jan. 16, 2014", 20 pgs.

* cited by examiner

Primary Examiner — Noble Jarrell
Assistant Examiner — Daniel Carcanague
(74) Attorney, Agent, or Firm — Seed IP Law Group LLP

(57) ABSTRACT

The invention provides novel ligands of Kappa (κ) opioid receptors, such as can be used to modulate a Kappa opioid receptor. Methods of synthesis and methods of use are also provided. Compounds of the invention can be used therapeutically in the treatment of dissociative disorders or pain, or to provide neuroprotection, or to induce diuresis, or to modulate the immune system, or for treatment of one or more of an affective disorders comprising depression or stress/anxiety; an addictive disorder; alcoholism, epilepsy; a cognition deficiency; schizophrenia; Alzheimer's disease; or pain.

25 Claims, No Drawings

KAPPA OPIOID LIGANDS

CROSS-REFERENCE TO RELATED APPLICATIONS

This application is a U.S. national stage application filed under 35 U.S.C. §371 from International Application Serial No. PCT/US2013/055313, which was filed Aug. 16, 2013, and published as WO 2014/028829 on Feb. 20, 2014, and which claims the priority of U.S. provisional application Ser. No. 61/683,861, filed Aug. 16, 2012, which applications and publication are incorporated by reference as if reproduced herein and made a part hereof in their entirety, and the benefit of priority of each of which is claimed herein.

STATEMENT OF GOVERNMENT SUPPORT

This invention was made with government support under grant number MH084512-02, awarded by the National Institutes of Health. The U.S. government has certain rights in the invention.

BACKGROUND

The kappa-opioid receptor (KOR) is a member of the opioid receptor family which binds the opioid peptide dynorphin as the primary endogenous ligand. KOR has a wide, yet distinct distribution in the brain, spinal cord, and in pain neurons. Recently, there have been significant advances in understanding the role of KOR in controlling cognition and emotion in addition to insights into its involvement in neurological diseases such as epilepsy and neuropathic pain. These pathologies share the common feature of disruption of the induction of neuroplasticity. While this is not a particularly novel idea in epilepsy, an emerging scheme in the field of psychiatric disorders is that diseases such as addition and depression also stem from disruption in normal synaptic physiology and aberrant neuroplasticity that ultimately lead to maladaptive learning. Kappa opioid receptors have recently been investigated for their therapeutic potential in the treatment of addiction (Hasebe K, Kawai K, Suzuki T, Kawamura K, Tanaka T, Narita M, Nagase H, Suzuki T (2004) "Possible pharmacotherapy of the opioid kappa receptor agonist for drug dependence" *Annals of the New York Academy of Sciences* 1025: 404-13), and evidence points towards dynorphin to be one of the body's natural addiction control mechanism (Frankel P S, Alburges M E, Bush L, Hanson G R, Kish S J (2008) "Striatal and ventral pallidum dynorphin concentrations are markedly increased in human chronic cocaine users" *Neuropharmacology* 55 (1): 41-6).

In experimental "addiction" models the kappa-opioid receptor has also been shown to influence stress-induced relapse to drug seeking behavior. For the drug dependent individual, risk of relapse is a major obstacle to becoming drug free. Recent reports demonstrated that KOR are required for stress-induced reinstatement of cocaine seeking (Beardsley P M, Howard J L, Shelton K L, Carroll F I (2005) "Differential effects of the novel kappa opioid receptor antagonist, JDTic, on reinstatement of cocaine-seeking induced by footshock stressors vs cocaine primes and its antidepressant-like effects in rats" *Psychopharmacology* (Berl.) 183 (1): 118-26; Redila V A, Chavkin C (2008). "Stress-induced reinstatement of cocaine seeking is mediated by the kappa opioid system" *Psychopharmacology* 200 (1): 59-70; Blum K, Braverman E R, Holder J M, Lubar J F, Monastra V J, Miller D, Lubar J O, Chen T J, Comings D E (2000) "Reward deficiency syndrome: a biogenetic model for the diagnosis and treatment of impulsive, addictive, and compulsive behaviors" *Journal ofpsychoactive drugs* 32 Suppl: i-iv, 1-112). It has also been reported that the dynorphin-Kappa opioid system is critical for stress-induced drug seeking. In animal models, stress has been demonstrated to potentiate cocaine reward behavior in a kappa opioid-dependent manner (McLaughlin J P, Marton-Popovici M, Chavkin C. (2003) "Kappa opioid receptor antagonism and prodynophin gene disruption block stress-induced behavioral responses" *The Journal of Neuroscience* 23 (13): 5674-83; Mash, Deborah C. (2006) "Social defeat stress-induced behavioral responses are mediated by the endogenous kappa opioid system" *Neuropsychopharmacology* 31 (4): 787-94). These effects are likely caused by stress-induced drug craving that requires activation of the dynorphin-KOR system. Although seemingly paradoxical, it is well known that drug taking results in a change from homeostasis to allostasis.

It has been suggested that withdrawal-induced dysphoria or stress-induced dysphoria may act as a driving force by which the individual seeks alleviation via drug taking. The rewarding properties of the drug are altered, and it is clear kappa-opioid activation following stress increase its rewarding properties and cause potentiation of reward behavior, or reinstatement to drug seeking. The stress-induced activation of kappa-opioid receptors is likely due to multiple signaling mechanisms. The kappa-opioid receptors have marked effects on all types of addiction including alcohol and opiate abuse. Cocaine addiction, as well as addiction to alcohol or other drug, is a world wide problem that has serious social, mental, and physical consequences. While various forms of prevention and/or treatment of addiction have been attempted, there remains a need for an improvement. For example, small molecules have been used as drugs to decrease the physical and/or mental conditions associated with addiction.

It is now thought that dysphoric elements of stress contributed to the development of anxiety states and clinical depression. There is recent evidence to suggest that dysphoric components of stress are encoded by the dynorphin-KOR system (Land B B, Bruchas M R, Lemos J C, Xu M, Melief E J, Chavkin C (2008) "The dysphoric component of stress is encoded by activation of the dynorphin kappa-opioid system" *J Neurosci* 28(2):407-414). It has been demonstrated that stress decreases BDNF expression, which in turn predisposes the individual to depressive mood. Acute pretreatment with high doses of norBNI has been shown to increase BDNF mRNA expression in the area of hippocampus and the amygdala (Zhang H, Shi Y G, Woods J H, Watson S J, Ko M C (2007) "Central kappa-opioid receptor mediated antidepressant-like effects of nor Binaltorphimine: behavioral and BDNF mRNA expression studies" *Eur J Pharmacol* 570(1-3):89-96; Duman R S, Monteggia L M (2006) "A neurotrophic model for stress-related mood disorders" *Biol Psychiatry* 59(12):1116-1127).

Several behavioral studies using KOR agonists/antagonists as well as knockout animals have demonstrated a potential role for the dynorphin-KOR system in analgesia of neuropathic pain. (Gaveriaux-Ruff C, Kieffer B L (2002) "Opioid receptor genes inactivated in mice: the highlights" *Neuropeptides* 36 (2-3): 62-71).

There is a body of evidence to suggest that dynorphin peptide and message expression is up-regulated in both epileptic humans and animal models of epilepsy, suggesting that the dynorphin-KOR system play a significant role in the disease. (Bausch S B, Esteb T M, Terman G W, Chavkin C (1998) "Administered and endogenously released kappa opioids decrease pilocarpine-induced seizures and seizure-induced histopathology" *J Pharmacol Exp Ther* 284(3): 1147-1155; de Lanerolle N C, Williamson A, Meredith C et al (1997) "Dynorphin and the kappa 1 ligand [3H] U69,593 binding in the human epileptogenic hippocampus" *Epilepsy Res* 28(3): 189-205; Loacker S, Sayyah M, Wittmann W, Herzog H, Schwarzer C (2007) "Endogenous dynorphin in epileptogenesis and epilepsy: anticonvulsant net effect via kappa opioid receptors" *Brain* 130(pt 4): 1017-1028; Houser C R, Miyashiro J E, Swartz B E, Walsh G O, Rich J R, Delgado-Escueta A V (1990) "Altered patterns of dynorphin immunoreactivity suggest mossy fiber reorganization in human hippocampal epilepsy" *J Neurosci* 10(1):267-282; De Sarro G B, De Sarro A (1993) "Anticonvulsant properties of non-competitive antagonists of the N-methyl-D-aspartate receptor in genetically epilepsy-prone rats: comparison with CPPene" *Neuropharmacology* 32(1):51-58).

It has been suggested that the dynorphin-KOR system is involved in the learning process. A negative correlation between the level of spatial learning and the level of dinorphin immunoreactivity in the hippocampal formation has been demonstrated (Jiang H K, Owyang V V, Hong J S, Gallagher M (1989) "Elevated dynorphin in the hippocampal formation of aged rats: relation to cognitive impairment on a spatial learning task" Proc *Natl Acad Sci USA* 86(8): 2948-2951). In humans, the brain of Alzheimer disease patients have significant increase in dynorphin expression compared to age matched controls (Mathieu-Kia A M, Fan L Q, Kreek M J, Simon E J, Hiller J M (2001) "Mu-, delta- and kappa-opioid receptor populations are differentially altered in distinct areas of postmortem brains of Alzheimer's disease patients" *Brain Res* 893(1-2): 121-134).

SUMMARY

The present invention is directed in various embodiments to novel ligands of kappa opioid receptors, i.e., modulators of the class of opioid receptors termed Kappa (κ) receptors. In various embodiments, the invention provides a compound of formula (I)

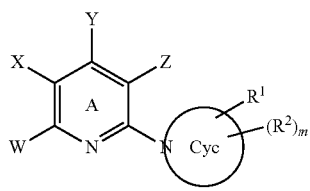

(I)

wherein
the ring designated A can further comprise an additional nitrogen atom in any position that bears any of W, X, Y, or Z, provided that the respective group W, X, Y, or Z is absent from that position;

W is H, (C1-C6)alkyl, (C1-C6)haloalkyl, hydroxy(C1-C6)alkyl, (C3-C9)cycloalkyl, or halo;

X is H, halo, nitro, (C1-C6)alkyl, (C1-C6)haloalkyl, hydroxy(C1-C6)alkyl, (C3-C9)cycloalkyl, $NR^aR^b$, $N(R^a)C(=O)(C1-C6)alkyl$, $CO_2R$, or heteroaryl;

Y is H, halo, (C1-C6)alkyl, (C3-C9)cycloalkyl, or halo;

Z is halo, hydroxy, $CO_2R$, $C(=O)NR_2$, CN, heteroaryl($C_0-C_6$)alkyl, hydroxy(C1-C6)alkyl, HC(=O), HC(=O), (C1-C6)C(=O), or CR(=NOR);

wherein each independently selected R is H, (C1-C6)alkyl, (C3-C9)cycloalkyl, (C6-C10)aryl, or (C6-C10)aryl(C1-C6)alkyl;

or, any adjacent pair of W, X, and Y, can together with the atoms to which they are bonded form a fused cycloalkyl, heterocyclyl, or aryl, or heteroaryl, any of which can be mono- or independently multi-substituted with (C1-C6)alkyl, (C3-C9)cycloalkyl, halo, nitro, $NR^aR^b$, $N(R^a)C(=O)(C1-C6)alkyl$, $CO_2R$, or heteroaryl;

wherein any alkyl, cycloalkyl, aryl, or heteroaryl of W, X, Y, or Z, can be unsubstituted or can be mono- or independently multi-substituted with (C1-C6)alkyl, (C3-C9)cycloalkyl, halo, nitro, $NR^aR^b$, $N(R^a)C(=O)(C1-C6)alkyl$, $CO_2R$, or heteroaryl;

the ring system Cyc, comprising the nitrogen atom, comprises a mono-, bi-, or tri-cyclic heterocyclyl bonded to ring A via the nitrogen atom, wherein Cyc comprises a 4, 5, 6, 7, or 8 membered ring, optionally bridged with one or two bridges independently comprising 0, 1, or 2 carbon atoms, the ring system Cyc optionally containing 1 or 2 additional heteroatoms selected from NR, O, or $S(O)_q$ wherein q=0, 1, or 2; wherein $R^1$, and optionally, m independently selected $R^2$, are bonded to the ring system Cyc, m=0, 1, or 2;

$R^1$ is $(CH_2)_nNR^aR^b$, wherein $R^a$ and $R^b$ are each independently H, alkyl, cycloalkyl, cycloalkylalkyl, heterocyclyl, or heterocyclylalkyl, wherein any alkyl, cycloalkyl, cycloalkylalkyl, heterocyclyl, or heterocyclylalkyl, is substituted with 0, 1, 2, 3, or 4 independently selected J, and wherein any heterocyclyl or cycloalkyl is mono-, bi-, or tri-cyclic; or $R^a$ and $R^b$ together with the nitrogen atom to which they are bonded form a heterocyclyl ring substituted with 0, 1, 2, 3, or 4 independently selected J, wherein n=0, 1, or 2;

or $R^1$ is $(CH_2)_{p1}NR^a(CH_2)_{p2}$ bonded to two carbon atoms of Cyc to form a 5-, 6-, or 7-membered heterocyclyl substituted with 0, 1, 2, 3, or 4 independently selected J, p1 and p2 are independently 0, 1, or 2, provided that p1+p2 is no less than 2;

$R^2$ is (C1-C6)alkyl, hydroxy(C1-C6)alkyl, OR, $CO_2R$, or halo, wherein m=0, 1, or 2;

J is independently at each occurrence OR, (C1-C6)alkyl, hydroxy(C1-C6)alkyl, (C3-C9)cycloalkyl, $CO_2R$, or halo;

or any pharmaceutically acceptable salt thereof.

In various embodiments, the invention provides a pharmaceutical composition, comprising a compound of the invention and a pharmaceutically acceptable excipient.

In various embodiments, the invention provides a method of modulating a Kappa opioid receptor, comprising contacting the receptor with an effective amount or concentration of a compound of formula (I) of the invention. The Kappa opioid receptor can be disposed within living human tissue, such as in a patient suffering from a dissociative disorder, or from pain.

In various embodiments, the invention provides a method of treatment of a dissociative disorder or pain in a patient in need thereof, comprising administering to the patient an effective amount or concentration of a compound of formula (I) of the invention at a frequency and for a duration to provide a beneficial effect to the patient.

In various embodiments, the invention provides a method of providing neuroprotection to a patient comprising administering to the patient an effective amount or concentration of a compound of formula (I) of the invention at a frequency and for a duration to provide a beneficial effect to the patient.

In various embodiments, the invention provides a method of modulating the immune system in a patient, comprising administering to the patient an effective amount or concentration of a compound of formula (I) of the invention at a frequency and for a duration to provide a beneficial effect to the patient.

In various embodiments, the invention provides a method of inducing diuresis in a patient, comprising administering to the patient an effective amount or concentration of a compound of formula (I) of the invention at a frequency and for a duration to provide a beneficial effect to the patient.

DETAILED DESCRIPTION

Definitions

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

All average molecular weights of polymers are weight-average molecular weights, unless otherwise specified.

As used herein, "individual" (as in the subject of the treatment) or "patient" means both mammals and non-mammals. Mammals include, for example, humans; non-human primates, e.g. apes and monkeys; and non-primates, e.g. dogs, cats, cattle, horses, sheep, and goats. Non-mammals include, for example, fish and birds.

The term "disease" or "disorder" or "malcondition" are used interchangeably, and are used to refer to diseases or conditions wherein a kappa (κ) opioid receptor plays a role in the biochemical mechanisms involved in the disease or malcondition or symptom(s) thereof such that a therapeutically beneficial effect can be achieved by acting on a kappa opioid receptor. "Acting on" a kappa opioid receptor, or "modulating" a kappa opioid receptor, can include binding to a kappa opioid receptor and/or inhibiting the bioactivity of a kappa opioid receptor and/or allosterically regulating the bioactivity of a kappa opioid receptor in vivo.

The expression "effective amount", when used to describe therapy to an individual suffering from a disorder, refers to the amount of a compound of the invention that is effective to inhibit or otherwise act on a kappa opioid receptor in the individual's tissues wherein a kappa opioid receptor involved in the disorder is active, wherein such inhibition or other action occurs to an extent sufficient to produce a beneficial therapeutic effect.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result.

A therapeutically effective amount is also one in which any toxic or detrimental effects of compounds of the invention are outweighed by the therapeutically beneficial effects.

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

An "analog" of a chemical structure, as the term is used herein, refers to a chemical structure that preserves substantial similarity with the parent structure, although it may not be readily derived synthetically from the parent structure. A related chemical structure that is readily derived synthetically from a parent chemical structure is referred to as a "derivative."

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

As used herein, the terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

A "small molecule" refers to an organic compound, including an organometallic compound, of a molecular weight less than about 2 kDa, that is not a polynucleotide, a polypeptide, a polysaccharide, or a synthetic polymer composed of a plurality of repeating units.

As to any of the groups described herein, which contain one or more substituents, it is understood that such groups do not contain any substitution or substitution patterns which are sterically impractical and/or synthetically non-feasible. In addition, the compounds of this disclosed subject matter include all stereochemical isomers arising from the substitution of these compounds.

In various embodiments, the compound or set of compounds, such as are among the inventive compounds or are used in the inventive methods, can be any one of any of the combinations and/or sub-combinations of the above-listed embodiments.

When a group, e.g., an "alkyl" group, is referred to without any limitation on the number of atoms in the group, it is understood that the claim is definite and limited with respect the size of the alkyl group, both by definition; i.e., the size (the number of carbon atoms) possessed by a group such as an alkyl group is a finite number, less than the total number of carbon atoms in the universe and bounded by the understanding of the person of ordinary skill as to the size of the group as being reasonable for a molecular entity; and by functionality, i.e., the size of the group such as the alkyl group is bounded by the functional properties the group bestows on a molecule containing the group such as solubility in aqueous or organic liquid media. Therefore, a claim reciting an "alkyl" or other chemical group or moiety is definite and bounded, as the number of atoms in the group cannot be infinite.

The inclusion of an isotopic form of one or more atoms in a molecule that is different from the naturally occurring isotopic distribution of the atom in nature is referred to as an "isotopically labeled form" of the molecule. All isotopic forms of atoms are included as options in the composition of any molecule, unless a specific isotopic form of an atom is indicated. For example, any hydrogen atom or set thereof in a molecule can be any of the isotopic forms of hydrogen, i.e., protium ($^1$H), deuterium ($^2$H), or tritium ($^3$H) in any combination. Similarly, any carbon atom or set thereof in a molecule can be any of the isotopic form of carbons, such as $^{11}$C, $^{12}$C, $^{13}$C, or $^{14}$C, or any nitrogen atom or set thereof in a molecule can be any of the isotopic forms of nitrogen, such as $^{13}$N, $^{14}$N, or $^{15}$N. A molecule can include any combination of isotopic forms in the component atoms making up the molecule, the isotopic form of every atom forming the molecule being independently selected. In a multi-molecular sample of a compound, not every individual molecule necessarily has the same isotopic composition. For example, a sample of a compound can include molecules containing various different isotopic compositions, such as in a tritium or $^{14}$C radiolabeled sample where only some fraction of the set of molecules making up the macroscopic sample contains a radioactive atom. It is also understood that many elements that are not artificially isotopically enriched themselves are mixtures of naturally occurring isotopic forms, such as $^{14}$N and $^{15}$N, $^{32}$S and $^{34}$S, and so forth. A molecule as recited herein is defined as including isotopic forms of all its constituent elements at each position in the molecule. As is well known in the art, isotopically labeled compounds can be prepared by the usual methods of chemical synthesis, except substituting an isotopically labeled precursor molecule. The isotopes, radiolabeled or stable, can be obtained by any method known in the art, such as generation by neutron absorption of a precursor nuclide in a nuclear reactor, by cyclotron reactions, or by isotopic separation such as by mass spectrometry. The isotopic forms are incorporated into precursors as required for use in any particular synthetic route. For example, $^{14}$C and $^3$H can be prepared using neutrons generated in a nuclear reactor. Following nuclear transformation, $^{14}$C and $^3$H are incorporated into precursor molecules, followed by further elaboration as needed.

The term "amino protecting group" or "N-protected" as used herein refers to those groups intended to protect an amino group against undesirable reactions during synthetic procedures and which can later be removed to reveal the amine. Commonly used amino protecting groups are disclosed in Protective Groups in Organic Synthesis, Greene, T. W.; Wuts, P. G. M., John Wiley & Sons, New York, N.Y., (3rd Edition, 1999). Amino protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxy-carbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4, 5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethyl silylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Amine protecting groups also include cyclic amino protecting groups such as phthaloyl and dithiosuccinimidyl, which incorporate the amino nitrogen into a heterocycle. Typically, amino protecting groups include formyl, acetyl, benzoyl, pivaloyl, t-butylacetyl, phenylsulfonyl, Alloc, Teoc, benzyl, Fmoc, Boc and Cbz. It is well within the skill of the ordinary artisan to select and use the appropriate amino protecting group for the synthetic task at hand.

The term "hydroxyl protecting group" or "O-protected" as used herein refers to those groups intended to protect an OH group against undesirable reactions during synthetic procedures and which can later be removed to reveal the amine. Commonly used hydroxyl protecting groups are disclosed in Protective Groups in Organic Synthesis, Greene, T. W.; Wuts, P. G. M., John Wiley & Sons, New York, N.Y., (3rd Edition, 1999). Hydroxyl protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxy-benzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethyl silylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. It is well within the skill of the ordinary artisan to select and use the appropriate hydroxyl protecting group for the synthetic task at hand.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents J that can be bonded to a substituted carbon (or other) atom include F, Cl, Br, I, OR', OC(O)N(R')$_2$, CN, NO, NO$_2$, ONO$_2$, azido, CF$_3$, OCF$_3$, R', O (oxo), S (thiono), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON (R')$_2$, N(R')SO$_2$R', N(R')SO$_2$N(R')$_2$, N(R')C(O)OR', N(R')C (O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted; for example, wherein R' can be hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or R' can be independently mono- or multi-substituted with J; or wherein two R' groups bonded to a nitrogen atom or to adjacent nitrogen atoms can together with the nitrogen atom or atoms form a heterocyclyl, which can be mono- or independently multi-substituted with J.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group. When a divalent substituent such as S is double-bonded to a carbon atom, the results C(=S) group is termed a "thiocarbonyl" or "thiono" group.

Alternatively, a divalent substituent such as O or S can be connected by two single bonds to two different carbon atoms. For example, 0, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$ wherein n is 1, 2, 3, or more, and each R' is independently selected.

C(O) and S(O)$_2$ groups can also be bound to one or two heteroatoms, such as nitrogen or oxygen, rather than to a carbon atom. For example, when a C(O) group is bound to one carbon and one nitrogen atom, the resulting group is called an "amide" or "carboxamide." When a C(O) group is bound to two nitrogen atoms, the functional group is termed a "urea." When a C(O) is bonded to one oxygen and one nitrogen atom, the resulting group is termed a "carbamate" or "urethane." When a S(O)$_2$ group is bound to one carbon and one nitrogen atom, the resulting unit is termed a "sulfonamide." When a S(O)$_2$ group is bound to two nitrogen atoms, the resulting unit is termed a "sulfamate."

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with alkyl, alkenyl, and alkynyl groups as defined herein.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic.

By "spirocyclic" is meant the class of structures wherein two rings are fused at a single tetrahedral carbon atom, as is well known in the art.

As to any of the groups described herein, which contain one or more substituents, it is understood, of course, that such groups do not contain any substitution or substitution patterns which are sterically impractical and/or synthetically non-feasible. In addition, the compounds of this disclosed subject matter include all stereochemical isomers arising from the substitution of these compounds.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed above, for example, amino, hydroxy, cyano, carboxy, nitro, thio, alkoxy, and halogen groups.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The terms "carbocyclic," "carbocyclyl," and "carbocycle" denote a ring structure wherein the atoms of the ring are carbon, such as a cycloalkyl group or an aryl group. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N−1 substituents wherein N is the size of the carbocyclic ring with, for example, alkyl, alkenyl, alkynyl, amino, aryl, hydroxy, cyano, carboxy, heteroaryl, heterocyclyl, nitro, thio, alkoxy, and halogen groups, or other groups as are listed above. A carbocyclyl ring can be a cycloalkyl ring, a cycloalkenyl ring, or an aryl ring. A carbocyclyl can be monocyclic or polycyclic, and if polycyclic each ring can be independently be a cycloalkyl ring, a cycloalkenyl ring, or an aryl ring.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

Cycloalkenyl groups include cycloalkyl groups having at least one double bond between 2 carbons. Thus for example, cycloalkenyl groups include but are not limited to cyclohexenyl, cyclopentenyl, and cyclohexadienyl groups. Cycloalkenyl groups can have from 3 to about 8-12 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like, provided they include at least one double bond within a ring. Cycloalkenyl groups also include rings that are substituted with straight or branched chain alkyl groups as defined above.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quatemized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$CH$_2$—OH, —CH$_2$—CH$_2$—NH—CH$_3$, —CH$_2$—S—CH$_2$—CH$_3$, —CH$_2$CH$_2$—S(=O)—CH$_3$, and —CH$_2$CH$_2$—O—CH$_2$CH$_2$—O—CH$_3$. Up to two heteroatoms may be consecutive, such as, for example, —CH$_2$—NH—OCH$_3$, or —CH$_2$—CH$_2$—S—S—CH$_3$.

A "cycloheteroalkyl" ring is a cycloalkyl ring containing at least one heteroatom. A cycloheteroalkyl ring can also be termed a "heterocyclyl," described below.

The term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—CH$_3$, —CH=CH—CH$_2$—OH, —CH$_2$—CH=N—OCH$_3$, —CH=CH—N(CH$_3$)—CH$_3$, —CH$_2$—CH=CH—CH$_2$—SH, and and —CH=CH—O—CH$_2$CH$_2$—O—CH$_3$.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

Heterocyclyl groups or the term "heterocyclyl" includes aromatic and non-aromatic ring compounds containing 3 or more ring members, of which, one or more is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group. The phrase "heterocyclyl group" includes fused ring species including those comprising fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed above. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed above.

Heteroaryl groups are aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed above. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo [b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f] azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f] azepine-4-yl, 10,11-dihydro-5H-dibenz[b,f]azepine-5-yl), and the like.

Heterocyclylalkyl groups are alkyl groups as defined above in which a hydrogen or carbon bond of an alkyl group as defined above is replaced with a bond to a heterocyclyl group as defined above. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

Heteroarylalkyl groups are alkyl groups as defined above in which a hydrogen or carbon bond of an alkyl group is replaced with a bond to a heteroaryl group as defined above.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The terms "halo" or "halogen" or "halide" by themselves or as part of another substituent mean, unless otherwise stated, a fluorine, chlorine, bromine, or iodine atom, preferably, fluorine, chlorine, or bromine.

A "haloalkyl" group includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

A "haloalkoxy" group includes mono-halo alkoxy groups, poly-halo alkoxy groups wherein all halo atoms can be the same or different, and per-halo alkoxy groups, wherein all hydrogen atoms are replaced by halogen atoms, such as fluoro. Examples of haloalkoxy include trifluoromethoxy, 1,1-dichloroethoxy, 1,2-dichloroethoxy, 1,3-dibromo-3,3-difluoropropoxy, perfluorobutoxy, and the like.

The term "$(C_x-C_y)$perfluoroalkyl," wherein x<y, means an alkyl group with a minimum of x carbon atoms and a maximum of y carbon atoms, wherein all hydrogen atoms are replaced by fluorine atoms. Preferred is —$(C_1-C_6)$perfluoroalkyl, more preferred is —$(C_1-C_3)$perfluoroalkyl, most preferred is —$CF_3$.

The term "$(C_x-C_y)$perfluoroalkylene," wherein x<y, means an alkyl group with a minimum of x carbon atoms and a maximum of y carbon atoms, wherein all hydrogen atoms are replaced by fluorine atoms. Preferred is —$(C_1-C_6)$perfluoroalkylene, more preferred is —$(C_1-C_3)$perfluoroalkylene, most preferred is —$CF_2$—.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula N(group)$_3$ wherein each group can independently be H or non-H, such as alkyl, aryl, and the like. Amines include but are not limited to R—$NH_2$, for example, alkylamines, arylamines, alkylarylamines; $R_2$NH wherein each R is independently selected, such as dialkylamines, diarylamines, aralkylamines, heterocyclylamines and the like; and $R_3$N wherein each R is independently selected, such as trialkylamines, dialkylarylamines, alkyldiarylamines, triarylamines, and the like. The term "amine" also includes ammonium ions as used herein.

An "amino" group is a substituent of the form —$NH_2$, —NHR, —$NR_2$, —$NR_3^+$, wherein each R is independently selected, and protonated forms of each, except for —$NR_3^+$, which cannot be protonated. Accordingly, any compound substituted with an amino group can be viewed as an amine. An "amino group" within the meaning herein can be a primary, secondary, tertiary or quaternary amino group. An "alkylamino" group includes a monoalkylamino, dialkylamino, and trialkylamino group.

An "ammonium" ion includes the unsubstituted ammonium ion $NH_4^+$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., —C(O)$NR_2$, and —NRC(O)R groups, respectively. Amide groups therefore include but are not limited to primary carboxamide groups (—C(O)$NH_2$) and formamide groups (—NHC(O)H). A "carboxamido" group is a group of the formula C(O)$NR_2$, wherein R can be H, alkyl, aryl, etc.

The term "azido" refers to an $N_3$ group. An "azide" can be an organic azide or can be a salt of the azide ($N_3^-$) anion. The term "nitro" refers to an $NO_2$ group bonded to an organic moiety. The term "nitroso" refers to an NO group bonded to an organic moiety. The term nitrate refers to an $ONO_2$ group bonded to an organic moiety or to a salt of the nitrate ($NO_3^-$) anion.

The term "urethane" ("carbamoyl" or "carbamyl") includes N- and O-urethane groups, i.e., —NRC(O)OR and —OC(O)$NR_2$ groups, respectively.

The term "sulfonamide" (or "sulfonamido") includes S- and N-sulfonamide groups, i.e., —$SO_2NR_2$ and —$NRSO_2R$ groups, respectively. Sulfonamide groups therefore include but are not limited to sulfamoyl groups (—$SO_2NH_2$). An organosulfur structure represented by the formula —S(O)(NR)— is understood to refer to a sulfoximine, wherein both the oxygen and the nitrogen atoms are bonded to the sulfur atom, which is also bonded to two carbon atoms.

The term "amidine" or "amidino" includes groups of the formula —C(NR)$NR_2$. Typically, an amidino group is —C(NH)$NH_2$.

The term "guanidine" or "guanidino" includes groups of the formula —NRC(NR)$NR_2$. Typically, a guanidino group is —NHC(NH)$NH_2$.

Standard abbreviations for chemical groups such as are well known in the art are used; e.g., Me=methyl, Et=ethyl, i-Pr=isopropyl, Bu=butyl, t-Bu=tert-butyl, Ph=phenyl, Bn=benzyl, Ac=acetyl, Bz=benzoyl, Boc=tert-butoxycarbonyl, and the like.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as $NH_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula (I) compounds, for example in their purification by recrystallization. All of these salts may be prepared by conventional means from the corresponding compound according to Formula (I) by reacting, for example, the appropriate acid or base with the compound according to Formula (I). The term "pharmaceutically acceptable salts" refers to nontoxic inorganic or organic acid and/or base addition salts, see, for example, Lit et al., Salt Selection for Basic Drugs (1986), Int J. Pharm., 33, 201-217, incorporated by reference herein.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patients body, such as enzymes, to the active pharmaceutical ingredient. Examples of prodrugs include esters of carboxylic acid groups, which can be hydrolyzed by endogenous esterases as are found in the bloodstream of humans and other mammals. Conventional procedures for the selection and preparation of suitable prodrug derivatives are described, for example, in "Design of Prodrugs", ed. H. Bundgaard, Elsevier, 1985.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

The present invention further embraces isolated compounds of the invention. The expression "isolated compound" refers to a preparation of a compound of the invention, or a mixture of compounds the invention, wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of the invention or a mixture of compounds of the invention, which contains the named compound or mixture of compounds of the invention in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds of the invention and intermediates may be isolated from their reaction mixtures and purified by standard techniques such as filtration, liquid-liquid extraction, solid phase extraction, distillation, recrystallization or chromatography, including flash column chromatography, or HPLC.

Isomerism and Tautomerism in Compounds of the Invention
Tautomerism

Within the present invention it is to be understood that a compound of the formula (I) or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. It is to be understood that the formulae drawings within this specification can represent only one of the possible tautomeric forms. However, it is also to be understood that the invention encompasses any tautomeric form, and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been convenient to show graphically herein. For example, tautomerism may be exhibited by a pyrazolyl group bonded as indicated by the wavy line. While both substituents would be termed a 4-pyrazolyl group, it is evident that a different nitrogen atom bears the hydrogen atom in each structure.

Such tautomerism can also occur with substituted pyrazoles such as 3-methyl, 5-methyl, or 3,5-dimethylpyrazoles, and the like. Another example of tautomerism is amido-imido (lactam-lactim when cyclic) tautomerism, such as is seen in heterocyclic compounds bearing a ring oxygen atom adjacent to a ring nitrogen atom. For example, the equilibrium:

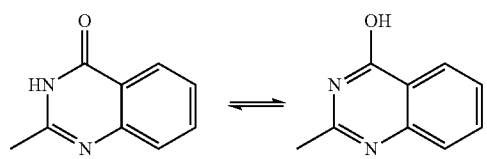

is an example of tautomerism. Accordingly, a structure depicted herein as one tautomer is intended to also include the other tautomer.

Optical Isomerism

It will be understood that when compounds of the present invention contain one or more chiral centers, the compounds may exist in, and may be isolated as pure enantiomeric or diastereomeric forms or as racemic mixtures. The present invention therefore includes any possible enantiomers, diastereomers, racemates or mixtures thereof of the compounds of the invention.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. The priority of substituents is ranked based on atomic weights, a higher atomic weight, as determined by the systematic procedure, having a higher priority ranking. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example in Scheme 14, the Cahn-Ingold-Prelog ranking is A>B>C>D. The lowest ranking atom, D is oriented away from the viewer.

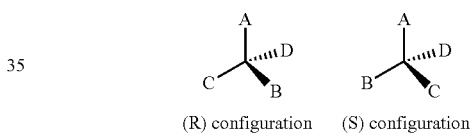

(R) configuration    (S) configuration

The present invention is meant to encompass diastereomers as well as their racemic and resolved, diastereomerically and enantiomerically pure forms and salts thereof. Diastereomeric pairs may be resolved by known separation techniques including normal and reverse phase chromatography, and crystallization. A racemic mixture, or a racemate, is a mixture of two enantiomers.

"Isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Isolated optical isomers may be purified from racemic mixtures by well-known chiral separation techniques. According to one such method, a racemic mixture of a compound of the invention, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

Cis-Trans Isomerism

Compounds comprising double bonds and having non-identical substituents at each end of the double bond can exhibit cis-trans, or Z/E, isomerism. Cis-trans isomerism is present when at each terminus of the double bond there is one hydrogen and one non-hydrogen substituent. Thus, a compound of formula A-CH=CH—B can exist in two isomeric forms, cis:

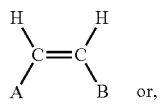

or, trans:

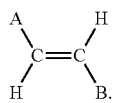

In cases where the four substituents are more complex, this type of isomerism is termed Z/E isomerism. The groups are assigned priority as in the case of optical isomerism, discussed above, and when the two highest priority groups are cis to each other, the double bond is termed a Z double bond; when the two highest priority groups are trans to each other, the double bond is termed an E double bond.

Cis and trans isomerism can also be present in ring systems, where free rotation cannot occur. For example, when both compounds are on the same "side" of the ring, the groups are said to be cis to each other, and when they are on opposite sides, they are said to be trans to each other. For example, 1,4-dimethylcyclohexane can exist in cis and trans forms:

cis:

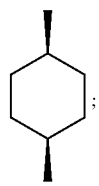

when the cyclohexane is depicted the chair conformer,

trans:

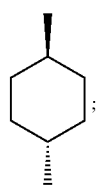

when the cyclohexane is depicted the chair conformer,

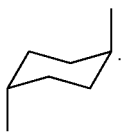

In certain of the compounds herein, having rings capable of forming cis and trans isomers, compounds are described as cis or trans; these designations refer to ring cis and trans isomerism. When such compounds are optically active, i.e., possess chiral centers, cis compounds can be racemates, and are termed cis-racemates; or alternatively trans compounds can be racemates, and are termed trans-racemates.

Rotational Isomerism

It is understood that due to chemical properties (i.e., resonance lending some double bond character to the C—N bond) of restricted rotation about the amide bond linkage (as illustrated below) it is possible to observe separate rotamer species and even, under some circumstances, to isolate such species (see below). It is further understood that certain structural elements, including steric bulk or substituents on the amide nitrogen, may enhance the stability of a rotamer to the extent that a compound may be isolated as, and exist indefinitely, as a single stable rotamer. The present invention therefore includes any possible stable rotamers of formula (I) which are biologically active in the treatment of cancer or other proliferative disease states.

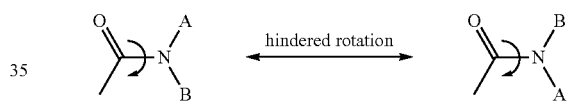

Regioisomerism

The preferred compounds of the present invention have a particular spatial arrangement of substituents on the aromatic rings, which is related to the structure activity relationship demonstrated by the compound class. Often such substitution arrangement is denoted by a numbering system; however, numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below.

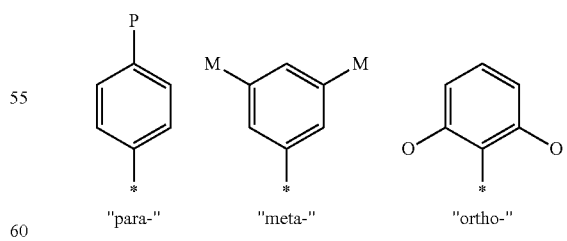

DESCRIPTION

Compounds of the Invention

In various embodiments, the invention is directed to a compound of formula (I)

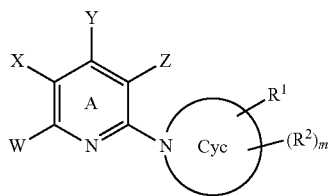
(I)

wherein the ring designated A can further comprise an additional nitrogen atom in any position that bears any of W, X, Y, or Z, provided that the respective group W, X, Y, or Z is absent from that position;

W is H, (C1-C6)alkyl, (C1-C6)haloalkyl, hydroxy(C1-C6)alkyl, (C3-C9)cycloalkyl, or halo;

X is H, halo, nitro, (C1-C6)alkyl, (C1-C6)haloalkyl, hydroxy(C1-C6)alkyl, (C3-C9)cycloalkyl, $NR^aR^b$, $N(R^a)C(=O)(C1-C6)alkyl$, $CO_2R$, or heteroaryl;

Y is H, halo, (C1-C6)alkyl, (C3-C9)cycloalkyl, or halo;

Z is halo, hydroxy, $CO_2R$, $C(=O)NR_2$, CN, heteroaryl $(C_0-C_6)$alkyl, hydroxy(C1-C6)alkyl, HC(=O), HC(=O), (C1-C6)C(=O), or CR(=NOR);

wherein each independently selected R is H, (C1-C6) alkyl, (C3-C9)cycloalkyl, (C6-C10)aryl, or (C6-C10)aryl (C1-C6)alkyl;

or, any adjacent pair of W, X, and Y, can together with the atoms to which they are bonded form a fused cycloalkyl, heterocyclyl, or aryl, or heteroaryl, any of which can be mono- or independently multi-substituted with (C1-C6) alkyl, (C3-C9)cycloalkyl, halo, nitro, $NR^aR^b$, $N(R^a)C(=O)$ (C1-C6)alkyl, $CO_2R$, or heteroaryl;

wherein any alkyl, cycloalkyl, aryl, or heteroaryl of W, X, Y, or Z, can be unsubstituted or can be mono- or independently multi-substituted with (C1-C6)alkyl, (C3-C9)cycloalkyl, halo, nitro, $NR^aR^b$, $N(R^a)C(=O)(C1-C6)alkyl$, $CO_2R$, or heteroaryl;

the ring system Cyc, comprising the nitrogen atom, comprises a mono-, bi-, or tri-cyclic heterocyclyl bonded to ring A via the nitrogen atom, wherein Cyc comprises a 4, 5, 6, 7, or 8 membered ring, optionally bridged with one or two bridges independently comprising 0, 1, or 2 carbon atoms, the ring system Cyc optionally containing 1 or 2 additional heteroatoms selected from NR, O, or $S(O)_q$ wherein q=0, 1, or 2; wherein R', and optionally, m independently selected $R^2$, are bonded to the ring system Cyc, m=0, 1, or 2;

$R^1$ is $(CH_2)_nNR^aR^b$, wherein $R^a$ and $R^b$ are each independently H, alkyl, cycloalkyl, cycloalkylalkyl, heterocyclyl, or heterocyclylalkyl, wherein any alkyl, cycloalkyl, cycloalkylalkyl, heterocyclyl, or heterocyclylalkyl, is substituted with 0, 1, 2, 3, or 4 independently selected J, and wherein any heterocyclyl or cycloalkyl is mono-, bi-, or tri-cyclic; or $R^a$ and $R^b$ together with the nitrogen atom to which they are bonded form a heterocyclyl ring substituted with 0, 1, 2, 3, or 4 independently selected J, wherein n=0, 1, or 2;

or $R^1$ is $(CH_2)_{p1}NR^a(CH_2)_{p2}$ bonded to two carbon atoms of Cyc to form a 5-, 6-, or 7-membered heterocyclyl substituted with 0, 1, 2, 3, or 4 independently selected J, p1 and p2 are independently 0, 1, or 2, provided that p1+p2 is no less than 2;

$R^2$ is (C1-C6)alkyl, hydroxy(C1-C6)alkyl, OR, $CO_2R$, or halo, wherein m=0, 1, or 2;

J is independently at each occurrence OR, (C1-C6)alkyl, hydroxy(C1-C6)alkyl, (C3-C9)cycloalkyl, $CO_2R$, or halo;

or any pharmaceutically acceptable salt thereof.

In various embodiments, the ring designated A can be pyridyl, pyridazinyl, pyrimidyl, or pyrazinyl, or can be fused to provide a quinolyl, tetrahydroquinolyl, quinoxalinyl, or 6,7-dihydro-5H-cyclopenta[b]pyridinyl, any of which can be substituted or unsubstituted.

In various embodiments of a compound of the invention, W can be H or methyl.

In various embodiments of a compound of the invention, X can be H, methyl, ethyl, cyclopropyl, bromo, chloro, fluoro, iodo, trifluoromethyl, nitro, amino, acetamido, butyramido, methoxycarbonyl, ethoxycarbonyl, or oxadiazolyl (substituted or unsubstituted).

In various embodiments of a compound of the invention, Y can be H or chloro.

In various embodiments of a compound of the invention, Z can be methoxycarbonyl, ethoxycarbonyl, hydroxymethyl, formyl, acetyl, O-methylformaldoxime (cis or trans), O-ethylformaldoxime (cis or trans), oxadiazolyl (substituted (alkyl, cycloalkyl) or unsubstituted), pyridazinyl (substituted (alkyl) or unsubstituted), or pyrimidinyl (substituted (alkyl) or unsubstituted).

In various embodiments of a compound of the invention, ring system Cyc is any one of

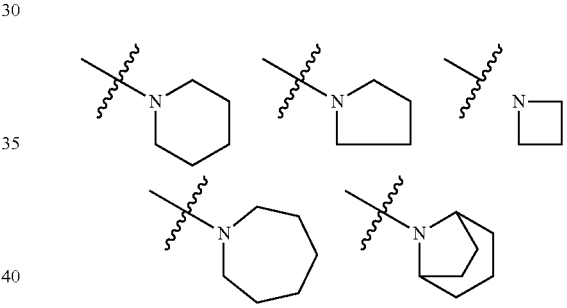

wherein $R^1$ and, optionally, $(R^2)m$, are bonded thereto at any position, and wherein a wavy line indicates a point of bonding.

In various embodiments of a compound of the invention, $R^1$ is $(CH_2)_nNR^aR^b$ and n is 0 or 1; $R^a$ is ethyl, 2-pentyl, 4-methyl-2-pentyl, cyclopropyl, cyclobutyl, cyclopentyl, cyclohexyl, cycloheptyl, cyclooctyl, bicyclo[2.2.1]heptyl, bicyclo[2.2.2]octyl, bornyl, adamantyl, or tetrahydropyranyl, any of which is substituted with 0, 1, 2, 3, or 4 J, and $R^b$ is H.

In various embodiments of a compound of the invention, $R^1$ is $(CH_2)_nNR^aR^b$ and n is 0 or 1; and $R^a$ and $R^b$ together with the nitrogen atom to which they are bonded form a pyrrolidinyl, piperidinyl, azepinyl morpholinyl, or thiomorpholinyl ring, any of which is substituted with 0, 1, 2, 3, or 4 J.

In various embodiments of a compound of the invention, any $R^2$ is independently selected OR, F, Cl, Br, methyl, hydroxymethyl, ethyl, or hydroxyethyl.

In various embodiments of a compound of the invention, $R^2$ is not present.

In various embodiments of a compound of the invention, ring system Cyc and $R^1$ together form a group of formula

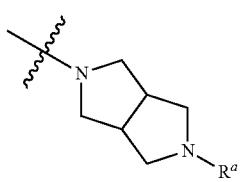

wherein $R^a$ is as defined in herein and a wavy line indicates a point of bonding, and wherein Cyc is optionally substituted with additional $R^2$ groups.

In various embodiments of a compound of the invention, the compound is any of those shown in Table 1, below. A cutoff of $IC_{50}$ >10 μM was chosen to differentiate compounds with potential as medicinal compounds for treatment of conditions in patients wherein inhibition of the kappa opioid receptor are medically indicated from comparative compounds that are largely inactive in this assay, and thus are not expected to be suitable candidates for development of medicinal molecular entities. In Table 1, compounds disclosed and claimed herein are provided with an indexing number, and inactive compounds are designated as "C#" for purposes of identification.

The methods of determining the $IC_{50}$ values of the compounds are provided below.

As is well known in the art, identification of a compound that performs well in an enzyme assay is only a first step in developing a medicinal molecular entity. For example, the candidate compound must meet standards for absorption, distribution, metabolism, excretion, and toxicity (ADMET) in the mammalian body. The inventors herein do not assert that each and every compound disclosed and claimed is a medicinal molecular entity, but that it is a candidate identified for further study in the development of a medicinal molecular entity.

TABLE I

| | Compounds of the Invention | |
|---|---|---|
| Cpd. # | Structure | $IC_{50}$ nM (% inhib if other than 50%) |
| 1 | [Structure: 5-bromo-pyridine with CO2Me, piperidine-N, linked to NH-cyclohexyl-OH] | 231 |
| 2 | [Structure: 4-chloro-6-methyl-pyridine with CO2Et, piperidine-N, linked to NH-cyclohexyl-OH] | 4500 (65%) |
| 3 | [Structure: 5-bromo-pyridine with CO2Me, piperidine-N, linked to NH-cyclopentyl-OH] | 287 |
| 6 | [Structure: 5-bromo-pyridine with COOMe, piperidine-N, linked to NH-CH2CH2-OH] | 9200 (80%) |

TABLE I-continued

Compounds of the Invention

| Cpd. # | Structure | IC$_{50}$ nM (% inhib if other than 50%) |
|---|---|---|
| 7 | 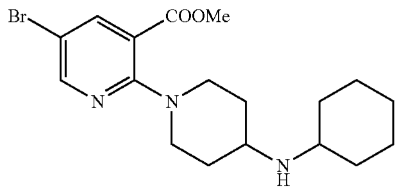 | 133 |
| 8 | 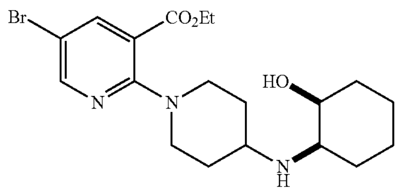 | 579 |
| C1 | 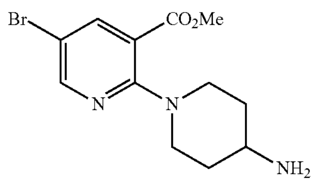 [SMILES: COC(=O)c1cc(Br)cnc1N1CCC(N)CC1] | NA |
| C2 | 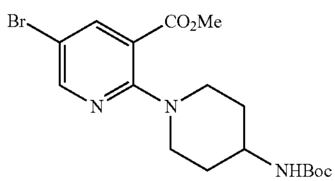 [SMILES: COC(=O)c1cc(Br)cnc1N1CCC(NC(=O)OC(C)(C)C)CC1] | NA |
| C5 | 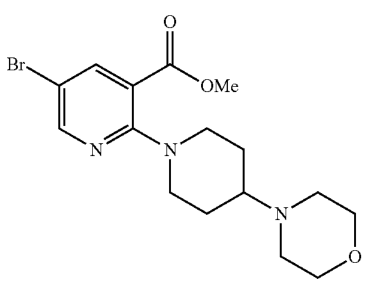 [SMILES: COC(=O)c1cc(Br)cnc1N1CCC(N2CCOCC2)CC1] | NA |
| C6 | 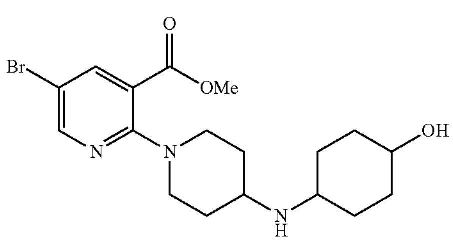 [SMILES: COC(=O)c1cc(Br)cnc1N1CCC(NC2CCC(O)CC2)CC1] | NA |
| 10 | 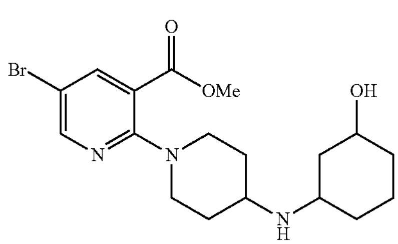 [SMILES: COC(=O)c1cc(Br)cnc1N1CCC(NC2CCCC(O)C2)CC1] | 652 |

TABLE I-continued

Compounds of the Invention

| Cpd. # | Structure | IC$_{50}$ nM (% inhib if other than 50%) |
|---|---|---|
| 11 | 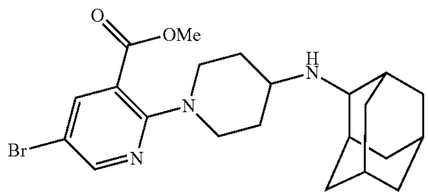 [SMILES: COC(=O)c1cc(Br)cnc1N1CCC(NC2C3CC4CC(C3)CC2C4)CC1] | 2800 |
| C7 | 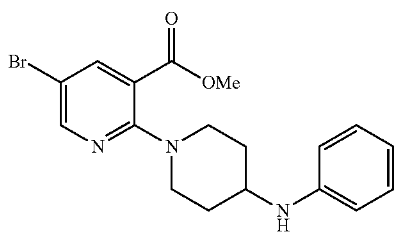 [SMILES: COC(=O)c1cc(Br)cnc1N1CCC(Nc2ccccc2)CC1] | NA |
| C8 | 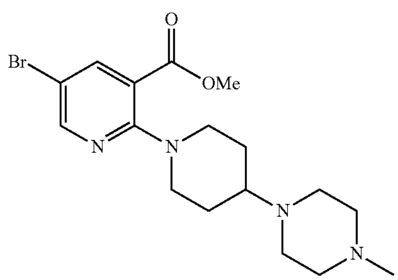 [SMILES: COC(=O)c1cc(Br)cnc1N1CCC(N2CCN(C)CC2)CC1] | NA |
| C9 | 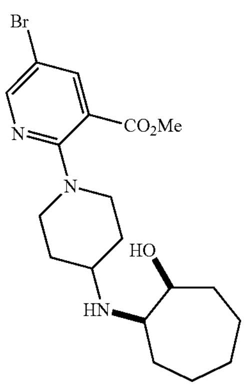 [SMILES: COC(=O)c1cc(Br)cnc1N1CCC(N[C@@H]2CCCCC[C@@H]2O)CC1] | NA |
| 12 | 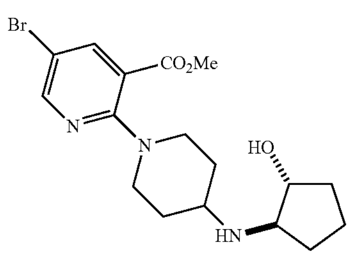 | 765 |

TABLE I-continued

Compounds of the Invention

| Cpd. # | Structure | IC$_{50}$ nM (% inhib if other than 50%) |
|---|---|---|
| C10 | 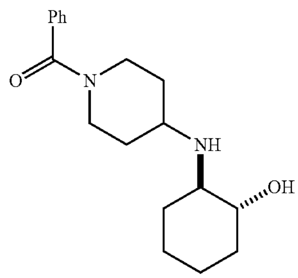 | NA |
| C11 | 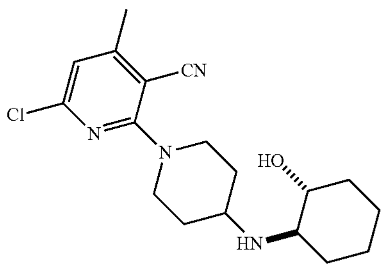 | NA |
| 13 | 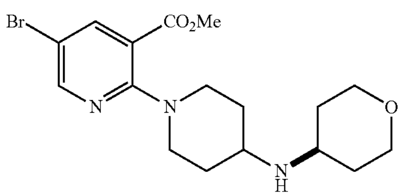 | 621 |
| 14 | 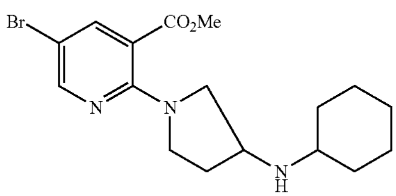 [SMILES: COC(=O)c1cc(Br)cnc1N1CCC(NC2CCCCC2)C1] | 185 |
| 15 | 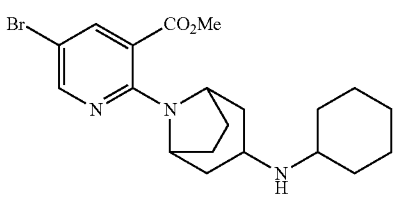 [SMILES: COC(=O)c1cc(Br)cnc1N1C2CCC1CC(NC1CCCCC1)C2] | 7700 |
| 16 | 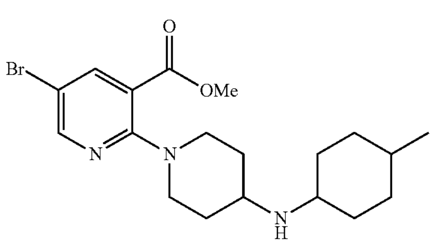 [SMILES: COC(=O)c1cc(Br)cnc1N1CCC(NC2CCC(C)CC2)CC1] | 536 |

TABLE I-continued

Compounds of the Invention

| Cpd. # | Structure | IC$_{50}$ nM (% inhib if other than 50%) |
|---|---|---|
| 17 | 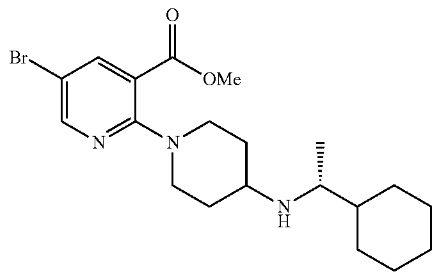 [SMILES: COC(=O)c1cc(Br)cnc1N1CCC(N[C@H](C)C2CCCCC2)CC1] | 6800 |
| C12 | 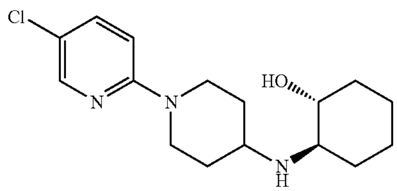 [SMILES: O[C@@H]1CCCC[C@H]1NC1CCN(c2ccc(Cl)cn2)CC1] | NA |
| 18 | 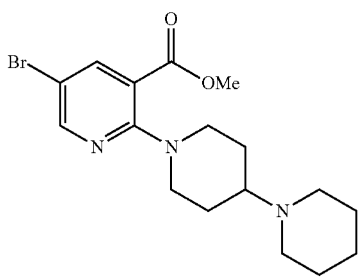 [SMILES: COC(=O)c1cc(Br)cnc1N1CCC(N2CCCCC2)CC1] | 2100 |
| 19 | 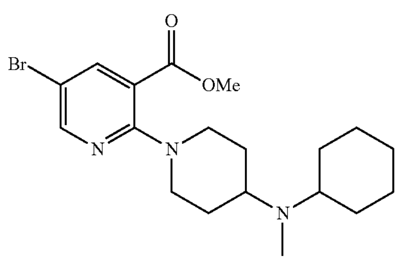 [SMILES: COC(=O)c1cc(Br)cnc1N1CCC(N(C)C2CCCCC2)CC1] | 2700 |
| 20 | 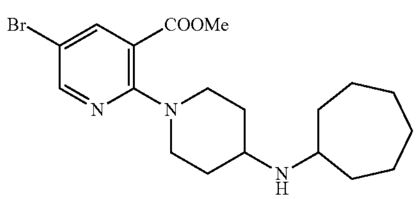 [SMILES: COC(=O)c1cc(Br)cnc1N1CCC(NC2CCCCCC2)CC1] | 110 |
| 21 | 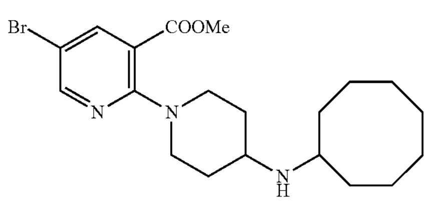 [SMILES: COC(=O)c1cc(Br)cnc1N1CCC(NC2CCCCCCC2)CC1] | 317 |

TABLE I-continued

Compounds of the Invention

| Cpd. # | Structure | IC$_{50}$ nM (% inhib if other than 50%) |
|---|---|---|
| 22 | 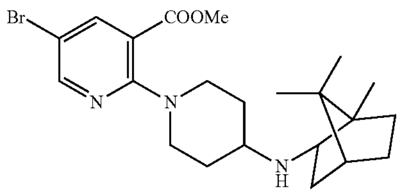 [SMILES: COC(=O)c1cc(Br)cnc1N1CCC(NC2CC3CCC2(C)C3(C)C)CC1] | 10000 |
| 23 | 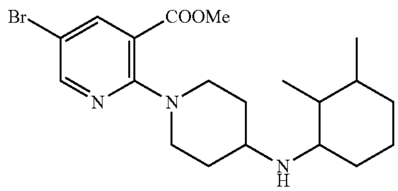 [SMILES: COC(=O)c1cc(Br)cnc1N1CCC(NC2CCCC(C)C2C)CC1] | 854 |
| 24 | 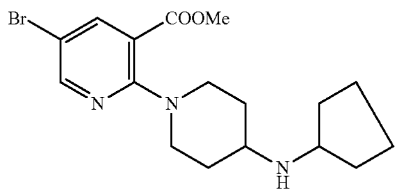 [SMILES: COC(=O)c1cc(Br)cnc1N1CCC(NC2CCCC2)CC1] | 120 |
| 25 | 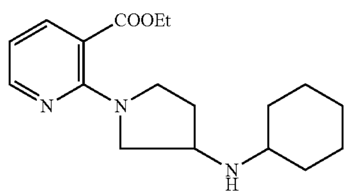 [SMILES: CCOC(=O)c1cccnc1N1CCC(NC2CCCCC2)C1] | 1200 |
| 26 | 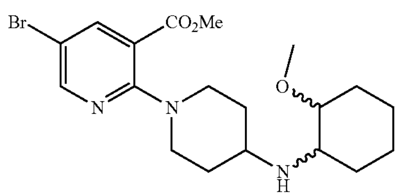 [SMILES: COC(=O)c1cc(Br)cnc1N1CCC(NC2CCCCC2OC)CC1] | 267 |
| 27 | 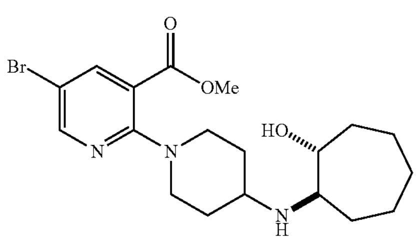 | 473 |
| 28 | 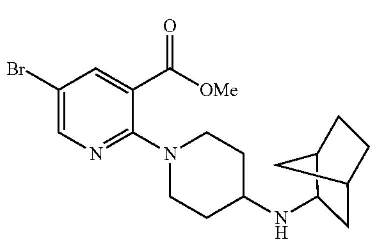 [SMILES: COC(=O)c1cc(Br)cnc1N1CCC(NC2CC3CCC2C3)CC1] | 387 |

TABLE I-continued

Compounds of the Invention

| Cpd. # | Structure | IC$_{50}$ nM (% inhib if other than 50%) |
|---|---|---|
| C13 | 5-Ph, 3-CO$_2$Me pyridine, 2-(4-(cyclohexylamino)piperidin-1-yl) | NA |
| C14 | 5-Br, 3-CO$_2$Me pyridine, 2-(3-(cyclohexylamino)piperidin-1-yl) | NA |
| C15 | 5-cyclopropyl, 3-CO$_2$Me pyridine, 2-(4-(cyclohexylamino)piperidin-1-yl) | NA |
| C16 | 5-Br, 3-CO$_2$Me pyridine, 2-(4-(aminomethyl)piperidin-1-yl) | NA |
| 31 | 5-Br, 3-CO$_2$Me pyridine, 2-(4-((cyclohexylamino)methyl)piperidin-1-yl) | 3500 |
| 32 | 5-(thiophen-3-yl), 3-CO$_2$Me pyridine, 2-(4-(cyclohexylamino)piperidin-1-yl) | 5300 |
| C17 | 5-(cyclohex-1-en-1-yl), 3-CO$_2$Me pyridine, 2-(4-(cyclohexylamino)piperidin-1-yl) | NA |

TABLE I-continued

Compounds of the Invention

| Cpd. # | Structure | IC$_{50}$ nM (% inhib if other than 50%) |
|---|---|---|
| 33 | 5-bromo-2-(3-hydroxy-4-(cyclohexylamino)piperidin-1-yl)nicotinic acid methyl ester | 16 |
| 34 | 5-bromo-2-(4-(cyclohexylamino)piperidin-1-yl)nicotinic acid | 5200 (85%) |
| 35 | 5-iodo-2-(3-(cyclohexylamino)pyrrolidin-1-yl)nicotinic acid methyl ester | 88 |
| 36 | 5-iodo-2-(4-(cyclohexylamino)piperidin-1-yl)nicotinic acid methyl ester | 79 |
| 37 | 5-iodo-2-(4-((2-hydroxycyclohexyl)amino)piperidin-1-yl)nicotinic acid methyl ester | 142 |
| 38 | 5-bromo-2-(4-(cyclohexylamino)piperidin-1-yl)nicotinic acid ethyl ester | 128 |
| 39 | 5-bromo-2-(4-(cyclohexylamino)piperidin-1-yl)nicotinic acid isopropyl ester | 398 |

TABLE I-continued
Compounds of the Invention
| Cpd. # | Structure | IC$_{50}$ nM (% inhib if other than 50%) |
|---|---|---|
| C18 | 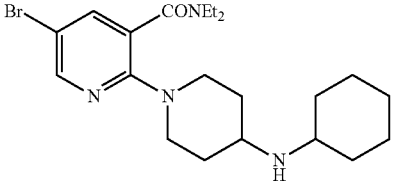 | NA |
| C19 | 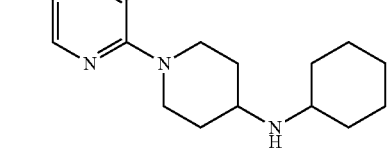 | NA |
| 40 | 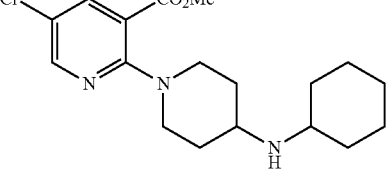 | 159 |
| 41 | 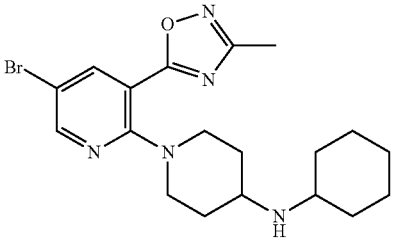 [SMILES: Cc1noc(-c2cc(Br)cnc2N2CCC(NC3CCCCC3)CC2)n1] | 331 |
| 42 | 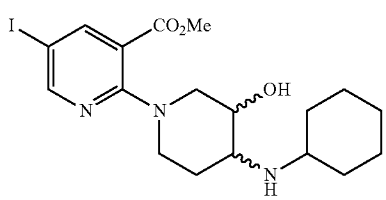 [SMILES: COC(=O)c1cc(I)cnc1N1CCC(NC2CCCCC2)C(O)C1] | 18 |
| 43 | 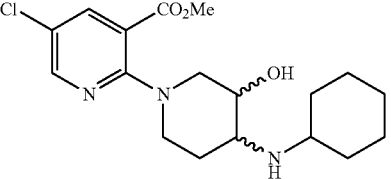 [SMILES: COC(=O)c1cc(Cl)cnc1N1CCC(NC2CCCCC2)C(O)C1] | 52 |
| 44 | 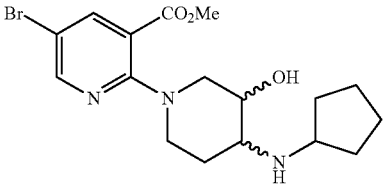 [SMILES: COC(=O)c1cc(Br)cnc1N1CCC(NC2CCCC2)C(O)C1] | 79 |

TABLE I-continued

Compounds of the Invention

| Cpd. # | Structure | IC$_{50}$ nM (% inhib if other than 50%) |
|---|---|---|
| 45 | 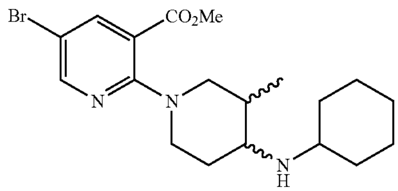 [SMILES: COC(=O)c1cc(Br)cnc1N1CCC(NC2CCCCC2)C(C)C1] | 164 |
| 46 | 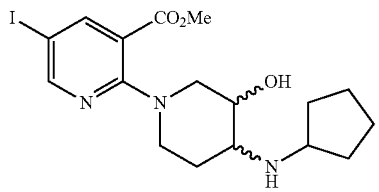 [SMILES: COC(=O)c1cc(I)cnc1N1CCC(NC2CCCC2)C(O)C1] | 25 |
| 47 | 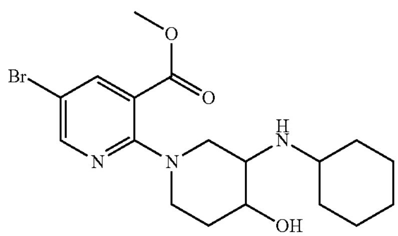 [SMILES: COC(=O)c1cc(Br)cnc1N1CCC(O)C(NC2CCCCC2)C1] | 2800 |
| 48 | 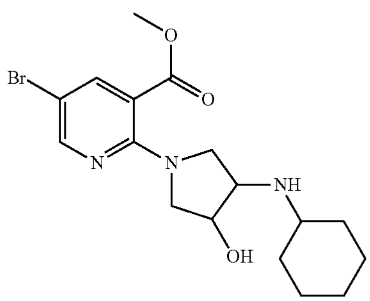 [SMILES: COC(=O)c1cc(Br)cnc1N1CC(O)C(NC2CCCCC2)C1] | 459 |
| 49 | 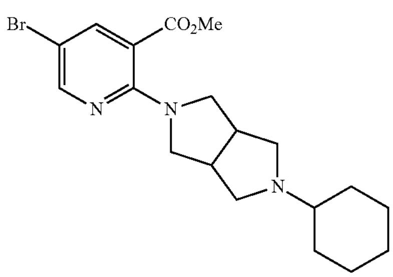 [SMILES: COC(=O)c1cc(Br)cnc1N1CC2CN(C3CCCCC3)CC2C1] | 1300 |
| 50 | 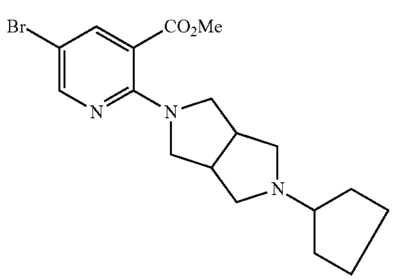 [SMILES: COC(=O)c1cc(Br)cnc1N1CC2CN(C3CCCC3)CC2C1] | 1000 |

TABLE I-continued

Compounds of the Invention

| Cpd. # | Structure | IC$_{50}$ nM (% inhib if other than 50%) |
|---|---|---|
| 51 | 5-Br, 3-CO$_2$Me pyridine; 2-N linked to piperidine with 3-OH and 4-N(Me)(cyclohexyl) | 3000 |
| 52 | 5-Br, 3-CO$_2$Me pyridine; 2-N linked to piperidine with 3-F and 4-NH-cyclohexyl | 3400 |
| 53 | 3-CO$_2$Me pyridine; 2-N linked to piperidine with 3-OH and 4-NH-(2-methylcyclohexyl) | 5600 |
| 54 | 3-CO$_2$Me pyridine; 2-N linked to piperidine with 3-OH and 4-NH-(2-methoxycyclohexyl) | 559 |
| 55 | 3-CO$_2$Me pyridine; 2-N linked to piperidine with 3-OH and 4-NH-cycloheptyl | 1800 |
| 56 | 3-CO$_2$Me pyridine; 2-N linked to piperidine with 3-OH and 4-NH-(tetrahydropyran-4-yl) | 7000 |
| 57 | 3-CO$_2$Me pyridine; 2-N linked to piperidine with 3-OH and 4-NH-cyclohexyl | 2200 |

TABLE I-continued

Compounds of the Invention

| Cpd. # | Structure | IC$_{50}$ nM (% inhib if other than 50%) |
|---|---|---|
| 58 | 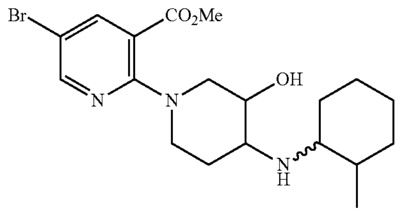 [SMILES: COC(=O)c1cc(Br)cnc1N1CCC(NC2CCCCC2C)C(O)C1] | 419 |
| 59 | 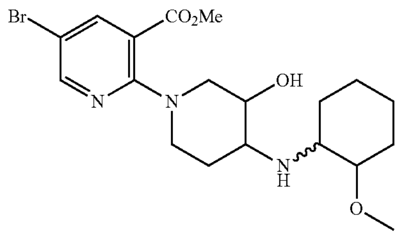 [SMILES: COC(=O)c1cc(Br)cnc1N1CCC(NC2CCCCC2OC)C(O)C1] | 36 |
| 60 | 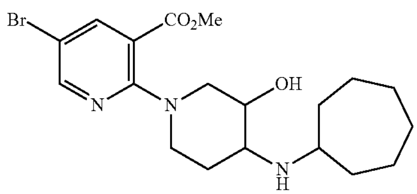 [SMILES: COC(=O)c1cc(Br)cnc1N1CCC(NC2CCCCCC2)C(O)C1] | 68 |
| 61 | 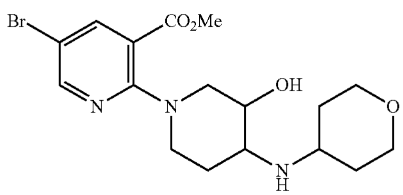 [SMILES: COC(=O)c1cc(Br)cnc1N1CCC(NC2CCOCC2)C(O)C1] | 54 |
| 62 | 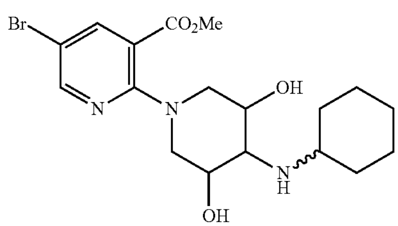 [SMILES: COC(=O)c1cc(Br)cnc1N1CC(O)C(NC2CCCCC2)C(O)C1] | 2700 |
| 63 | 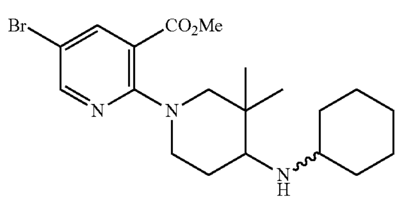 [SMILES: COC(=O)c1cc(Br)cnc1N1CCC(NC2CCCCC2)C(C)(C)C1] | 234 |
| 64 | 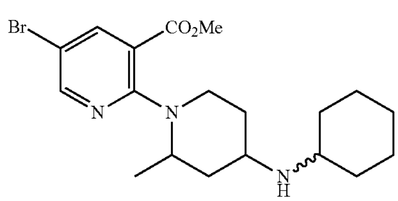 [SMILES: COC(=O)c1cc(Br)cnc1N1CCC(NC2CCCCC2)CC1C] | 901 |

TABLE I-continued

Compounds of the Invention

| Cpd. # | Structure | IC$_{50}$ nM (% inhib if other than 50%) |
|---|---|---|
| C20 | 5-Br-pyridine-3-CO$_2$Me, 2-NH-cyclohexyl-NH-cyclohexyl | NA |
| C21 | 5-Br-pyridine-3-CO$_2$Me, 2-(4-CO$_2$Me-4-NH-cyclohexyl-piperidin-1-yl) | NA |
| 65 | 5-Br-pyridine-3-CO$_2$Me, 2-(4-(2-hydroxymethyl-cyclohexylamino)-piperidin-1-yl) | 2300 |
| 66 | 5-Br-pyridine-3-CO$_2$Me, 2-(4-cyclohexylamino-azepan-1-yl) | 1700 |
| C22 | 5-Br-pyridine-3-CO$_2$Me, 2-(4-(2-hydroxybenzylamino)-piperidin-1-yl) | NA |
| 67 | 5-Br-pyridine-3-CO$_2$Me, 2-(3-cyclohexylamino-azetidin-1-yl) | 1400 |

TABLE I-continued
Compounds of the Invention
| Cpd. # | Structure | IC₅₀ nM (% inhib if other than 50%) |
|---|---|---|
| C23 | 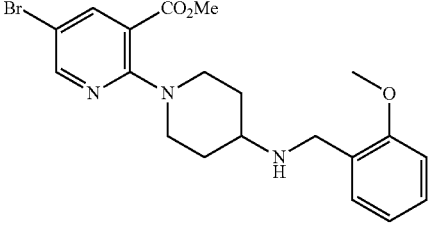 [SMILES: COC(=O)c1cc(Br)cnc1N1CCC(NCc2ccccc2OC)CC1] | NA |
| C24 | 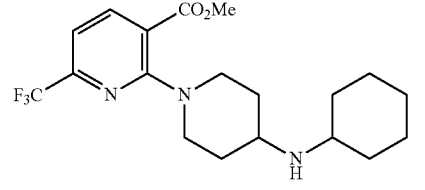 [SMILES: COC(=O)c1ccc(C(F)(F)F)nc1N1CCC(NC2CCCCC2)CC1] | NA |
| C25 | 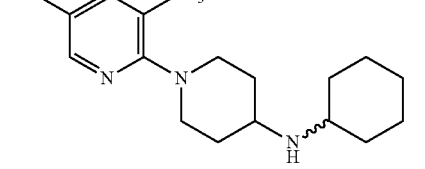 | NA |
| 68 | 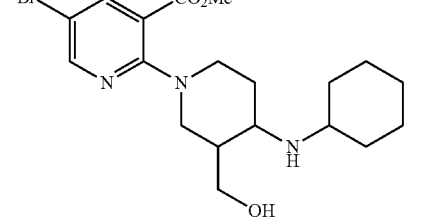 trans-rac | 40 |
| 69 | 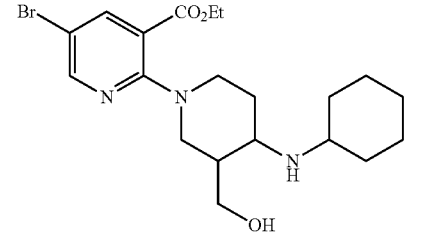 trans-rac | 53 |
| C26 | 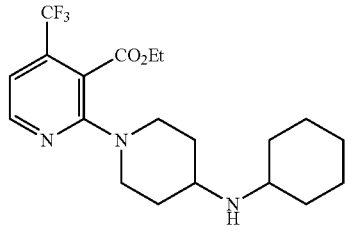 [SMILES: CCOC(=O)c1c(C(F)(F)F)ccnc1N1CCC(NC2CCCCC2)CC1] | NA |

TABLE I-continued
Compounds of the Invention
| Cpd. # | Structure | IC$_{50}$ nM (% inhib if other than 50%) |
|---|---|---|
| 70 | 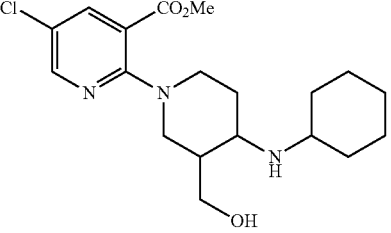 trans-rac | 110 |
| 71 | 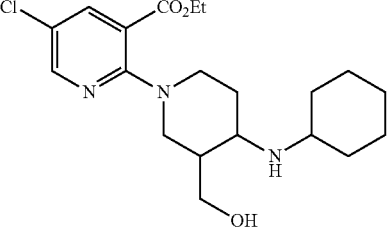 trans-rac | 93 |
| 72 | 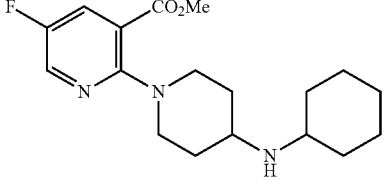 [SMILES: COC(=O)c1cc(F)cnc1N1CCC(NC2CCCCC2)CC1] | 6600 |
| 73 | 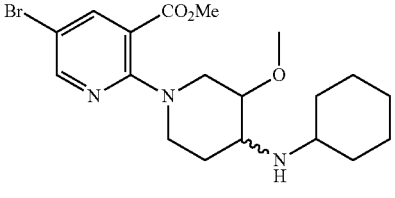 trans-rac | 205 |
| C27 | 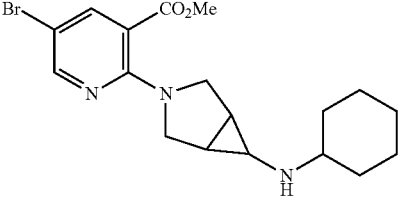 [SMILES: COC(=O)c1cc(Br)cnc1N1CC2C(C1)C2NC1CCCCC1] | 21000 |
| 74 | 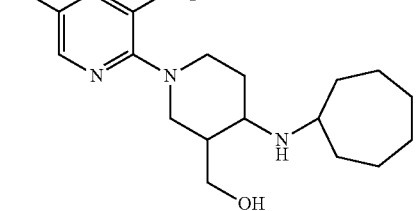 trans-rac | 58 |

TABLE I-continued
Compounds of the Invention
| Cpd. # | Structure | IC$_{50}$ nM (% inhib if other than 50%) |
|---|---|---|
| 75 | 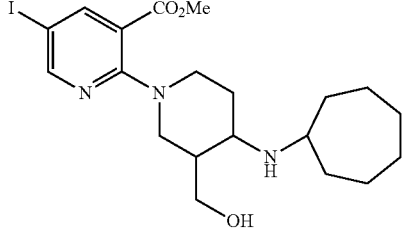 trans-rac | 36 |
| C28 | 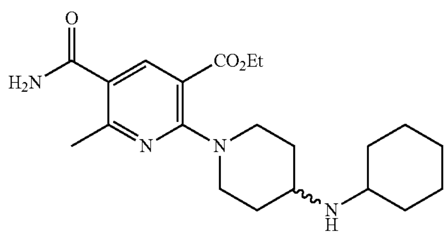 [SMILES: CCOC(=O)c1cc(C(N)=O)c(C)nc1N1CCC(NC2CCCCC2)CC1] | NA |
| 76 | 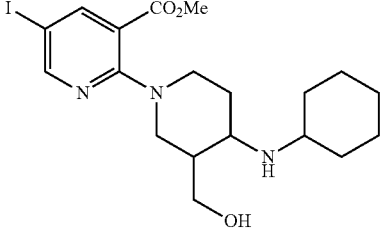 | 11300 |
| 77 | 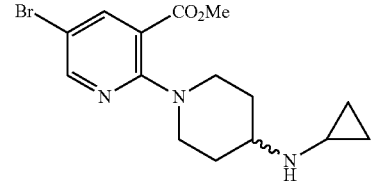 [SMILES: COC(=O)c1cc(Br)cnc1N1CCC(NC2CC2)CC1] trans-rac | 11 |
| 78 | 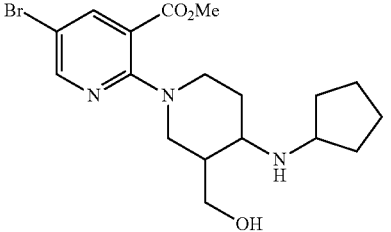 | 1200 |
| 79 |  trans-rac | 25 |

TABLE I-continued
Compounds of the Invention
| Cpd. # | Structure | IC$_{50}$ nM (% inhib if other than 50%) |
|---|---|---|
| 80 | 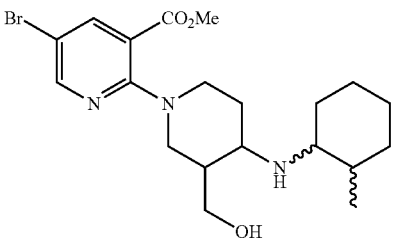 trans-rac | 87 |
| 81 | 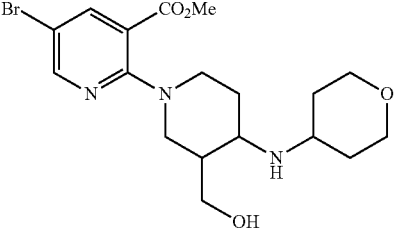 trans-rac | 126 |
| 82 | 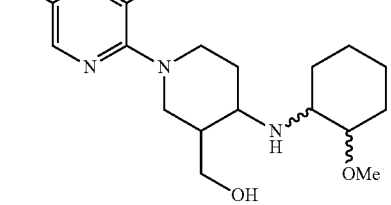 trans-rac | 127 |
| 83 | 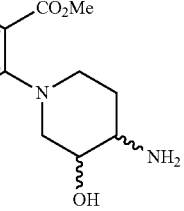 | 5900 |
| 84 | 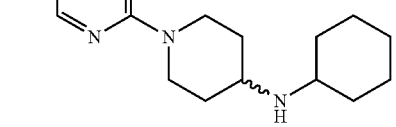 | 6200 |
| 85 | 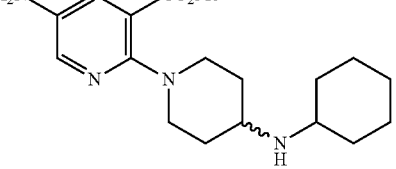 | 1800 |

TABLE I-continued
Compounds of the Invention
| Cpd. # | Structure | IC$_{50}$ nM (% inhib if other than 50%) |
|---|---|---|
| C29 | 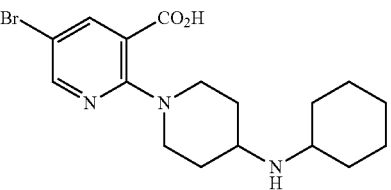 [SMILES: O=C(O)c1cc(Br)cnc1N1CCC(NC2CCCCC2)CC1] | NA |
| 86 | 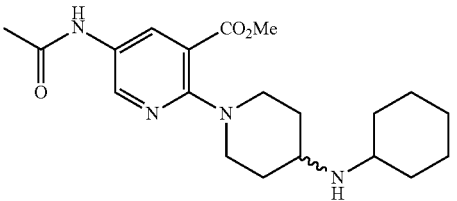 [SMILES: COC(=O)c1cc(NC(C)=O)cnc1N1CCC(NC2CCCCC2)CC1] | 628 |
| C30 | 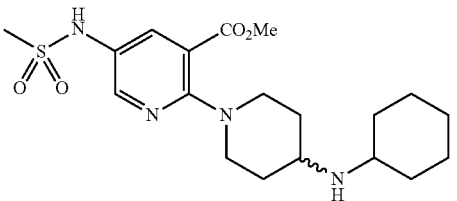 [SMILES: COC(=O)c1cc(NS(C)(=O)=O)cnc1N1CCC(NC2CCCCC2)CC1] | NA |
| 87 | 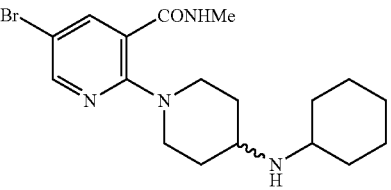 | 19000 |
| C31 | 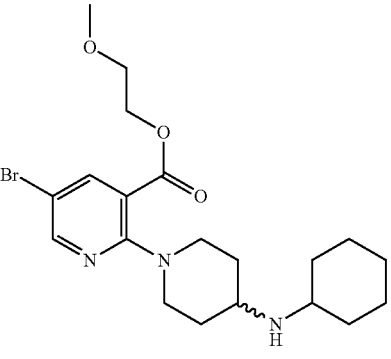 [SMILES: COCCOC(=O)c1cc(Br)cnc1N1CCC(NC2CCCCC2)CC1] | NA |
| C32 | 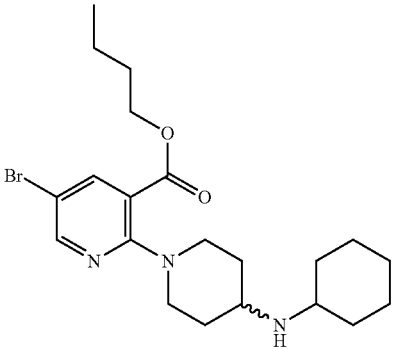 [SMILES: CCCCOC(=O)c1cc(Br)cnc1N1CCC(NC2CCCCC2)CC1] | NA |

61
TABLE I-continued
Compounds of the Invention
| Cpd. # | Structure | IC$_{50}$ nM (% inhib if other than 50%) |
|---|---|---|
| 88 | 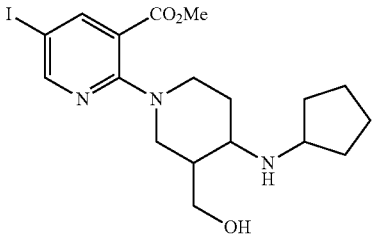<br>trans-rac | 52 |
| 89 | 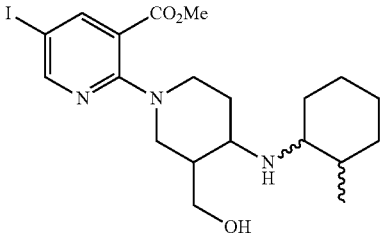<br>trans-rac | 116 |
| 90 | 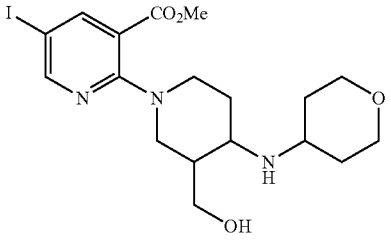<br>trans-rac | 186 |
| 91 | 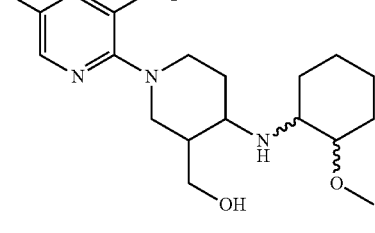<br>trans-rac | 198 |
| 92 | 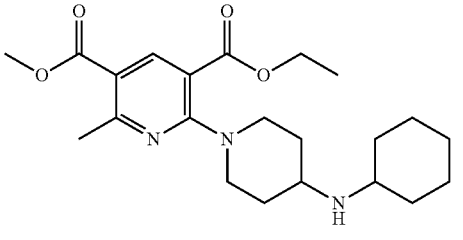 [SMILES: CCOC(=O)c1cc(C(=O)OC)c(C)nc1N1CCC(NC2CCCCC2)CC1] | 2600 |

TABLE I-continued

Compounds of the Invention

| Cpd. # | Structure | IC$_{50}$ nM (% inhib if other than 50%) |
|---|---|---|
| 93 | (structure) trans-rac | 621 |
| 94 | (structure) | 61 |
| C33 | (structure) | NA |
| 95 | (structure) | 1.4 |
| C34 | (structure) | NA |

TABLE I-continued

Compounds of the Invention

| Cpd. # | Structure | IC$_{50}$ nM (% inhib if other than 50%) |
|---|---|---|
| C35 | 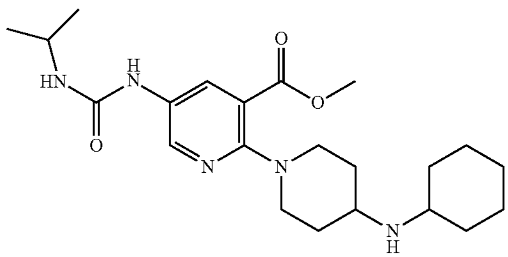 [SMILES: COC(=O)c1cc(NC(=O)NC(C)C)cnc1N1CCC(NC2CCCCC2)CC1] | 17000 |
| C36 | 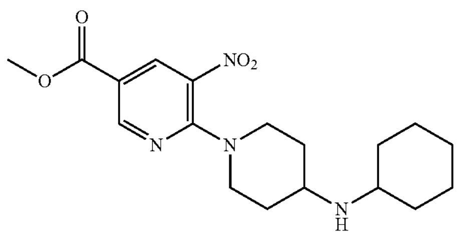 [SMILES: COC(=O)c1cnc(N2CCC(NC3CCCCC3)CC2)c([N+](=O)[O-])c1] | 17000 |
| C37 | 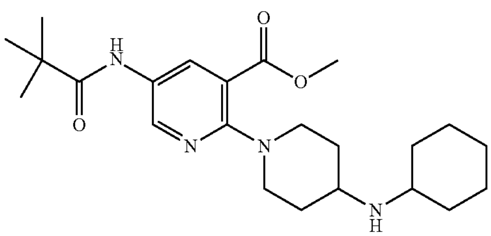 [SMILES: COC(=O)c1cc(NC(=O)C(C)(C)C)cnc1N1CCC(NC2CCCCC2)CC1] | NA |
| C38 | 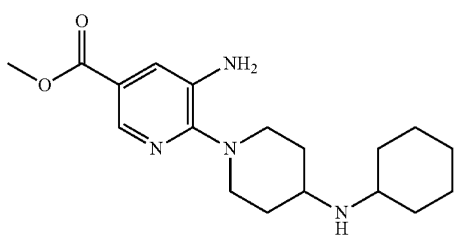 [SMILES: COC(=O)c1cnc(N2CCC(NC3CCCCC3)CC2)c(N)c1] | NA |
| C39 | 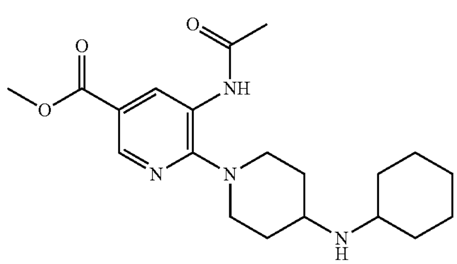 [SMILES: COC(=O)c1cnc(N2CCC(NC3CCCCC3)CC2)c(NC(C)=O)c1] | NA |
| C40 | 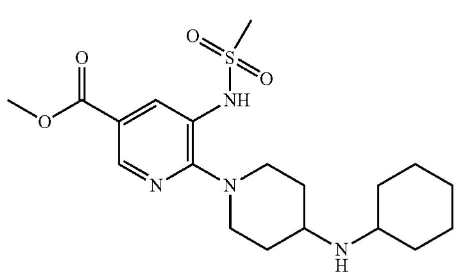 [SMILES: COC(=O)c1cnc(N2CCC(NC3CCCCC3)CC2)c(NS(C)(=O)=O)c1] | NA |

TABLE I-continued

Compounds of the Invention

| Cpd. # | Structure | IC$_{50}$ nM (% inhib if other than 50%) |
|---|---|---|
| C41 | 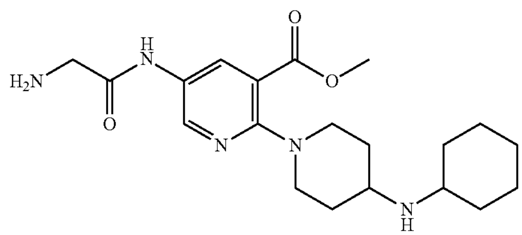 [SMILES: COC(=O)c1cc(NC(=O)CN)cnc1N1CCC(NC2CCCCC2)CC1] | NA |
| C42 | 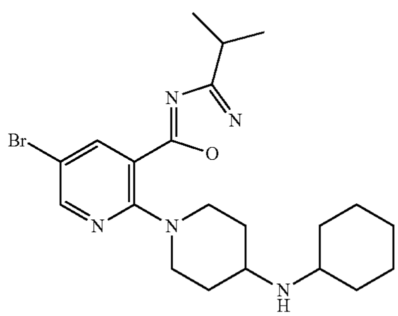 [SMILES: CC(C)C(=N)/N=C(\O)c1cc(Br)cnc1N1CCC(NC2CCCCC2)CC1] | NA |
| C43 | 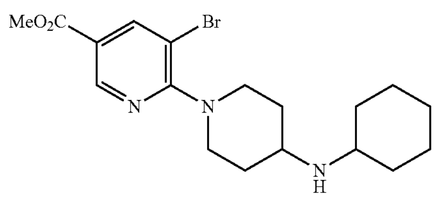 [SMILES: COC(=O)c1cnc(N2CCC(NC3CCCCC3)CC2)c(Br)c1] | 15000 |
| C44 | 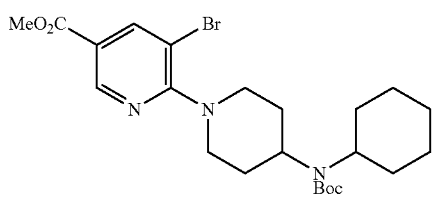 [SMILES: COC(=O)c1cnc(N2CCC(N(C(=O)OC(C)(C)C)C3CCCCC3)CC2)c(Br)c1] | NA |
| 96 | 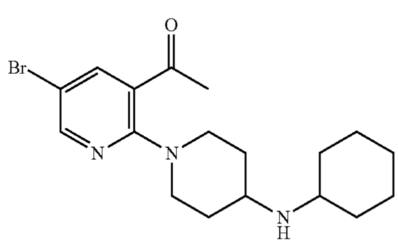 [SMILES: CC(=O)c1cc(Br)cnc1N1CCC(NC2CCCCC2)CC1] | 6700 |
| 97 | (trans-rac) | 2000 |

TABLE I-continued

Compounds of the Invention

| Cpd. # | Structure | IC$_{50}$ nM (% inhib if other than 50%) |
|---|---|---|
| 98 | 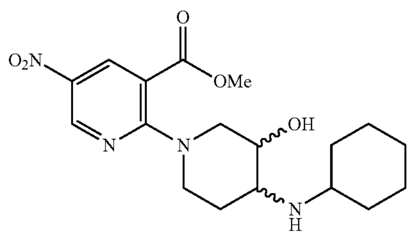 [SMILES: COC(=O)c1cc([N+](=O)[O-])cnc1N1CCC(NC2CCCCC2)C(O)C1] | 1100 |
| 99 | 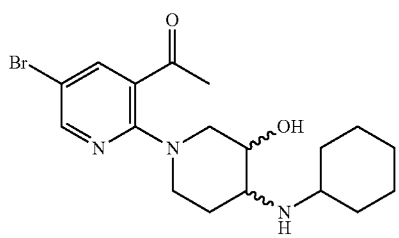 [SMILES: CC(=O)c1cc(Br)cnc1N1CCC(NC2CCCCC2)C(O)C1] | 4500 |
| C45 | 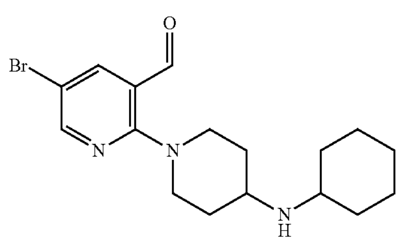 [SMILES: O=Cc1cc(Br)cnc1N1CCC(NC2CCCCC2)CC1] | NA |
| C46 | trans-rac | NA |
| 100 | 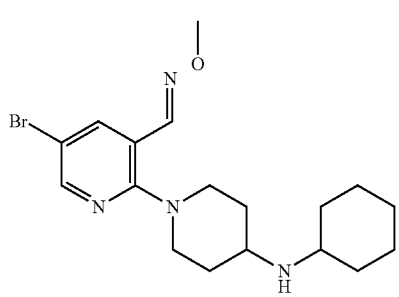 | 292 |

TABLE I-continued
Compounds of the Invention
| Cpd. # | Structure | IC$_{50}$ nM (% inhib if other than 50%) |
|---|---|---|
| 101 | 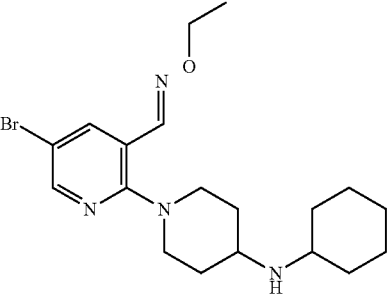 | 4000 |
| C47 | 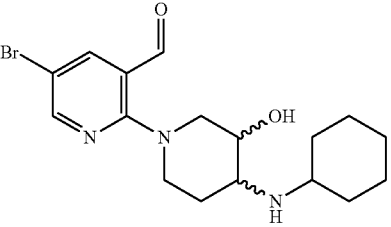 [SMILES: O=Cc1cc(Br)cnc1N1CCC(NC2CCCCC2)C(O)C1] | NA |
| 102 | 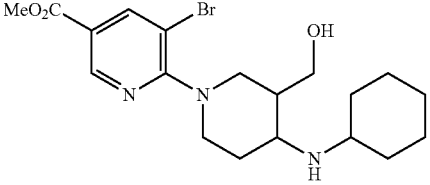 trans-rac | 13000 |
| 103 | 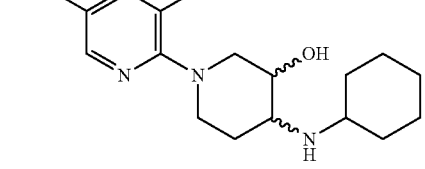 | 137 |
| 104 | 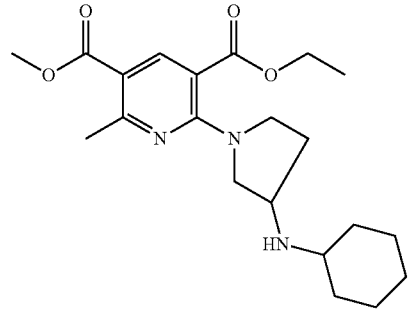 [SMILES: CCOC(=O)c1cc(C(=O)OC)c(C)nc1N1CCC(NC2CCCCC2)C1] | 2200 |

TABLE I-continued

Compounds of the Invention

| Cpd. # | Structure | IC$_{50}$ nM (% inhib if other than 50%) |
|---|---|---|
| C48 | 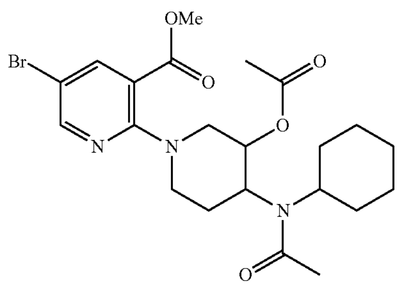 [SMILES: COC(=O)c1cc(Br)cnc1N1CCC(N(C(C)=O)C2CCCCC2)C(OC(C)=O)C1] | NA |
| C49 | 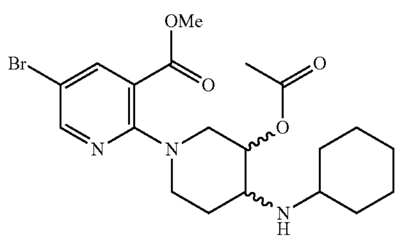 [SMILES: COC(=O)c1cc(Br)cnc1N1CCC(NC2CCCCC2)C(OC(C)=O)C1] | 17000 |
| 105 | 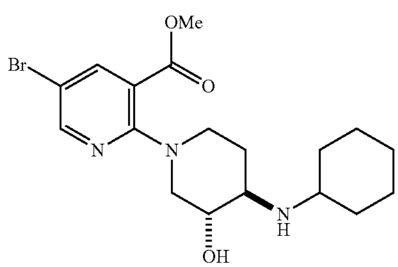 [SMILES: COC(=O)c1cc(Br)cnc1N1CC[C@@H](NC2CCCCC2)[C@H](O)C1] | 56 |
| C50 | 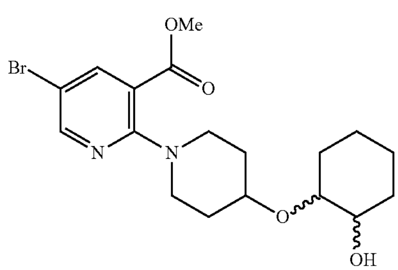 [SMILES: COC(=O)c1cc(Br)cnc1N1CCC(OC2CCCCC2O)CC1] | NA |
| 106 | 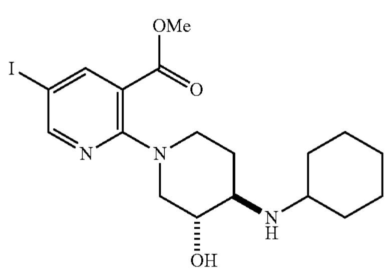 [SMILES: COC(=O)c1cc(I)cnc1N1CC[C@@H](NC2CCCCC2)[C@H](O)C1] | 24 |

TABLE I-continued

Compounds of the Invention

| Cpd. # | Structure | IC$_{50}$ nM (% inhib if other than 50%) |
|---|---|---|
| 107 | 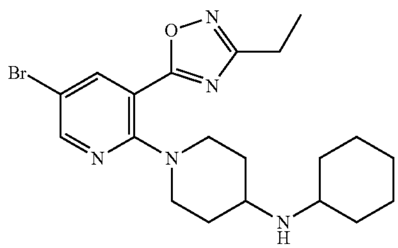 [SMILES: CCc1noc(-c2cc(Br)cnc2N2CCC(NC3CCCCC3)CC2)n1] | 11000 |
| 108 | 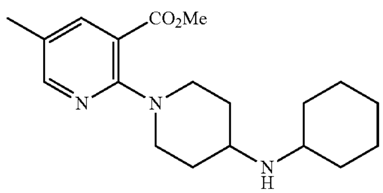 [SMILES: COC(=O)c1cc(C)cnc1N1CCC(NC2CCCCC2)CC1] | 404 |
| 109 | trans-rac | 198 |
| 110 | 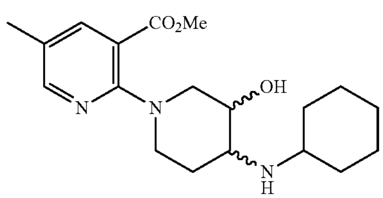 [SMILES: COC(=O)c1cc(C)cnc1N1CCC(NC2CCCCC2)C(O)C1] | 108 |
| C51 | 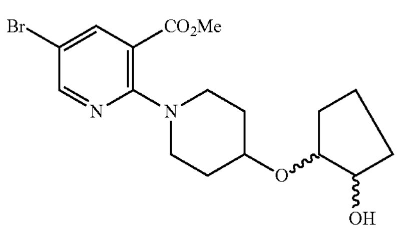 [SMILES: COC(=O)c1cc(Br)cnc1N1CCC(OC2CCCC2O)CC1] | >20000 |
| C52 | trans-rac | >20000 |

TABLE I-continued

Compounds of the Invention

| Cpd. # | Structure | IC$_{50}$ nM (% inhib if other than 50%) |
|---|---|---|
| C53 | 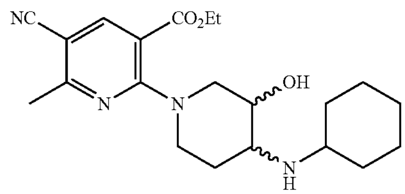 [SMILES: CCOC(=O)c1cc(C#N)c(C)nc1N1CCC(NC2CCCCC2)C(O)C1] | 13000 |
| C54 | 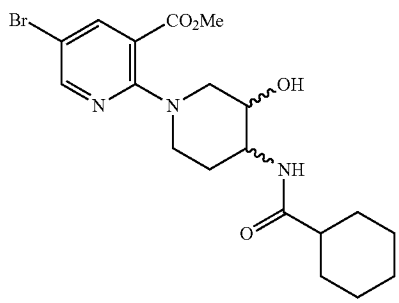 [SMILES: COC(=O)c1cc(Br)cnc1N1CCC(NC(=O)C2CCCCC2)C(O)C1] | >20000 |
| 111 | 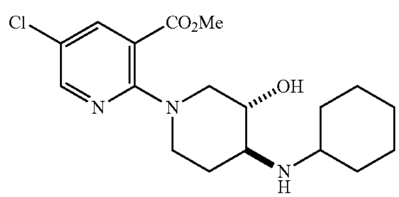 [SMILES: COC(=O)c1cc(Cl)cnc1N1CC[C@H](NC2CCCCC2)[C@@H](O)C1] | 281 |
| C55 | 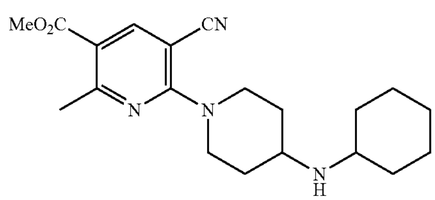 [SMILES: COC(=O)c1cc(C#N)c(N2CCC(NC3CCCCC3)CC2)nc1C] | >20000 |
| C56 | (trans-rac) | >20000 |
| C57 | 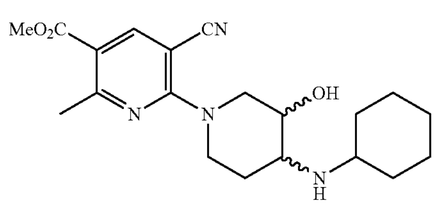 [SMILES: COC(=O)c1cc(C#N)c(N2CCC(NC3CCCCC3)C(O)C2)nc1C] | >20000 |

TABLE I-continued
Compounds of the Invention
| Cpd. # | Structure | IC$_{50}$ nM (% inhib if other than 50%) |
|---|---|---|
| 112 | 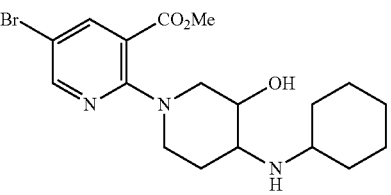<br>cis-rac | 714 |
| C58 | 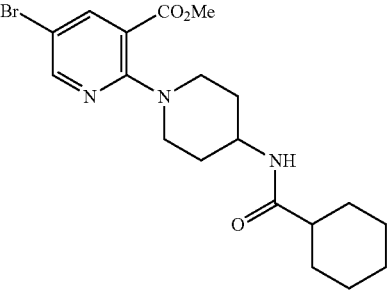 [SMILES: COC(=O)c1cc(Br)cnc1N1CCC(NC(=O)C2CCCCC2)CC1] | >20000 |
| 113 | 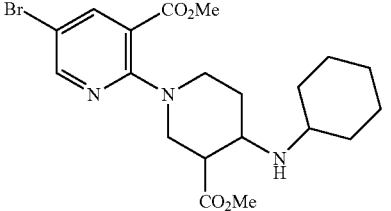<br>cis-rac | 2000 |
| 114 | 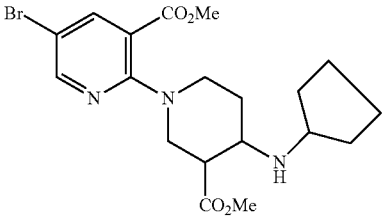<br>cis-rac | 1200 |
| 115 | 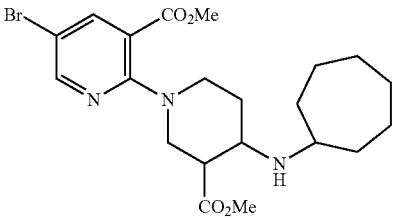<br>cis-rac | 1700 |

TABLE I-continued

Compounds of the Invention

| Cpd. # | Structure | IC$_{50}$ nM (% inhib if other than 50%) |
|---|---|---|
| 116 | (trans-rac) methyl 5-bromo-2-[4-(cyclohexylamino)-3-(methoxycarbonyl)piperidin-1-yl]nicotinate | 793 |
| 117 | (trans-rac) methyl 5-bromo-2-[4-(cyclopentylamino)-3-(methoxycarbonyl)piperidin-1-yl]nicotinate | 3800 |
| 118 | (trans-rac) methyl 5-bromo-2-[4-(cycloheptylamino)-3-(methoxycarbonyl)piperidin-1-yl]nicotinate | 661 |
| C59 | ethyl (E)-3-{5-[6-[4-(cyclohexylamino)piperidin-1-yl]-5-(methoxycarbonyl)pyridin-3-yl]}acrylate | >20000 |
| 119 | 3-ethyl 5-methyl 2-[4-(cyclohexylamino)-3-hydroxypiperidin-1-yl]-6-methylpyridine-3,5-dicarboxylate | 12 |

TABLE I-continued
Compounds of the Invention
| Cpd. # | Structure | IC₅₀ nM (% inhib if other than 50%) |
|---|---|---|
| 120 | 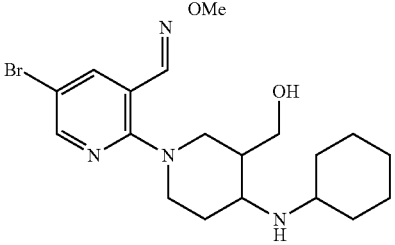 trans-rac | 16 |
| 121 | 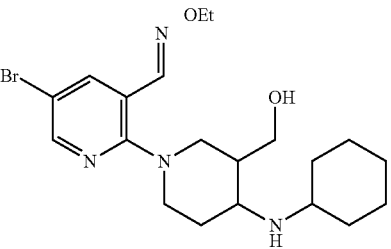 trans-rac | 45 |
| 122 | 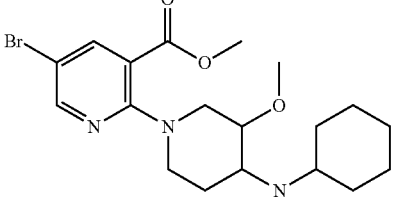 cis-rac | 125 |
| 123 | 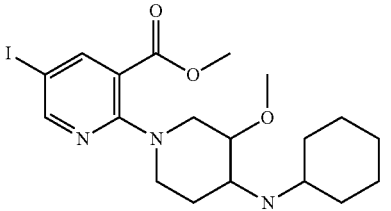 cis-rac | 11 |
| 124 | 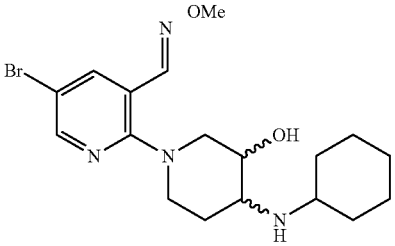 [SMILES: N=Cc1cc(Br)cnc1N1CCC(NC2CCCCC2)C(O)C1 ; "OMe"] | 31 |

TABLE I-continued
Compounds of the Invention
| Cpd. # | Structure | IC$_{50}$ nM (% inhib if other than 50%) |
|---|---|---|
| 125 | 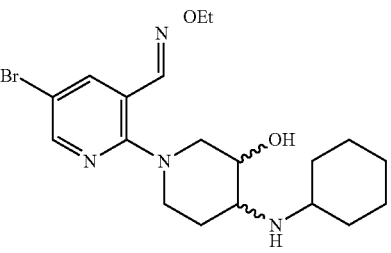 [SMILES: N=Cc1cc(Br)cnc1N1CCC(NC2CCCCC2)C(O)C1 ; "OEt"] | 41 |
| 126 | 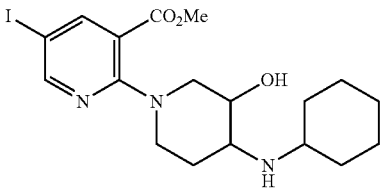<br>cis-rac | 112 |
| 127 | 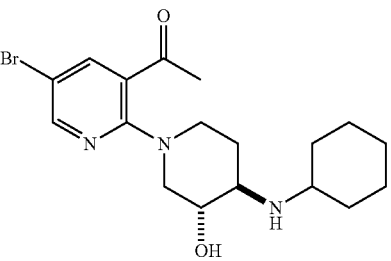 [SMILES: CC(=O)c1cc(Br)cnc1N1CC[C@@H](NC2CCCCC2)[C@H](O)C1] | 33 |
| 128 | 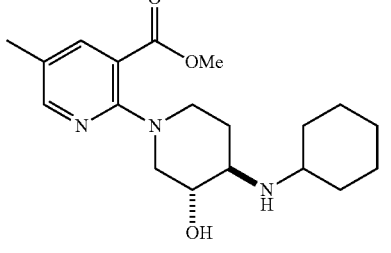 | 35 |
| 129 | 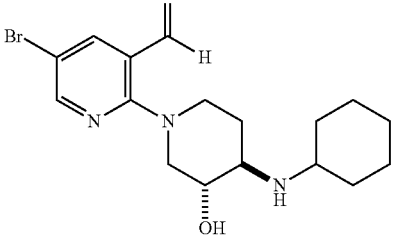 | 799 |

TABLE I-continued

Compounds of the Invention

| Cpd. # | Structure | IC$_{50}$ nM (% inhib if other than 50%) |
|---|---|---|
| 130 | 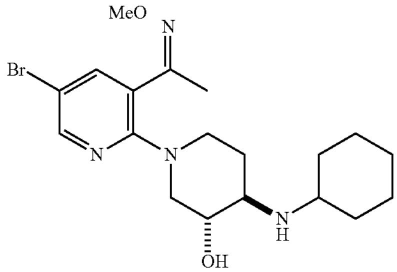 [SMILES: CC(=N)c1cc(Br)cnc1N1CC[C@@H](NC2CCCCC2)[C@H](O)C1 ; "MeO"] | 22 |
| 131 | 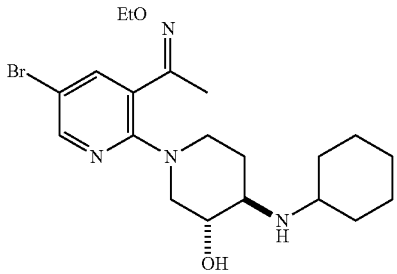 [SMILES: CC(=N)c1cc(Br)cnc1N1CC[C@@H](NC2CCCCC2)[C@H](O)C1 ; "EtO"] | 30 |
| 132 | 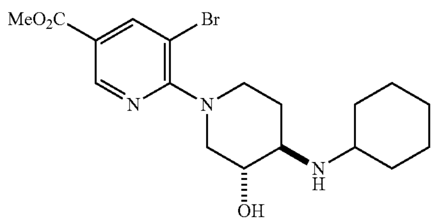 [SMILES: COC(=O)c1cnc(N2CC[C@@H](NC3CCCCC3)[C@H](O)C2)c(Br)c1] | 4000 |
| 133 | 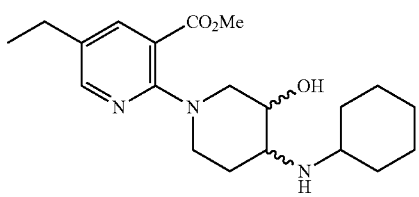 [SMILES: CCc1cnc(N2CCC(NC3CCCCC3)C(O)C2)c(C(=O)OC)c1] | 272 |
| 134 | 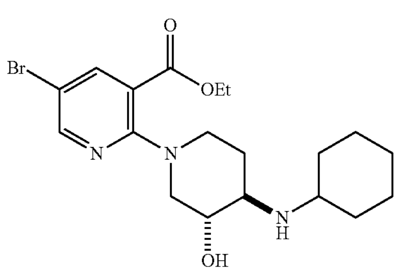 [SMILES: CCOC(=O)c1cc(Br)cnc1N1CC[C@@H](NC2CCCCC2)[C@H](O)C1] | 23 |
| C60 | 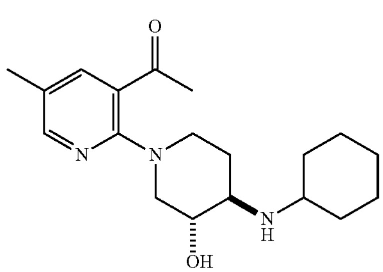 [SMILES: CC(=O)c1cc(C)cnc1N1CC[C@@H](NC2CCCCC2)[C@H](O)C1] | 14000 |

TABLE I-continued

Compounds of the Invention

| Cpd. # | Structure | IC$_{50}$ nM (% inhib if other than 50%) |
|---|---|---|
| 135 | 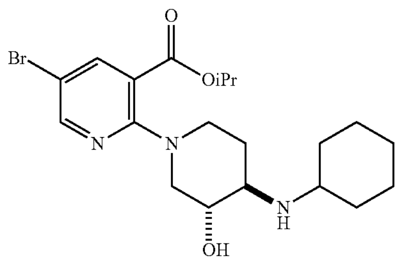 [SMILES: CC(C)OC(=O)c1cc(Br)cnc1N1CC[C@@H](NC2CCCCC2)[C@H](O)C1] | 1630 |
| 136 | 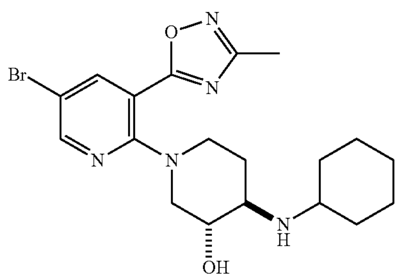 | 49 |
| 137 | 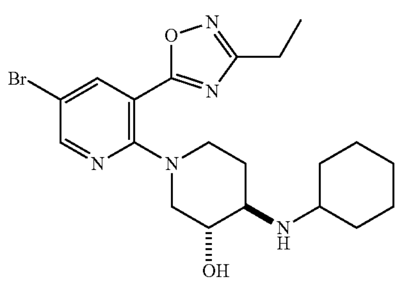 [SMILES: CCc1noc(-c2cc(Br)cnc2N2CC[C@@H](NC3CCCCC3)[C@H](O)C2)n1] | 1600 |
| 138 | 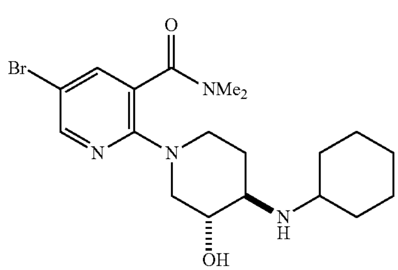 [SMILES: CN(C)C(=O)c1cc(Br)cnc1N1CC[C@@H](NC2CCCCC2)[C@H](O)C1] | 3200 |
| 139 | 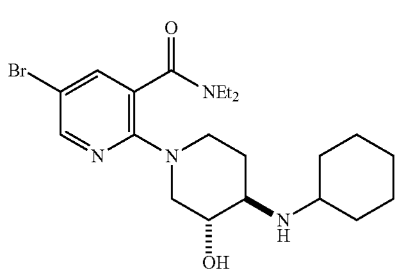 | 4800 |

TABLE I-continued

Compounds of the Invention

| Cpd. # | Structure | IC$_{50}$ nM (% inhib if other than 50%) |
|---|---|---|
| 140 | 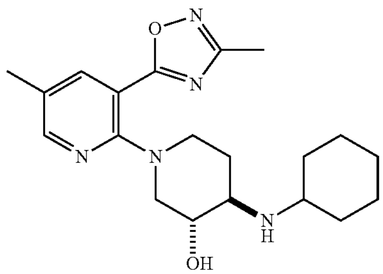 [SMILES: Cc1cnc(N2CC[C@@H](NC3CCCCC3)[C@H](O)C2)c(-c2nc(C)no2)c1] | 54 |
| 141 | 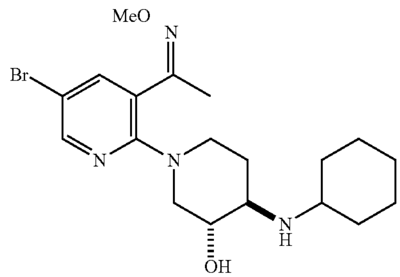 [SMILES: CC(=N)c1cc(Br)cnc1N1CC[C@@H](NC2CCCCC2)[C@H](O)C1 ; "MeO"] | 107 |
| 142 | 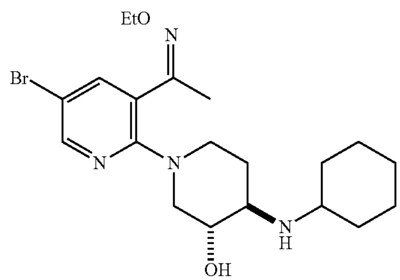 [SMILES: CC(=N)c1cc(Br)cnc1N1CC[C@@H](NC2CCCCC2)[C@H](O)C1 ; "EtO"] | 125 |
| 143 | cis-rac | 100 |
| 144 | trans-rac | 4800 |

TABLE I-continued

Compounds of the Invention

| Cpd. # | Structure | IC$_{50}$ nM (% inhib if other than 50%) |
|---|---|---|
| C61 | cis-rac | 10000 |
| 145 | trans-rac | 117 |
| 146 | cis-rac | 85 |
| 147 | 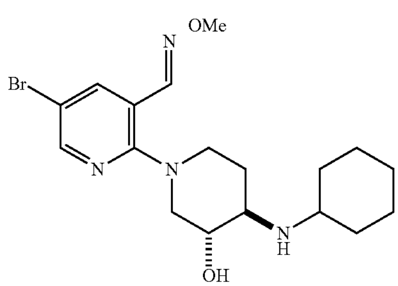 [SMILES: N=Cc1cc(Br)cnc1N1CC[C@@H](NC2CCCCC2)[C@H](O)C1] | 206 |
| 148 | 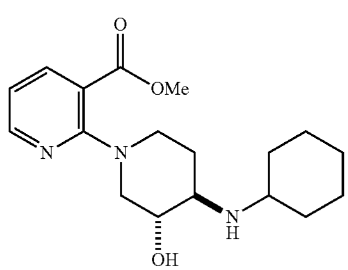 [SMILES: COC(=O)c1cccnc1N1CC[C@@H](NC2CCCCC2)[C@H](O)C1] | 5800 |

TABLE I-continued
Compounds of the Invention
| Cpd. # | Structure | IC$_{50}$ nM (% inhib if other than 50%) |
|---|---|---|
| 149 | 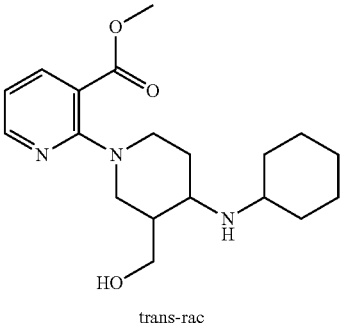 [SMILES: COC(=O)c1cccnc1N1CCC(NC2CCCCC2)C(CO)C1] trans-rac | 5400 |
| 150 | 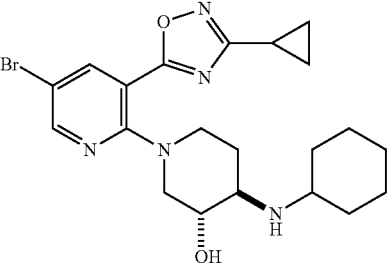 [SMILES: O[C@@H]1CN(c2ncc(Br)cc2-c2nc(C3CC3)no2)CC[C@H]1NC1CCCCC1] | 9100 |
| 151 | 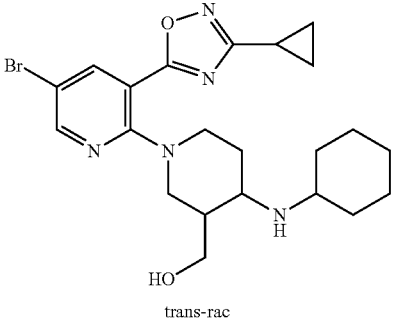 [SMILES: OCC1CN(c2ncc(Br)cc2-c2nc(C3CC3)no2)CCC1NC1CCCCC1] trans-rac | 2100 |
| 152 | 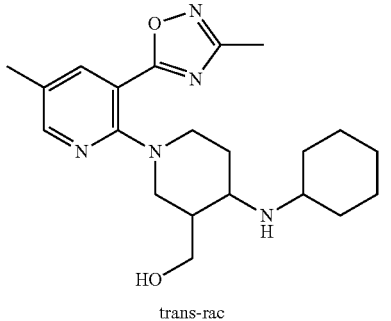 [SMILES: Cc1cnc(N2CCC(NC3CCCCC3)C(CO)C2)c(-c2nc(C)no2)c1] trans-rac | 30 |

TABLE I-continued

Compounds of the Invention

| Cpd. # | Structure | IC$_{50}$ nM (% inhib if other than 50%) |
|---|---|---|
| 153 | 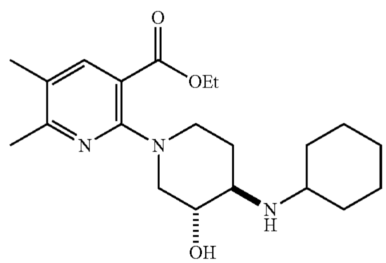 [SMILES: CCOC(=O)c1cc(C)c(C)nc1N1CC[C@@H](NC2CCCCC2)[C@H](O)C1] | 191 |
| 154 | 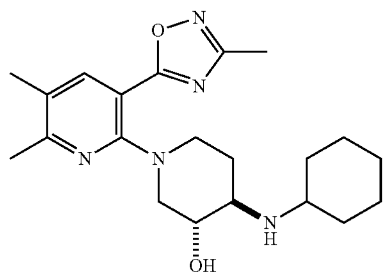 [SMILES: Cc1noc(-c2cc(C)c(C)nc2N2CC[C@@H](NC3CCCCC3)[C@H](O)C2)n1] | 146 |
| C62 | 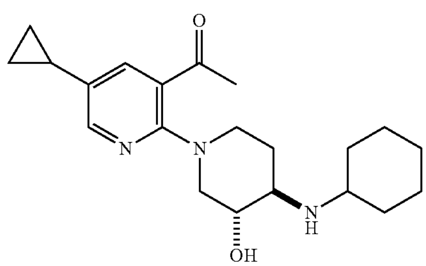 [SMILES: CC(=O)c1cc(C2CC2)cnc1N1CC[C@@H](NC2CCCCC2)[C@H](O)C1] | NA |
| C63 | trans-rac | NA |
| C64 | trans-rac | NA |

TABLE I-continued

Compounds of the Invention

| Cpd. # | Structure | IC$_{50}$ nM (% inhib if other than 50%) |
|---|---|---|
| C65 | 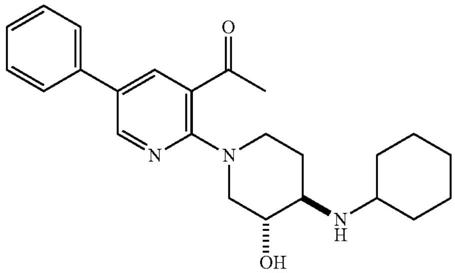 [SMILES: CC(=O)c1cc(-c2ccccc2)cnc1N1CC[C@@H](NC2CCCCC2)[C@H](O)C1] | NA |
| 155 | 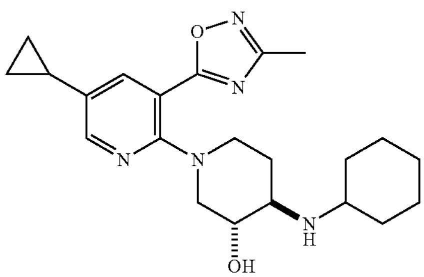 [SMILES: Cc1noc(-c2cc(C3CC3)cnc2N2CC[C@@H](NC3CCCCC3)[C@H](O)C2)n1] | 1300 |
| C66 | 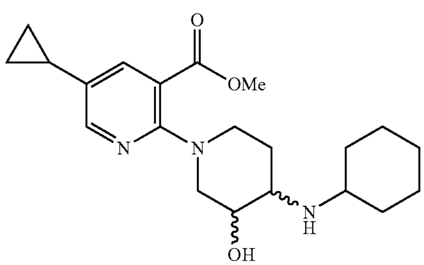 [SMILES: COC(=O)c1cc(C2CC2)cnc1N1CCC(NC2CCCCC2)C(O)C1] | 17000 |
| 156 | 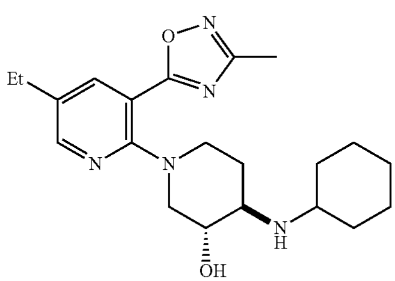 [SMILES: CCc1cnc(N2CC[C@@H](NC3CCCCC3)[C@H](O)C2)c(-c2nc(C)no2)c1] | 1000 |
| 157 | (trans-rac) | 37 |

TABLE I-continued
Compounds of the Invention
| Cpd. # | Structure | IC$_{50}$ nM (% inhib if other than 50%) |
|---|---|---|
| 158 | 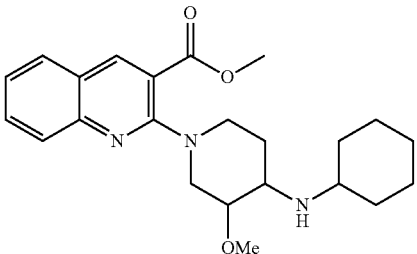 cis-rac | 431 |
| 159 | 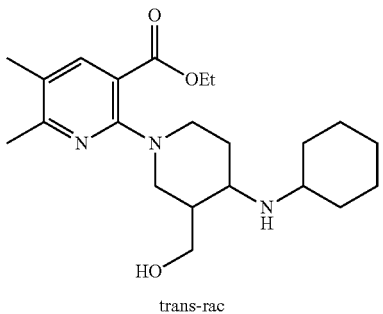 [SMILES: CCOC(=O)c1cc(C)c(C)nc1N1CCC(NC2CCCCC2)C(CO)C1] trans-rac | 35 |
| 160 | 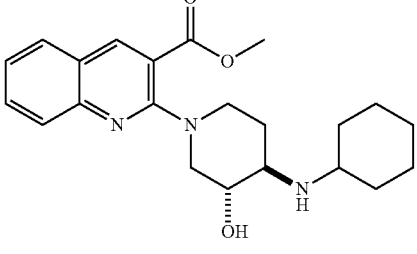 | 209 |
| 161 | 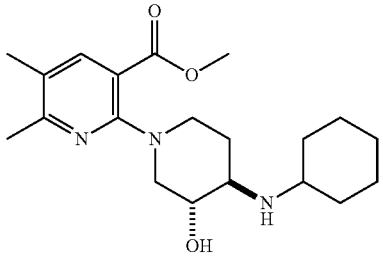 [SMILES: COC(=O)c1cc(C)c(C)nc1N1CC[C@@H](NC2CCCCC2)[C@H](O)C1] | 157 |
| 162 | 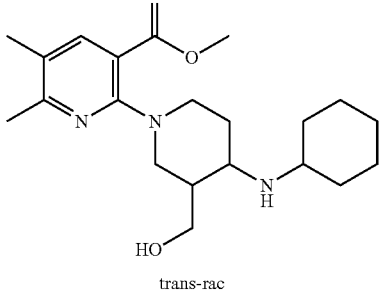 trans-rac | 1400 |

TABLE I-continued
Compounds of the Invention
| Cpd. # | Structure | IC$_{50}$ nM (% inhib if other than 50%) |
|---|---|---|
| 163 | 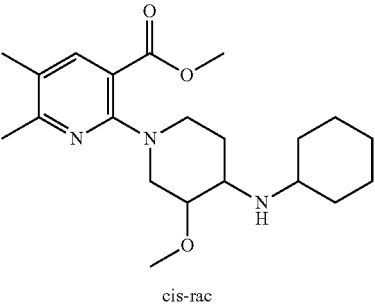 [SMILES: COC(=O)c1cc(C)c(C)nc1N1CCC(NC2CCCCC2)C(OC)C1]<br>cis-rac | 915 |
| 164 | 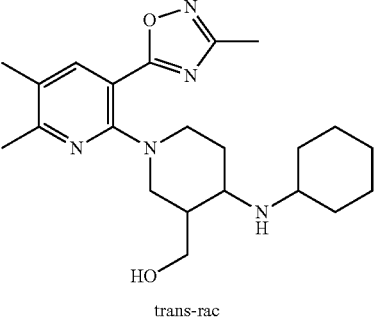 [SMILES: Cc1noc(-c2cc(C)c(C)nc2N2CCC(NC3CCCCC3)C(CO)C2)n1]<br>trans-rac | 62 |
| 165 | 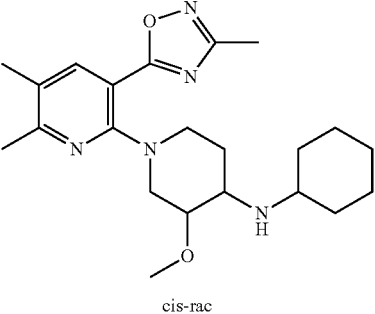 [SMILES: COC1CN(c2nc(C)c(C)cc2-c2nc(C)no2)CCC1NC1CCCCC1]<br>cis-rac | 19 |
| 166 | 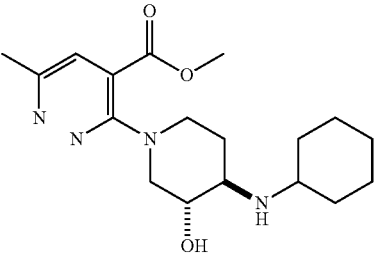 [SMILES: COC(=O)C(/C=C(/C)N)=C(/N)N1CC[C@@H](NC2CCCCC2)[C@H](O)C1] | 32 |

TABLE I-continued
Compounds of the Invention
| Cpd. # | Structure | IC₅₀ nM (% inhib if other than 50%) |
|---|---|---|
| 167 | 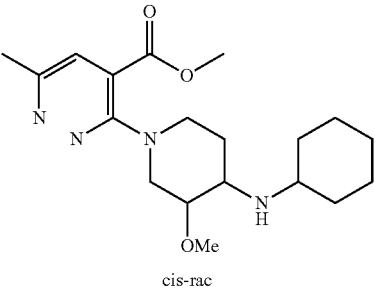 [SMILES: COC(=O)C(/C=C(/C)N)=C(/N)N1CCC(NC2CCCCC2)C(OC)C1] cis-rac | 19 |
| 168 | 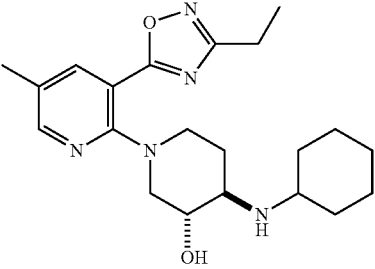 [SMILES: CCc1noc(-c2cc(C)cnc2N2CC[C@@H](NC3CCCCC3)[C@H](O)C2)n1] | 7000 |
| 169 | 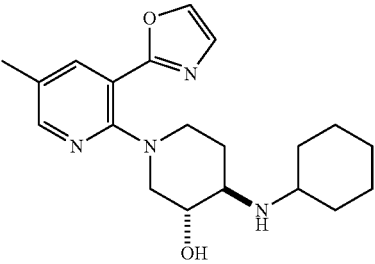 [SMILES: Cc1cnc(N2CC[C@@H](NC3CCCCC3)[C@H](O)C2)c(-c2ncco2)c1] | 2500 |
| 170 | 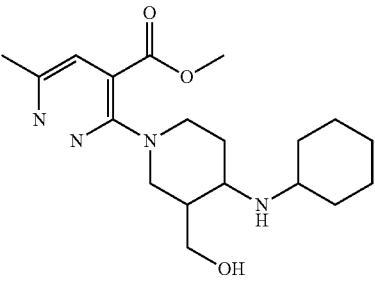 trans-rac | 11.7 |
| 171 | 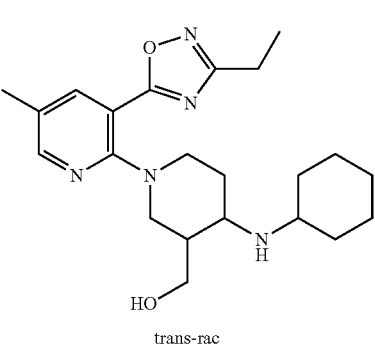 [SMILES: CCc1noc(-c2cc(C)cnc2N2CCC(NC3CCCCC3)C(CO)C2)n1] trans-rac | 1100 |

TABLE I-continued

Compounds of the Invention

| Cpd. # | Structure | IC$_{50}$ nM (% inhib if other than 50%) |
|---|---|---|
| 172 | 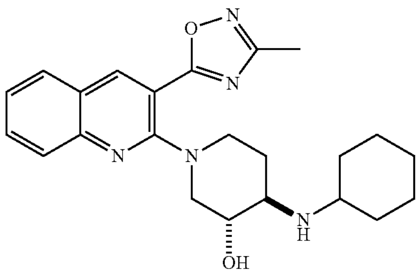 [SMILES: Cc1noc(-c2cc3ccccc3nc2N2CC[C@@H](NC3CCCCC3)[C@H](O)C2)n1] | 22 |
| 173 | 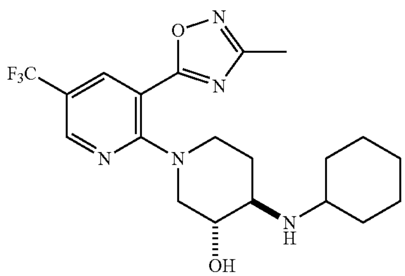 [SMILES: Cc1noc(-c2cc(C(F)(F)F)cnc2N2CC[C@@H](NC3CCCCC3)[C@H](O)C2)n1] | 1200 |
| 174 | cis-rac | 180 |
| 175 | 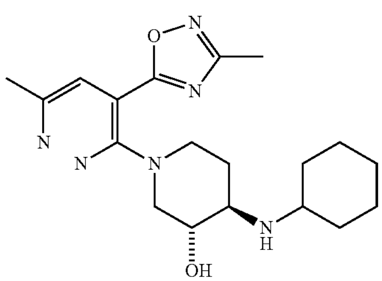 [SMILES: C/C(N)=C/C(=C(\N)N1CC[C@@H](NC2CCCCC2)[C@H](O)C1)c1nc(C)no1] | 46 |
| C67 | 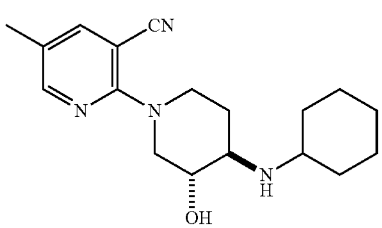 [SMILES: Cc1cnc(N2CC[C@@H](NC3CCCCC3)[C@H](O)C2)c(C#N)c1] | 37000 |

TABLE I-continued
Compounds of the Invention
| Cpd. # | Structure | IC$_{50}$ nM (% inhib if other than 50%) |
|---|---|---|
| C68 | 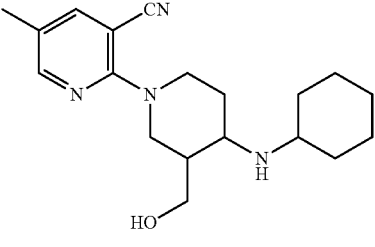<br>trans-rac | >20000 |
| 176 | 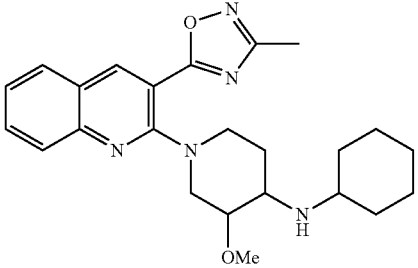<br>cis-rac | 28 |
| 177 | 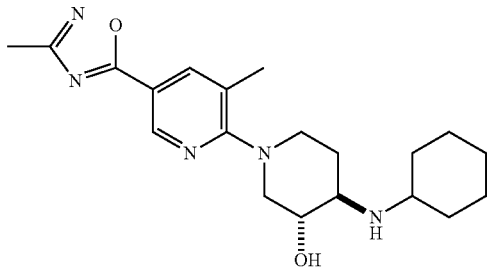 [SMILES: CC(=N)/N=C(\O)c1cnc(N2CC[C@@H](NC3CCCCC3)[C@H](O)C2)c(C)c1] | >20 |
| 178 | 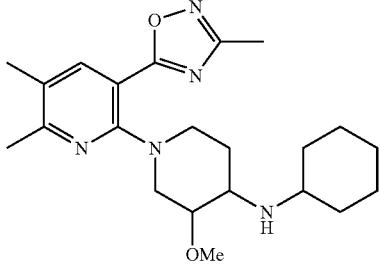<br>trans-rac | 483 |
| 179 | 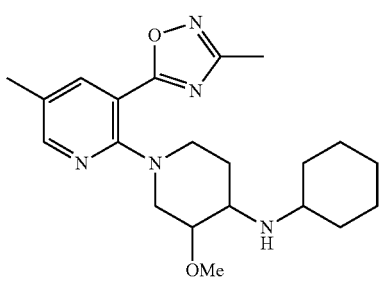<br>cis-rac | 253 |

TABLE I-continued
Compounds of the Invention
| Cpd. # | Structure | IC$_{50}$ nM (% inhib if other than 50%) |
|---|---|---|
| 180 | 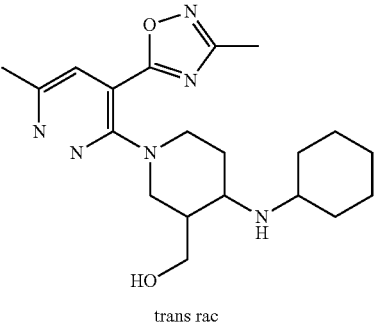 [SMILES: C/C(N)=C/C(=C(\N)N1CCC(NC2CCCCC2)C(CO)C1)c1nc(C)no1] trans rac | 7 |
| 181 | 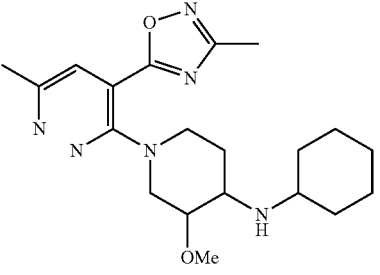 trans rac | 30 |
| 182 | 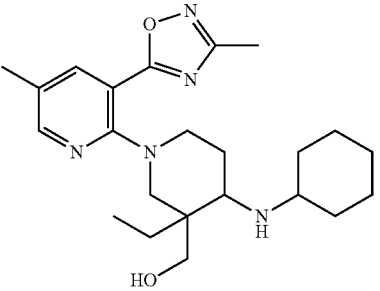 rac | 76 |
| 183 | 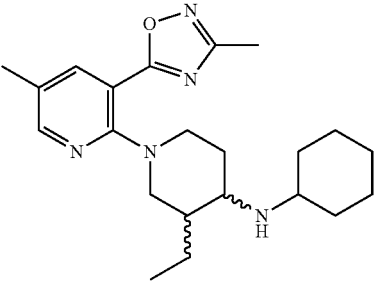 [SMILES: CCC1CN(c2ncc(C)cc2-c2nc(C)no2)CCC1NC1CCCCC1] | 280 |

TABLE I-continued
Compounds of the Invention
| Cpd. # | Structure | IC$_{50}$ nM (% inhib if other than 50%) |
|---|---|---|
| 184 | 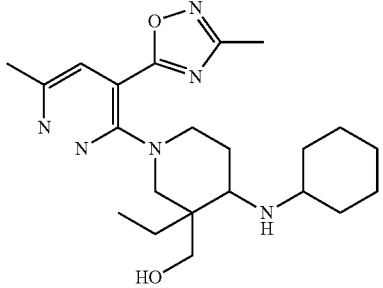 rac | 19 |
| 185 | 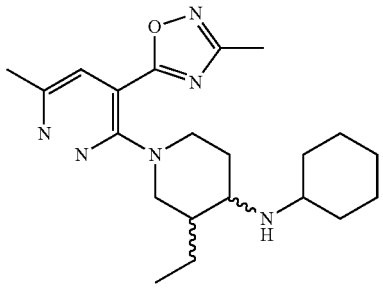 [SMILES: CCC1CN(/C(N)=C(/C=C(/C)N)c2nc(C)no2)CCC1NC1CCCCC1] | 24 |
| 186 | 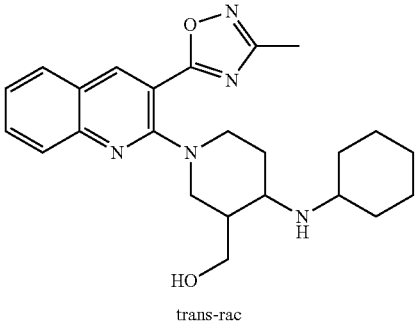 [SMILES: Cc1noc(-c2cc3ccccc3nc2N2CCC(NC3CCCCC3)C(CO)C2)n1] trans-rac | 5 |
| 187 | 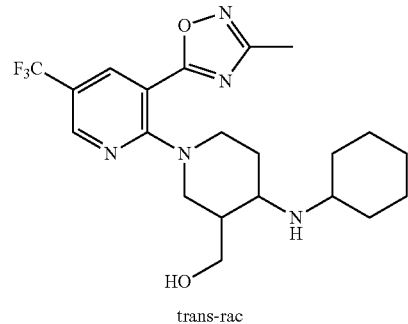 [SMILES: Cc1noc(-c2cc(C(F)(F)F)cnc2N2CCC(NC3CCCCC3)C(CO)C2)n1] trans-rac | 341 |

TABLE I-continued

Compounds of the Invention

| Cpd. # | Structure | IC$_{50}$ nM (% inhib if other than 50%) |
|---|---|---|
| 188 | 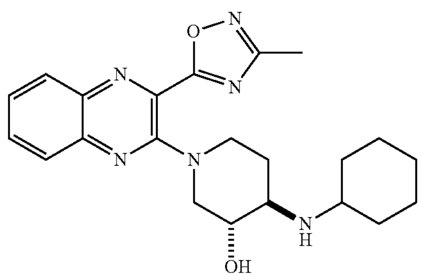 [SMILES: Cc1noc(-c2nc3ccccc3nc2N2CC[C@@H](NC3CCCCC3)[C@H](O)C2)n1] | 187 |
| 189 | trans-rac | 125 |
| 190 | cis-rac | 57 |
| 191 | trans-rac | 420 |

TABLE I-continued

Compounds of the Invention

| Cpd. # | Structure | IC$_{50}$ nM (% inhib if other than 50%) |
|---|---|---|
| 192 | 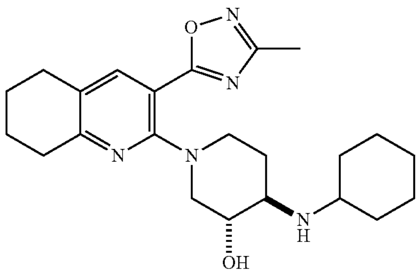 [SMILES: Cc1noc(-c2cc3c(nc2N2CC[C@@H](NC4CCCCC4)[C@H](O)C2)CCCC3)n1] | 199 |
| 193 | cis-rac | 729 |
| 194 | 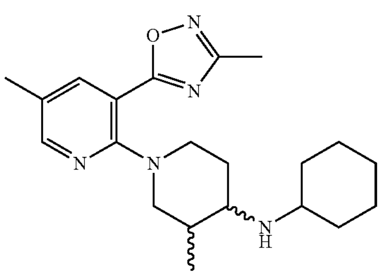 [SMILES: Cc1cnc(N2CCC(NC3CCCCC3)C(C)C2)c(-c2nc(C)no2)c1] | 180 |
| 195 | trans-rac | 700 |

TABLE I-continued
Compounds of the Invention
| Cpd. # | Structure | IC$_{50}$ nM (% inhib if other than 50%) |
|---|---|---|
| 196 | 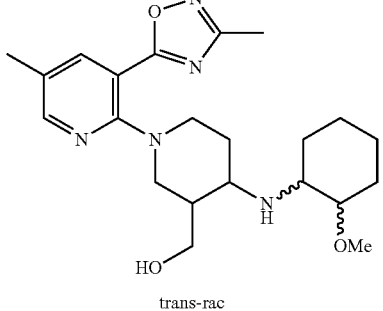 trans-rac | 414 |
| 197 | 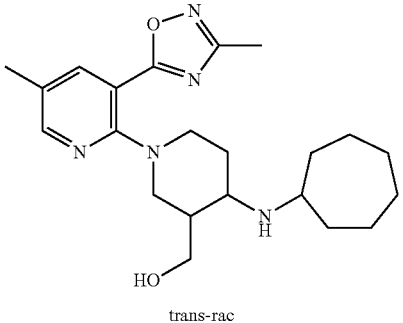 [SMILES: Cc1cnc(N2CCC(NC3CCCCCC3)C(CO)C2)c(-c2nc(C)no2)c1] trans-rac | 85 |
| 198 | 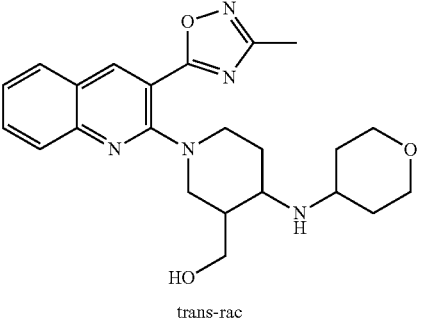 [SMILES: Cc1noc(-c2cc3ccccc3nc2N2CCC(NC3CCOCC3)C(CO)C2)n1] trans-rac | 98 |
| 199 | 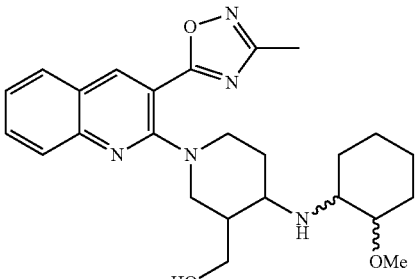 trans-rac | 59 |

TABLE I-continued
Compounds of the Invention
| Cpd. # | Structure | IC$_{50}$ nM (% inhib if other than 50%) |
|---|---|---|
| 200 | 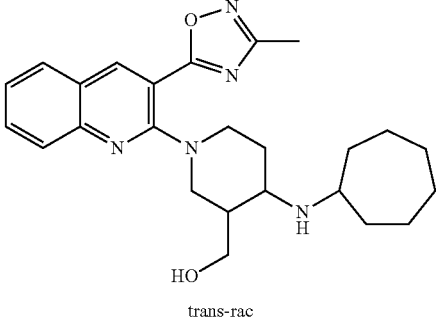 [SMILES: Cc1noc(-c2cc3ccccc3nc2N2CCC(NC3CCCCCC3)C(CO)C2)n1]<br>trans-rac | 14 |
| 201 | 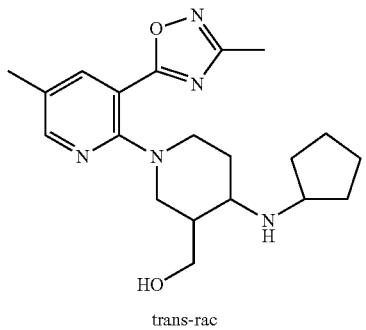 [SMILES: Cc1cnc(N2CCC(NC3CCCC3)C(CO)C2)c(-c2nc(C)no2)c1]<br>trans-rac | 116 |
| 202 | 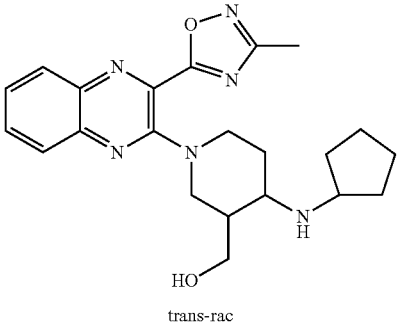 [SMILES: Cc1noc(-c2nc3ccccc3nc2N2CCC(NC3CCCC3)C(CO)C2)n1]<br>trans-rac | 187 |
| 203 | 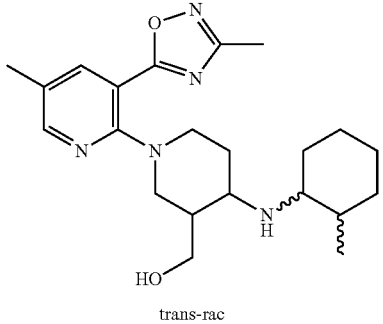 [SMILES: Cc1cnc(N2CCC(NC3CCCCC3C)C(CO)C2)c(-c2nc(C)no2)c1]<br>trans-rac | 132 |

TABLE I-continued

Compounds of the Invention

| Cpd. # | Structure | IC$_{50}$ nM (% inhib if other than 50%) |
|---|---|---|
| 204 | | 52 |
| 205 | trans-rac | 17 |
| 206 | trans-rac | 33 |
| 207 | | 276 |

TABLE I-continued
Compounds of the Invention
| Cpd. # | Structure | IC$_{50}$ nM (% inhib if other than 50%) |
|---|---|---|
| 208 | 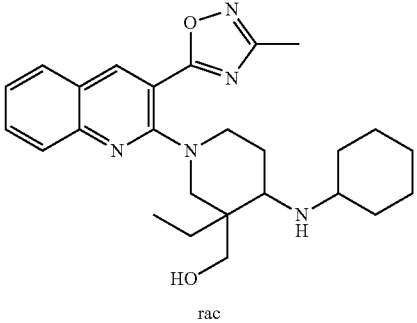 [SMILES: CCC1(CO)CN(c2nc3ccccc3cc2-c2nc(C)no2)CCC1NC1CCCCC1] rac | 76 |
| 209 | 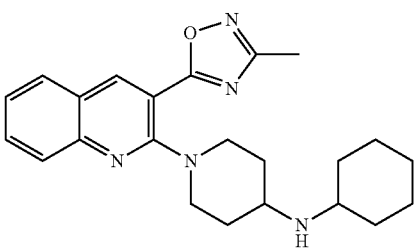 [SMILES: Cc1noc(-c2cc3ccccc3nc2N2CCC(NC3CCCCC3)CC2)n1] | 18 |
| 210 | 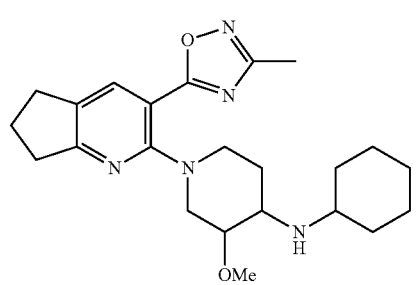 cis-rac | 72 |
| 211 | 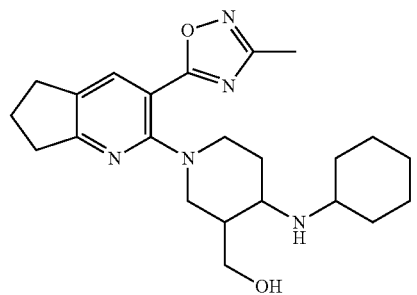 trans-rac | 74 |

127
128

TABLE I-continued

Compounds of the Invention

| Cpd. # | Structure | IC$_{50}$ nM (% inhib if other than 50%) |
|---|---|---|
| 212 | 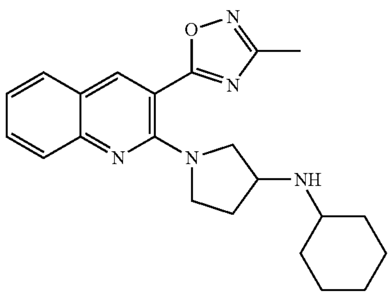 [SMILES: Cc1noc(-c2cc3ccccc3nc2N2CCC(NC3CCCCC3)C2)n1] | 267 |
| 213 | 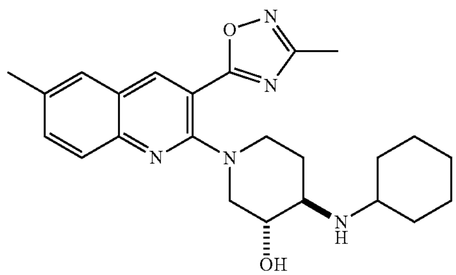 [SMILES: Cc1ccc2nc(N3CC[C@@H](NC4CCCCC4)[C@H](O)C3)c(-c3nc(C)no3)cc2c1] | 8.5 |
| 214 | cis-rac | 3 |
| 215 | trans-rac | 3 |
| 216 | trans-rac | 4500 |

TABLE I-continued
Compounds of the Invention
| Cpd. # | Structure | IC$_{50}$ nM (% inhib if other than 50%) |
|---|---|---|
| 217 | 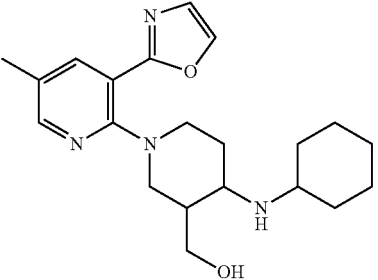 trans-rac | 361 |
| 218 | 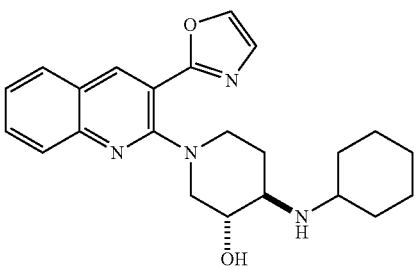 [SMILES: O[C@@H]1CN(c2nc3ccccc3cc2-c2ncco2)CC[C@H]1NC1CCCCC1] | 475 |
| C69 | 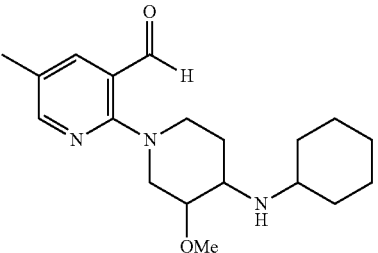 cis-rac | 30000 |
| C70 | 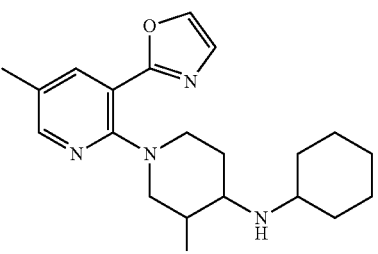 cis-rac | 17000 |
| 219 | 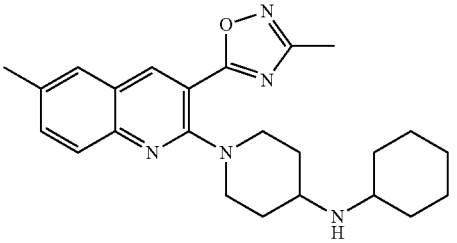 | 3.5 |

TABLE I-continued
Compounds of the Invention
| Cpd. # | Structure | IC$_{50}$ nM (% inhib if other than 50%) |
|---|---|---|
| 220 | 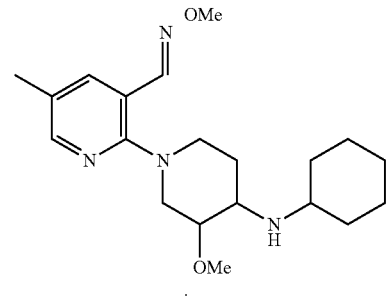 cis-rac | 101 |
| 221 | 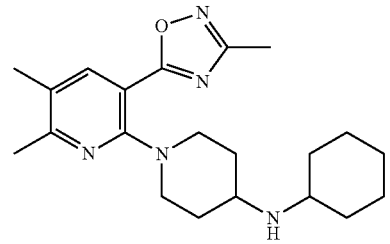 [SMILES: Cc1noc(-c2cc(C)c(C)nc2N2CCC(NC3CCCCC3)CC2)n1] | 24 |
| 222 | 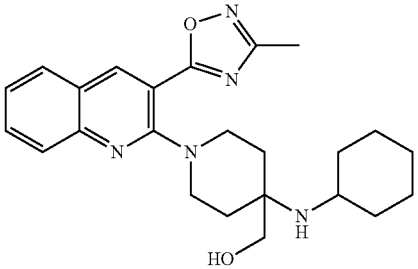 [SMILES: Cc1noc(-c2cc3ccccc3nc2N2CCC(CO)(NC3CCCCC3)CC2)n1] | 163 |
| 223 | 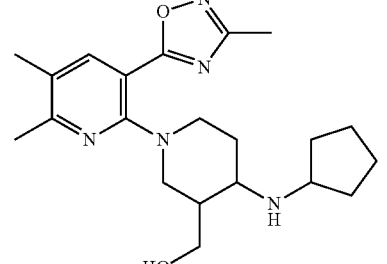 trans-rac | 13 |
| 224 | 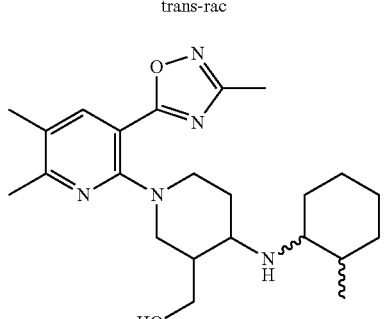 trans-rac | 17 |

TABLE I-continued
Compounds of the Invention
| Cpd. # | Structure | IC$_{50}$ nM (% inhib if other than 50%) |
|---|---|---|
| 225 | 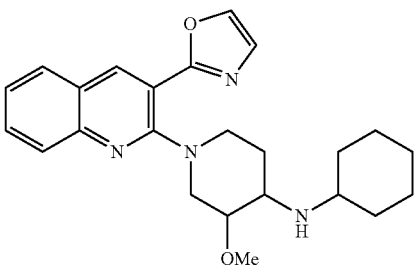 cis-rac | 70 |
| 226 | 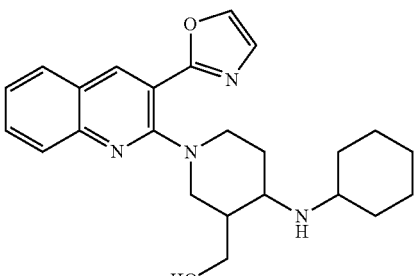 trans-rac | 107 |
| 227 | 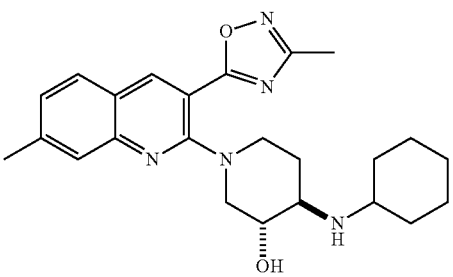 [SMILES: Cc1ccc2cc(-c3nc(C)no3)c(N3CC[C@@H](NC4CCCCC4)[C@H](O)C3)nc2c1] | 7 |
| 228 | 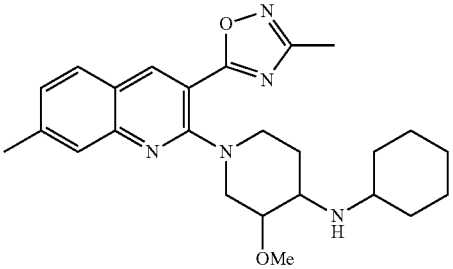 cis-rac | 21 |

TABLE I-continued
Compounds of the Invention
| Cpd. # | Structure | IC$_{50}$ nM (% inhib if other than 50%) |
|---|---|---|
| 229 | 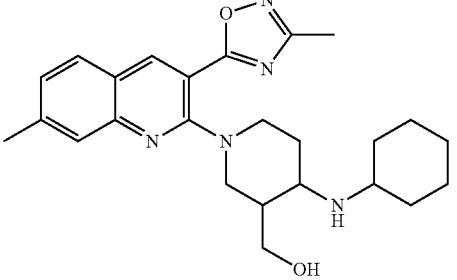 trans-rac | 5 |
| 230 | 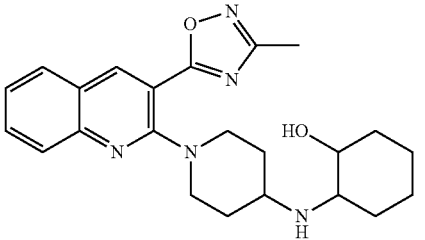 trans-rac | 9 |
| 231 | 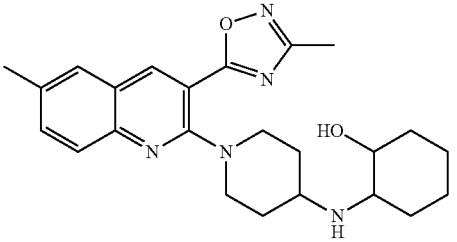 trans-rac | 0.86 |
| 232 | 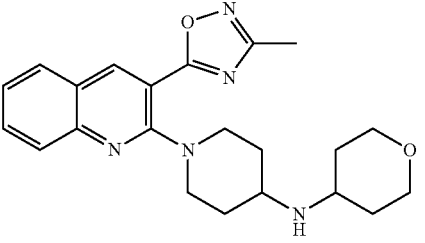 [SMILES: Cc1noc(-c2cc3ccccc3nc2N2CCC(NC3CCOCC3)CC2)n1] | 8 |
| 233 | 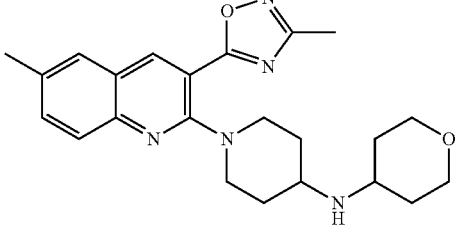 | 2 |

137
138
TABLE I-continued
Compounds of the Invention
| Cpd. # | Structure | IC$_{50}$ nM (% inhib if other than 50%) |
|---|---|---|
| 234 | 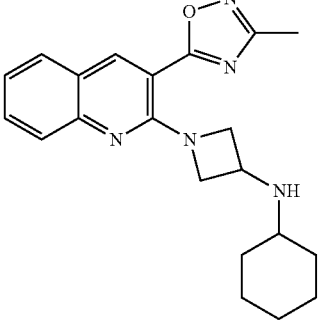 | 596 |
| 235 | 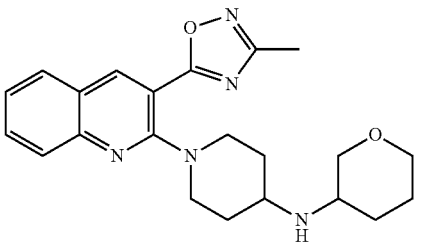 | 4 |
| 236 | 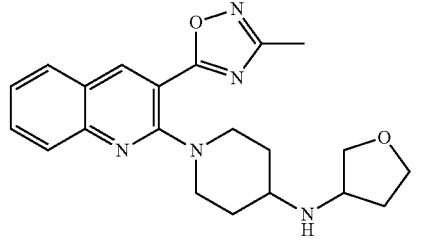 [SMILES: Cc1noc(-c2cc3ccccc3nc2N2CCC(NC3CCOC3)CC2)n1] | 20 |
| 237 | 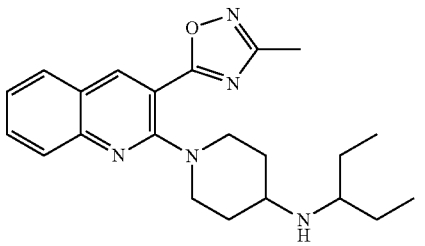 [SMILES: CCC(CC)NC1CCN(c2nc3ccccc3cc2-c2nc(C)no2)CC1] | 8 |
| 238 | 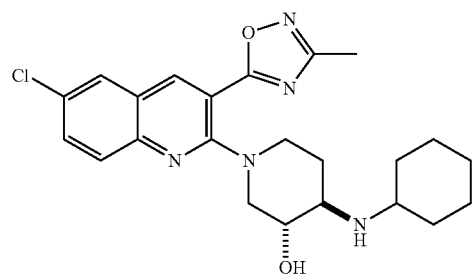 [SMILES: Cc1noc(-c2cc3cc(Cl)ccc3nc2N2CC[C@@H](NC3CCCCC3)[C@H](O)C2)n1] | 38 |

TABLE I-continued
Compounds of the Invention
| Cpd. # | Structure | IC$_{50}$ nM (% inhib if other than 50%) |
|---|---|---|
| 239 | 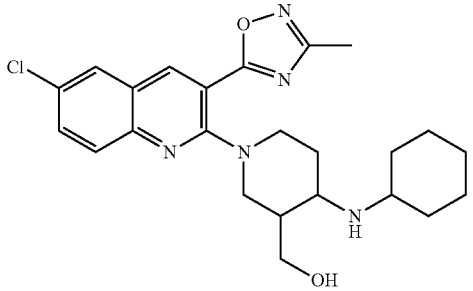 trans-rac | 16 |
| 240 | 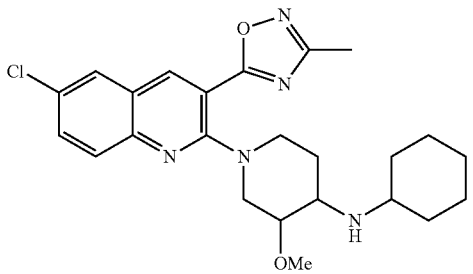 cis-rac | 14 |
| 241 | 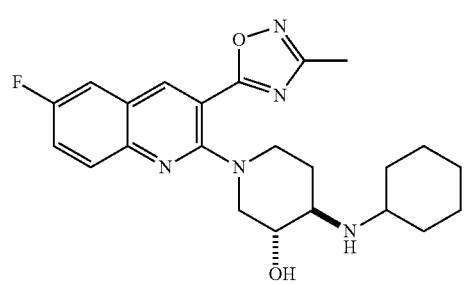 [SMILES: Cc1noc(-c2cc3cc(F)ccc3nc2N2CC[C@@H](NC3CCCCC3)[C@H](O)C2)n1] | 59 |
| 242 | 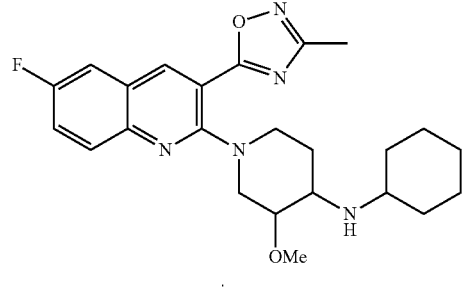 cis-rac | 26 |

TABLE I-continued
Compounds of the Invention
| Cpd. # | Structure | IC$_{50}$ nM (% inhib if other than 50%) |
|---|---|---|
| 243 | 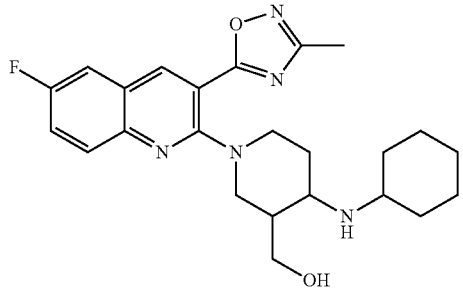<br>trans-rac | 22 |
| 244 | 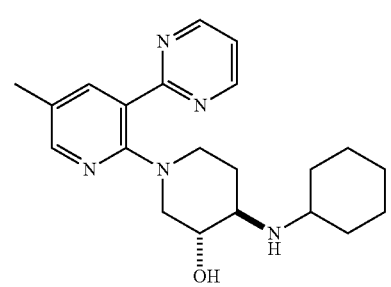 [SMILES: Cc1cnc(N2CC[C@@H](NC3CCCCC3)[C@H](O)C2)c(-c2ncccn2)c1] | 566 |
| 245 | 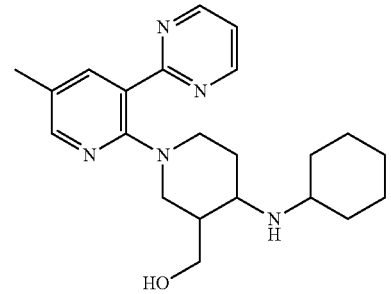<br>trans-rac | 79 |
| 246 | 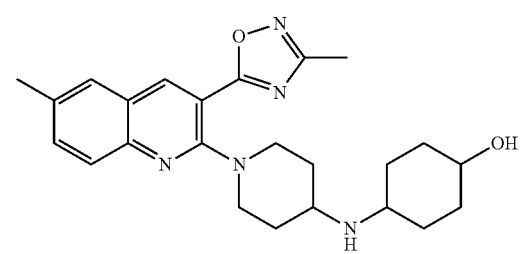<br>trans-rac | 51 |
| 247 | 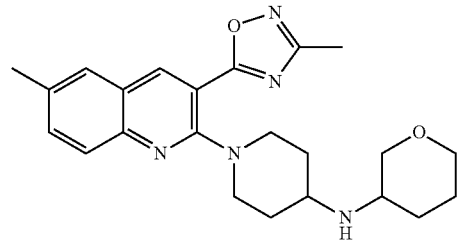 | 4 |

TABLE I-continued

Compounds of the Invention

| Cpd. # | Structure | IC$_{50}$ nM (% inhib if other than 50%) |
|---|---|---|
| 248 | (6-methylquinoline with 3-methyl-1,2,4-oxadiazole at C3; C2 linked to piperidine-N; piperidine-4-NH to 2-hydroxycyclohexyl) | 11 |
| 249 | (6-methylquinoline with 3-methyl-1,2,4-oxadiazole at C3; C2 linked to 3-methoxypiperidine-N; piperidine-4-NH to 2-fluorocyclohexyl) cis-rac | 9 |
| 250 | (6-methylquinoline with 3-methyl-1,2,4-oxadiazole at C3; C2 linked to piperidine-N; piperidine-4-NH to 2-fluorocyclohexyl) | 8 |
| 251 | (5-fluoroquinoline with 3-methyl-1,2,4-oxadiazole at C3; C2 linked to 3-hydroxypiperidine-N; piperidine-4-NH to cyclohexyl) | 11 |
| 252 | (5-fluoroquinoline with 3-methyl-1,2,4-oxadiazole at C3; C2 linked to 3-methoxypiperidine-N; piperidine-4-NH to cyclohexyl) cis-rac | 12 |

TABLE I-continued
Compounds of the Invention
| Cpd. # | Structure | IC$_{50}$ nM (% inhib if other than 50%) |
|---|---|---|
| 253 | 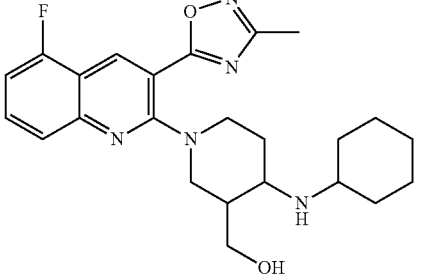<br>trans-rac | 10 |
| 254 | 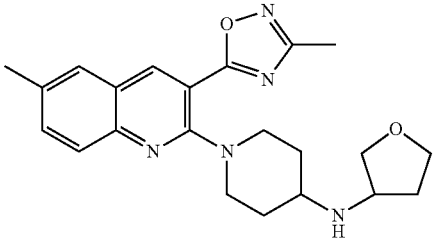 | 8 |
| 255 | 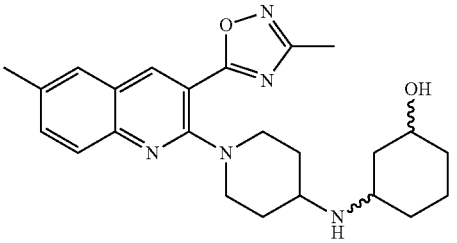 [SMILES: Cc1ccc2nc(N3CCC(NC4CCCC(O)C4)CC3)c(-c3nc(C)no3)cc2c1] | 10 |
| 256 | 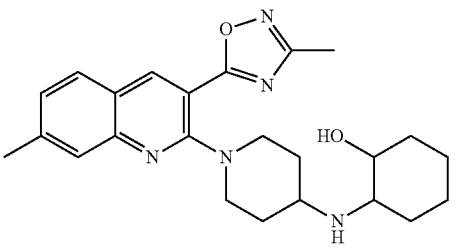<br>trans-rac | 631 |
| 257 | 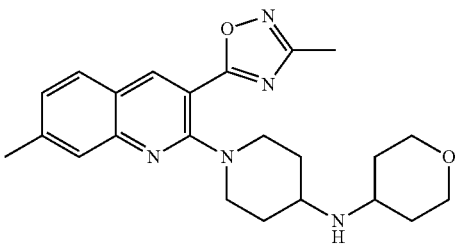 [SMILES: Cc1ccc2cc(-c3nc(C)no3)c(N3CCC(NC4CCOCC4)CC3)nc2c1] | 930 |

TABLE I-continued

Compounds of the Invention

| Cpd. # | Structure | IC$_{50}$ nM (% inhib if other than 50%) |
|---|---|---|
| C71 | 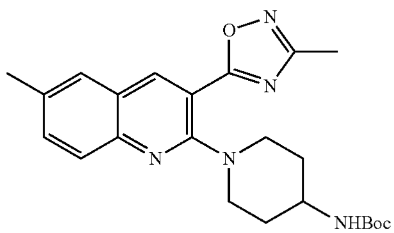 [SMILES: Cc1ccc2nc(N3CCC(NC(=O)OC(C)(C)C)CC3)c(-c3nc(C)no3)cc2c1] | NA |
| 258 | cis-rac | 7160 |
| 259 | cis-rac | 372 |
| C72 | 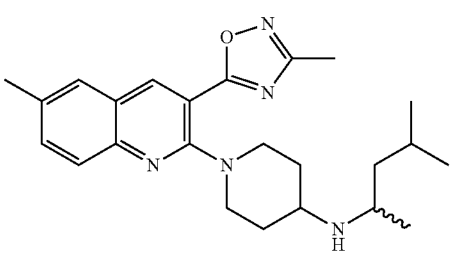 [SMILES: Cc1ccc2nc(N3CCC(NC(C)CC(C)C)CC3)c(-c3nc(C)no3)cc2c1] | NA |
| 260 | 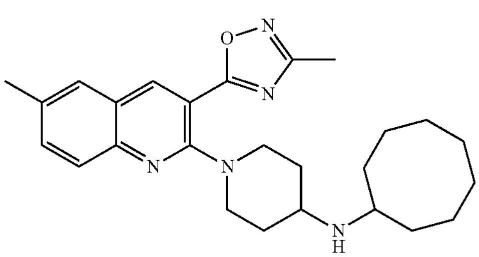 [SMILES: Cc1ccc2nc(N3CCC(NC4CCCCCCC4)CC3)c(-c3nc(C)no3)cc2c1] | 261 |

TABLE I-continued
Compounds of the Invention
| Cpd. # | Structure | IC$_{50}$ nM (% inhib if other than 50%) |
|---|---|---|
| 261 | 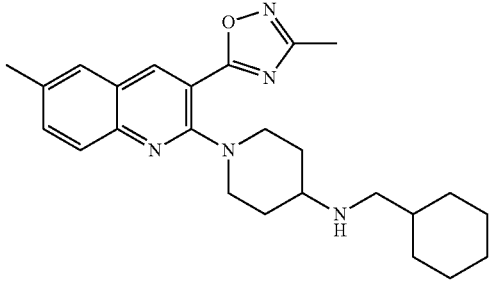 [SMILES: Cc1ccc2nc(N3CCC(NCC4CCCCC4)CC3)c(-c3nc(C)no3)cc2c1] | 1470 |
| C73 | 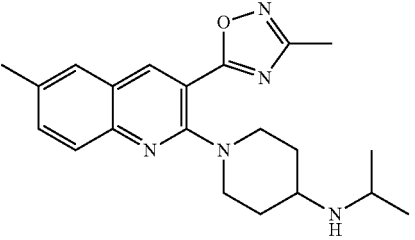 [SMILES: Cc1ccc2nc(N3CCC(NC(C)C)CC3)c(-c3nc(C)no3)cc2c1] | NA |
| C74 | 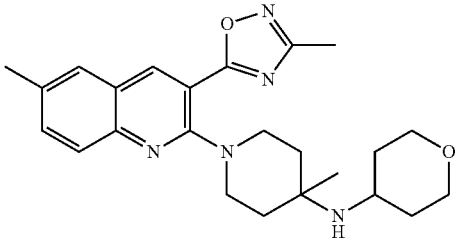 [SMILES: Cc1ccc2nc(N3CCC(C)(NC4CCOCC4)CC3)c(-c3nc(C)no3)cc2c1] | NA |
| C75 | 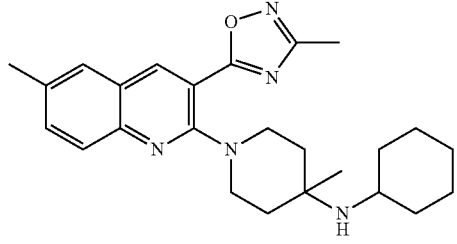 [SMILES: Cc1ccc2nc(N3CCC(C)(NC4CCCCC4)CC3)c(-c3nc(C)no3)cc2c1] | NA |
| 262 | 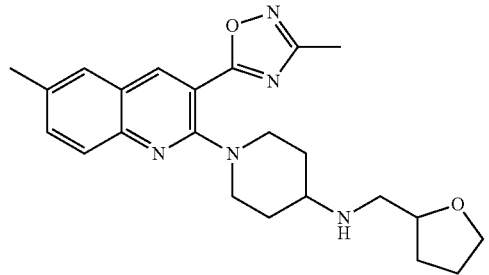 [SMILES: Cc1ccc2nc(N3CCC(NCC4CCCO4)CC3)c(-c3nc(C)no3)cc2c1] | 60 |

TABLE I-continued
Compounds of the Invention
| Cpd. # | Structure | IC$_{50}$ nM (% inhib if other than 50%) |
|---|---|---|
| C76 | 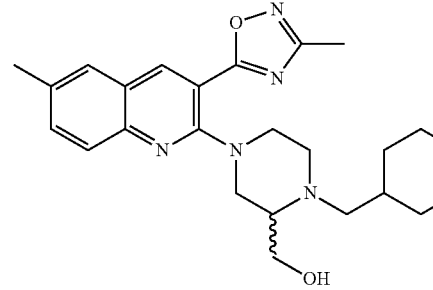 | NA |
| C77 | 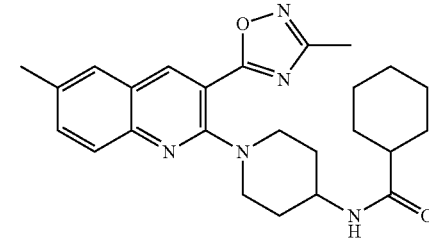 | NA |
| C78 | 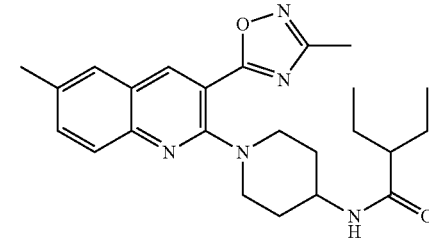 | NA |
| C79 | 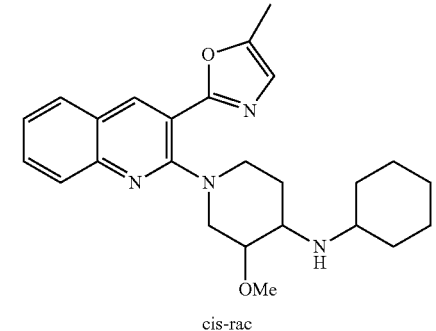 [SMILES: COC1CN(c2nc3ccccc3cc2-c2ncc(C)o2)CCC1NC1CCCCC1]<br>cis-rac | NA |
| C80 | 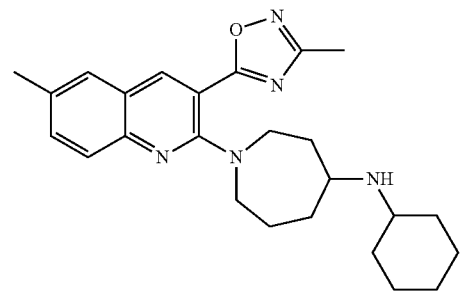 [SMILES: Cc1ccc2nc(N3CCCC(NC4CCCCC4)CC3)c(-c3nc(C)no3)cc2c1] | NA |

TABLE I-continued
Compounds of the Invention
| Cpd. # | Structure | IC$_{50}$ nM (% inhib if other than 50%) |
|---|---|---|
| C81 | 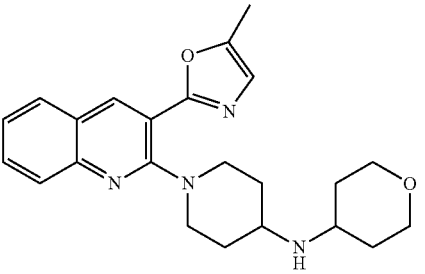 [SMILES: Cc1cnc(-c2cc3ccccc3nc2N2CCC(NC3CCOCC3)CC2)o1] | NA |
| C82 | 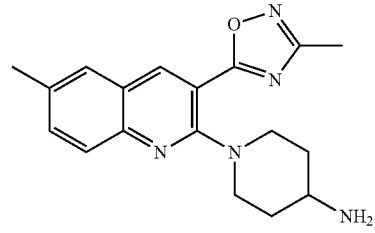 [SMILES: Cc1ccc2nc(N3CCC(N)CC3)c(-c3nc(C)no3)cc2c1] | NA |
| C83 | 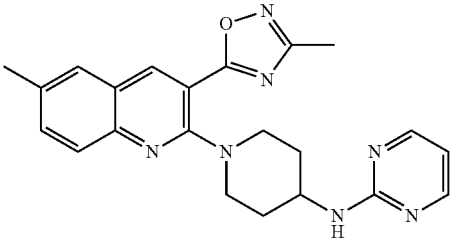 [SMILES: Cc1ccc2nc(N3CCC(Nc4ncccn4)CC3)c(-c3nc(C)no3)cc2c1] | 47000 |
| 263 | 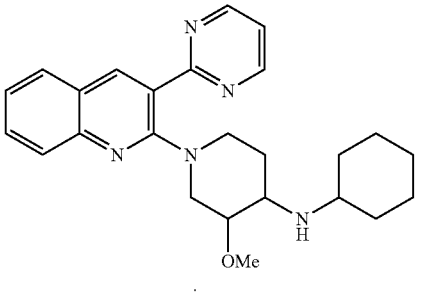 cis-rac | 1770 |
| 264 | 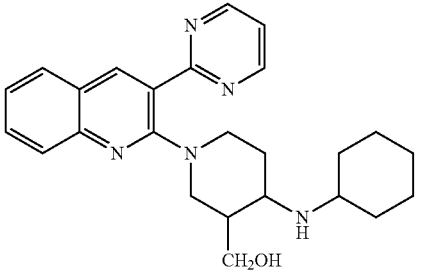 trans-rac | 56 |

TABLE I-continued
Compounds of the Invention
| Cpd. # | Structure | IC$_{50}$ nM (% inhib if other than 50%) |
|---|---|---|
| 265 | 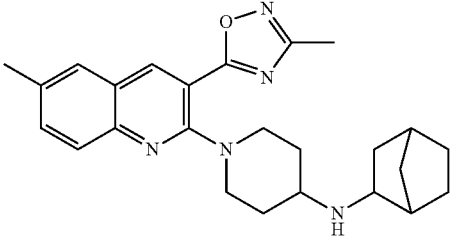 [SMILES: Cc1ccc2nc(N3CCC(NC4CC5CCC4C5)CC3)c(-c3nc(C)no3)cc2c1] | 49 |
| 266 | 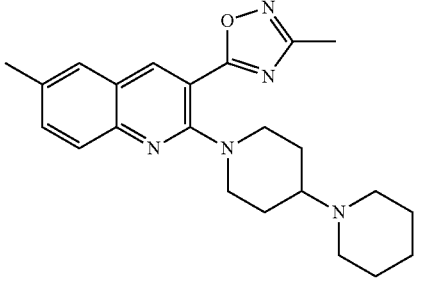 [SMILES: Cc1ccc2nc(N3CCC(N4CCCCC4)CC3)c(-c3nc(C)no3)cc2c1] | 1740 |
| 267 | 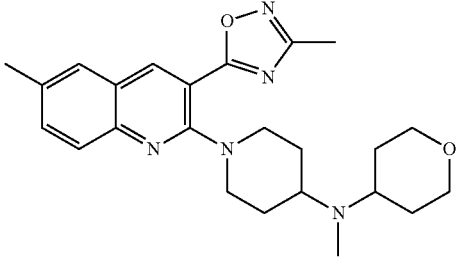 [SMILES: Cc1ccc2nc(N3CCC(N(C)C4CCOCC4)CC3)c(-c3nc(C)no3)cc2c1] | 180 |
| C84 | 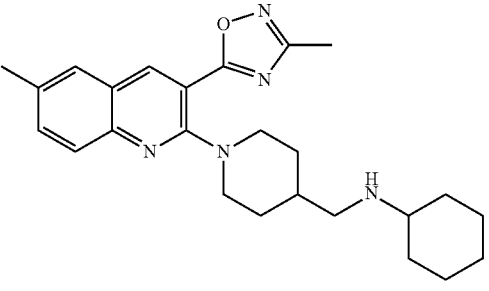 [SMILES: Cc1ccc2nc(N3CCC(CNC4CCCCC4)CC3)c(-c3nc(C)no3)cc2c1] | NA |
| 268 | 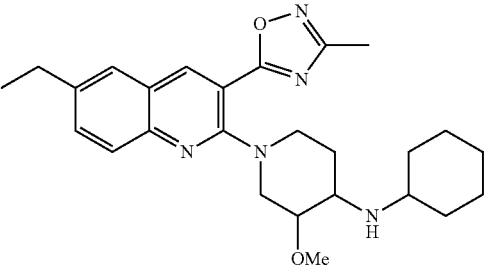 cis-rac | 37 |

TABLE I-continued

Compounds of the Invention

| Cpd. # | Structure | IC$_{50}$ nM (% inhib if other than 50%) |
|---|---|---|
| 269 | trans-rac | 30 |
| 270 | 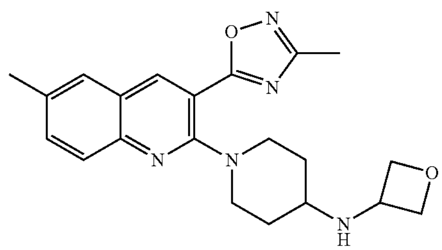 [SMILES: Cc1ccc2nc(N3CCC(NC4COC4)CC3)c(-c3nc(C)no3)cc2c1] | 4470 |
| 271 | 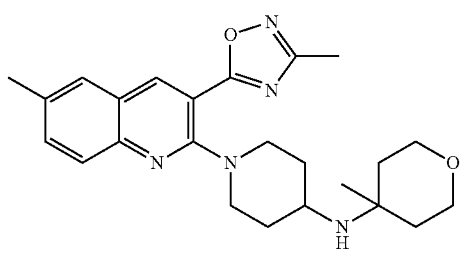 | 419 |
| C85 | 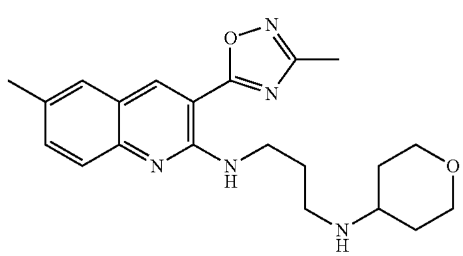 [SMILES: Cc1ccc2nc(NCCCNC3CCOCC3)c(-c3nc(C)no3)cc2c1] | NA |
| C86 | 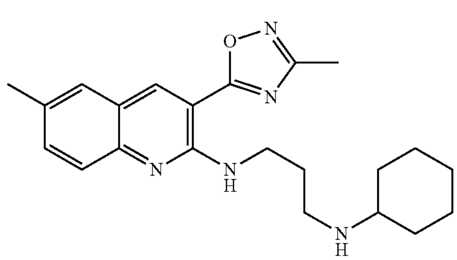 [SMILES: Cc1ccc2nc(NCCCNC3CCCCC3)c(-c3nc(C)no3)cc2c1] | NA |

TABLE I-continued

Compounds of the Invention

| Cpd. # | Structure | IC$_{50}$ nM (% inhib if other than 50%) |
|---|---|---|
| 272 | 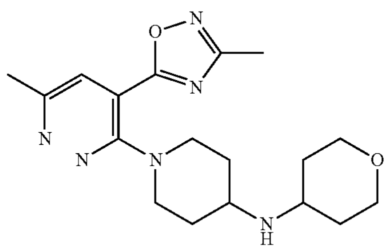 [SMILES: C/C(N)=C/C(=C(\N)N1CCC(NC2CCOCC2)CC1)c1nc(C)no1] | 8700 |
| 273 | cis-rac | 387 |
| C87 | 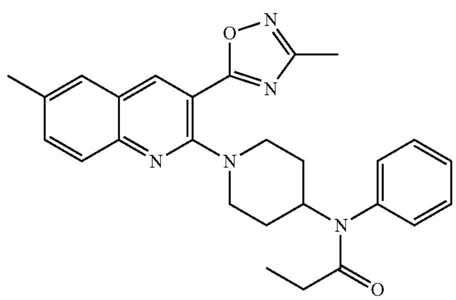 [SMILES: CCC(=O)N(c1ccccc1)C1CCN(c2nc3ccc(C)cc3cc2-c2nc(C)no2)CC1] | NA |
| 274 | 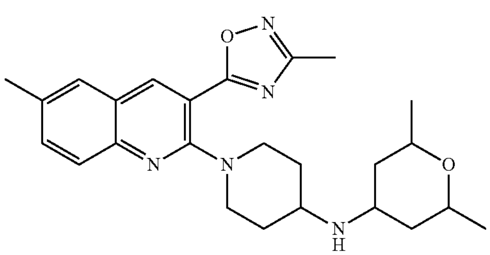 | 50 |
| C88 | 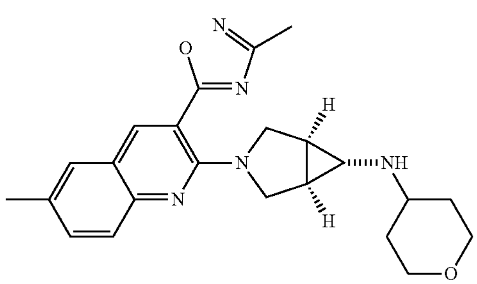 [SMILES: CC(=N)/N=C(\O)c1cc2cc(C)ccc2nc1N1C[C@@H]2[C@H](C1)[C@H]2NC1CCOCC1] | NA |

TABLE I-continued

Compounds of the Invention

| Cpd. # | Structure | IC$_{50}$ nM (% inhib if other than 50%) |
|---|---|---|
| 275 | 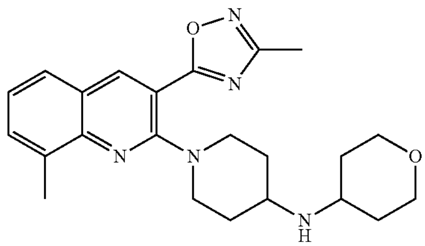 [SMILES: Cc1noc(-c2cc3cccc(C)c3nc2N2CCC(NC3CCOCC3)CC2)n1] | 98 |
| 276 | cis-rac | 18 |
| 277 | trans-rac | 9 |
| 278 | cis-rac | 4725 |
| 279 | cis-rac | 96 |

TABLE I-continued
Compounds of the Invention
| Cpd. # | Structure | IC$_{50}$ nM (% inhib if other than 50%) |
|---|---|---|
| C89 | 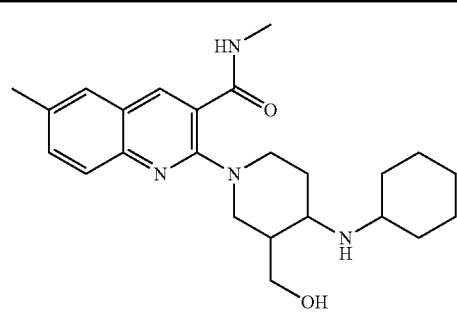 trans-rac | NA |
| 280 | 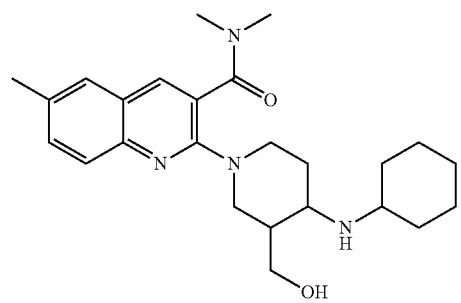 trans-rac | 99 |
| 281 | 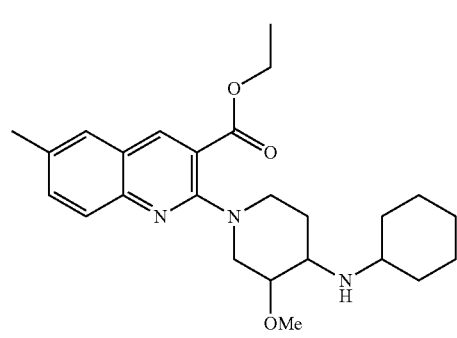 cis-rac | 30 |
| 282 | 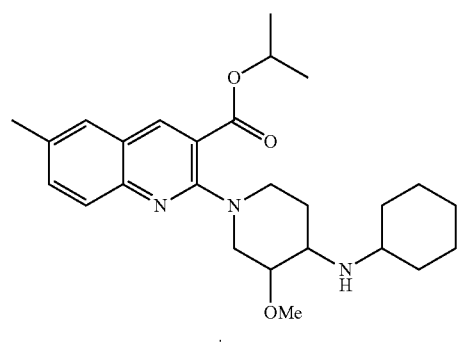 cis-rac | 38 |

TABLE I-continued

Compounds of the Invention

| Cpd. # | Structure | IC$_{50}$ nM (% inhib if other than 50%) |
|---|---|---|
| 283 | cis-rac | 4 |
| 284 | trans-rac | 20 |
| 285 | 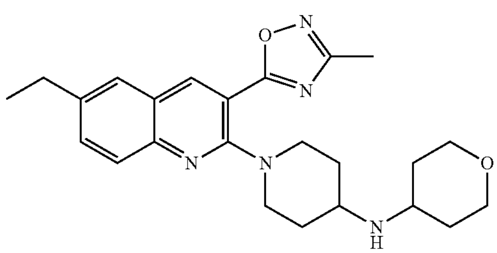 [SMILES: CCc1ccc2nc(N3CCC(NC4CCOCC4)CC3)c(-c3nc(C)no3)cc2c1] | 7 |
| 286 | 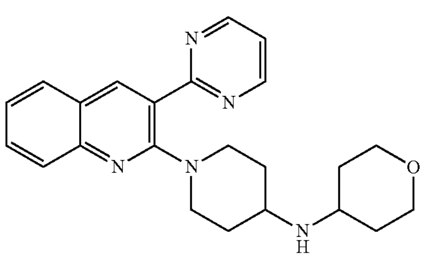 [SMILES: c1cnc(-c2cc3ccccc3nc2N2CCC(NC3CCOCC3)CC2)nc1] | 298 |
| 288 | trans-rac | 15 |

TABLE I-continued
Compounds of the Invention
| Cpd. # | Structure | IC$_{50}$ nM (% inhib if other than 50%) |
|---|---|---|
| 289 | 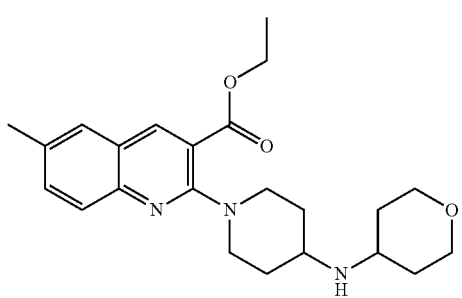 [SMILES: CCOC(=O)c1cc2cc(C)ccc2nc1N1CCC(NC2CCOCC2)CC1] | 184 |
| 290 | 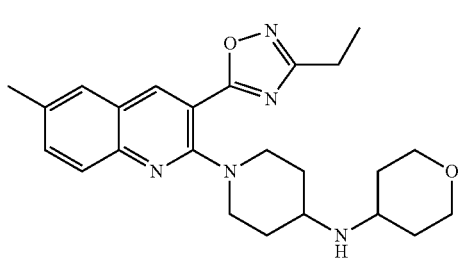 | 47 |
| 291 | 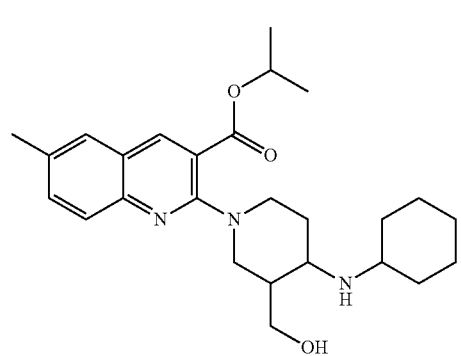 trans-rac | 18 |
| 292 | 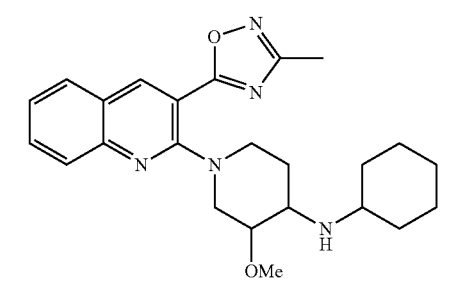 trans-rac | 33 |

TABLE I-continued
Compounds of the Invention
| Cpd. # | Structure | IC$_{50}$ nM (% inhib if other than 50%) |
|---|---|---|
| 293 | 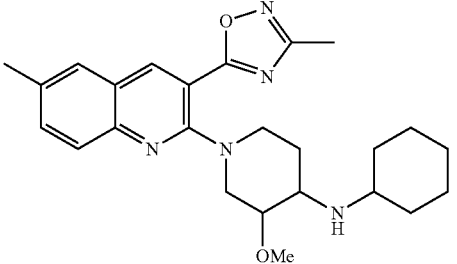<br>trans-rac | 20 |
| 294 | 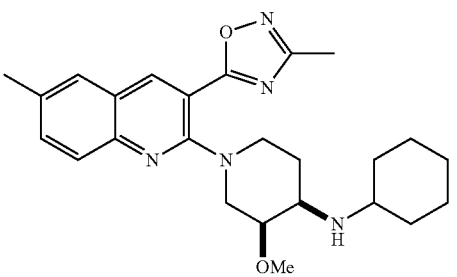 | 0.7 |
| 295 | 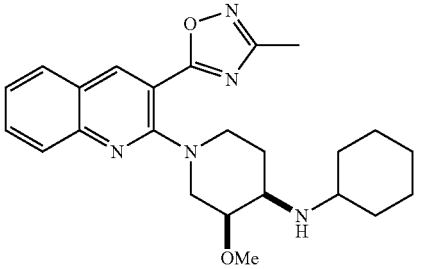 [SMILES: CO[C@H]1CN(c2nc3ccccc3cc2-c2nc(C)no2)CC[C@H]1NC1CCCCC1] | 2 |
| 296 | 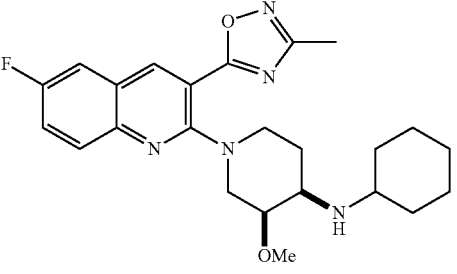 | 10 |
| 297 | 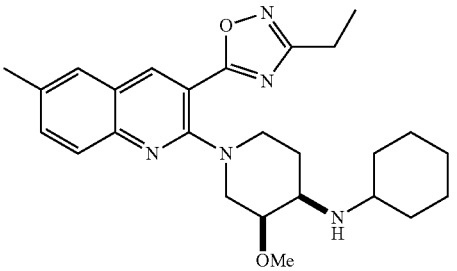 [SMILES: CCc1noc(-c2cc3cc(C)ccc3nc2N2CC[C@@H](NC3CCCCC3)[C@@H](OC)C2)n1] | 2 |

TABLE I-continued

Compounds of the Invention

| Cpd. # | Structure | IC$_{50}$ nM (% inhib if other than 50%) |
|---|---|---|
| 298 | 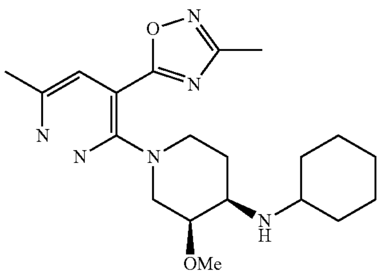 [SMILES: CO[C@H]1CN(/C(N)=C(/C=C(/C)N)c2nc(C)no2)CC[C@H]1NC1CCCCC1] | 3 |
| 299 | 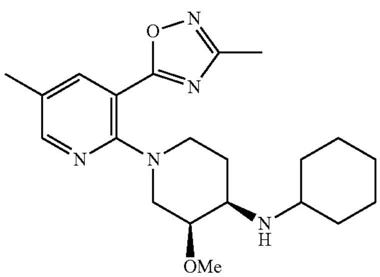 [SMILES: CO[C@H]1CN(c2ncc(C)cc2-c2nc(C)no2)CC[C@H]1NC1CCCCC1] | 25 |
| 300 | 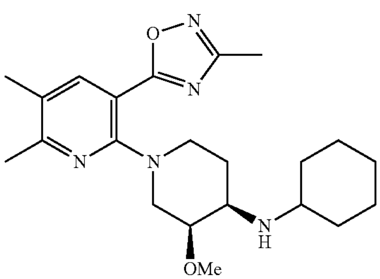 [SMILES: CO[C@H]1CN(c2nc(C)c(C)cc2-c2nc(C)no2)CC[C@H]1NC1CCCCC1] | 16 |
| 301 | trans-rac | 38 |
| 302 | 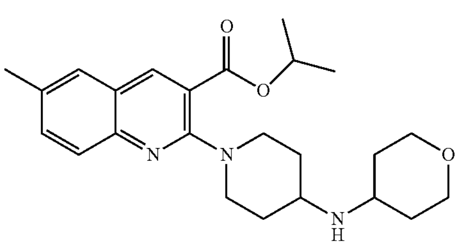 [SMILES: Cc1ccc2nc(N3CCC(NC4CCOCC4)CC3)c(C(=O)OC(C)C)cc2c1] | 274 |

TABLE I-continued
Compounds of the Invention
| Cpd. # | Structure | IC$_{50}$ nM (% inhib if other than 50%) |
|---|---|---|
| 303 | 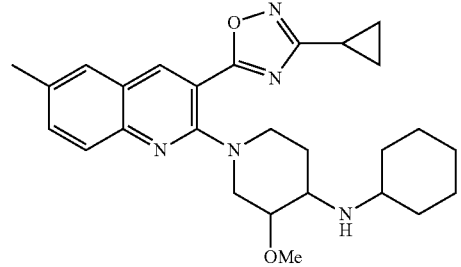<br>cis-rac | 0.5 |
| 304 | 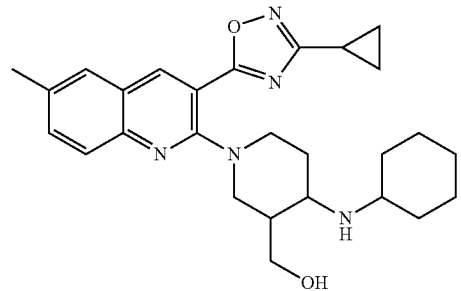<br>trans-rac | 3.5 |
| 305 | 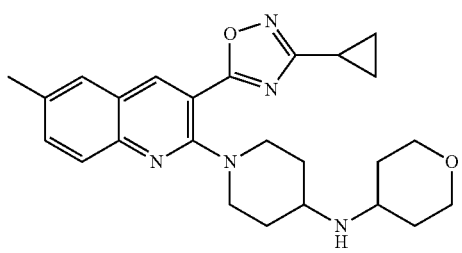 [SMILES: Cc1ccc2nc(N3CCC(NC4CCOCC4)CC3)c(-c3nc(C4CC4)no3)cc2c1] | 17 |
| 306 | 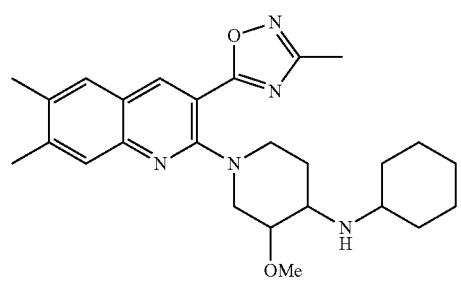<br>cis-rac | 107 |

TABLE I-continued

Compounds of the Invention

| Cpd. # | Structure | IC$_{50}$ nM (% inhib if other than 50%) |
|---|---|---|
| 307 | trans-rac | 41 |
| 308 | cis-rac | 2.5 |
| 309 | cis-rac | 0.5 |
| 310 | cis-rac | 4 |

TABLE I-continued

Compounds of the Invention

| Cpd. # | Structure | IC$_{50}$ nM (% inhib if other than 50%) |
|---|---|---|
| 311 | cis-rac | 1 |
| 312 | cis-rac | 0.7 |
| 313 | cis-rac | 1.5 |
| 314 | cis-rac | 2 |
| 315 | 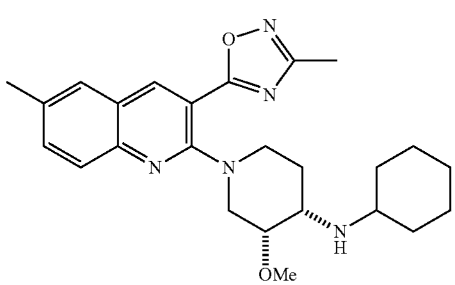 [SMILES: CO[C@@H]1CN(c2nc3ccc(C)cc3cc2-c2nc(C)no2)CC[C@@H]1NC1CCCCC1] | 4 |

TABLE I-continued

Compounds of the Invention

| Cpd. # | Structure | IC$_{50}$ nM (% inhib if other than 50%) |
|---|---|---|
| C90 | 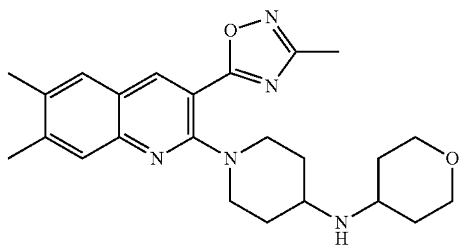 [SMILES: Cc1noc(-c2cc3cc(C)c(C)cc3nc2N2CCC(NC3CCOCC3)CC2)n1] | NA |
| 316 | cis-rac | 23 |
| 317 | cis-rac | 27 |
| 318 | cis-rac | 19 |
| 319 | cis-rac | 21 |

US 9,682,966 B2
181                                                                                       182
TABLE I-continued
Compounds of the Invention
| Cpd. # | Structure | IC$_{50}$ nM (% inhib if other than 50%) |
|---|---|---|
| 320 | 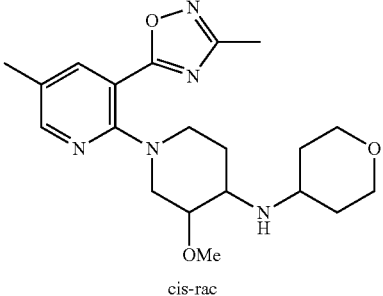 [SMILES: COC1CN(c2ncc(C)cc2-c2nc(C)no2)CCC1NC1CCOCC1]<br>cis-rac | 170 |
| 321 | 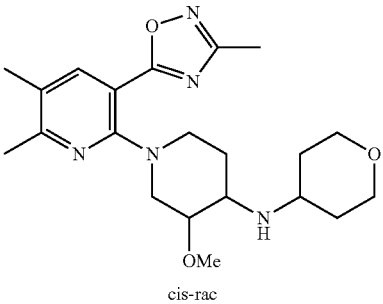 [SMILES: COC1CN(c2nc(C)c(C)cc2-c2nc(C)no2)CCC1NC1CCOCC1]<br>cis-rac | 105 |
| 322 | 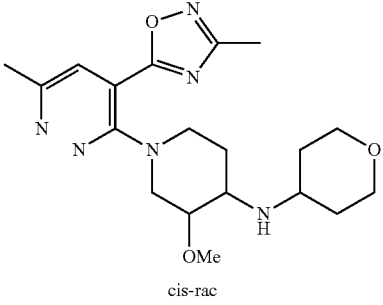 [SMILES: COC1CN(/C(N)=C(/C=C(/C)N)c2nc(C)no2)CCC1NC1CCOCC1]<br>cis-rac | 16 |
| 323 | 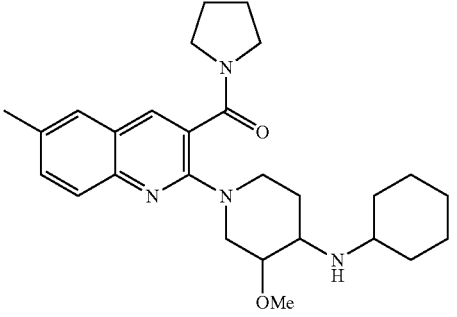<br>cis-rac | 1340 |

TABLE I-continued

Compounds of the Invention

| Cpd. # | Structure | IC$_{50}$ nM (% inhib if other than 50%) |
|---|---|---|
| 324 | 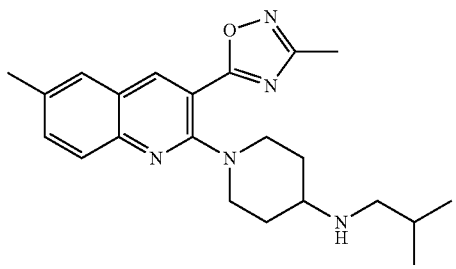 [SMILES: Cc1ccc2nc(N3CCC(NCC(C)C)CC3)c(-c3nc(C)no3)cc2c1] | 1.3 |
| 325 | cis-rac | 8 |
| 326 | cis-rac | 1.9 |
| 327 | cis-rac | 5.6 |

TABLE I-continued
Compounds of the Invention
| Cpd. # | Structure | IC$_{50}$ nM (% inhib if other than 50%) |
|---|---|---|
| 328 | 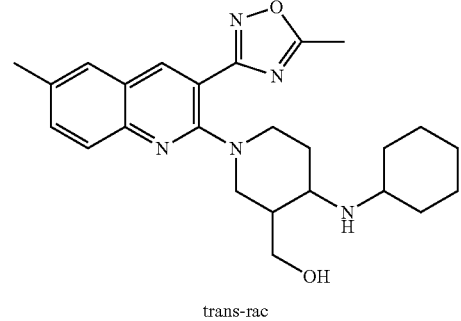 [SMILES: Cc1ccc2nc(N3CCC(NC4CCCCC4)C(CO)C3)c(-c3noc(C)n3)cc2c1]<br>trans-rac | 0.72 |
| 329 | 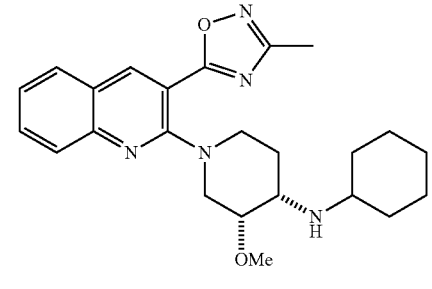 | 12.2 |
| 330 | 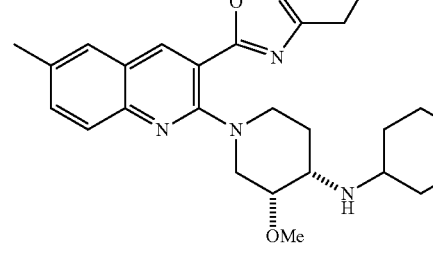 | 4.9 |
| 331 | 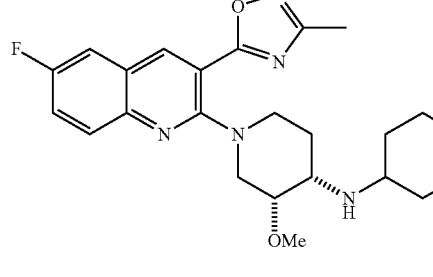 | 27 |
| 332 | 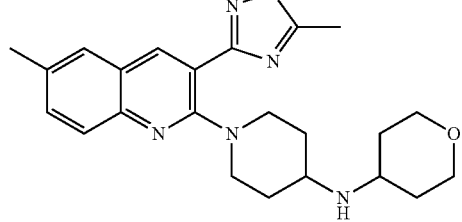 | 19 |

TABLE I-continued

Compounds of the Invention

| Cpd. # | Structure | IC$_{50}$ nM (% inhib if other than 50%) |
|---|---|---|
| 333 | 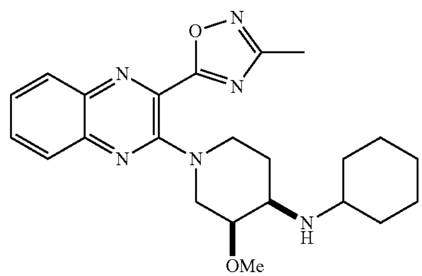 [SMILES: CO[C@H]1CN(c2nc3ccccc3nc2-c2nc(C)no2)CC[C@H]1NC1CCCCC1] | 6.6 |
| 334 | 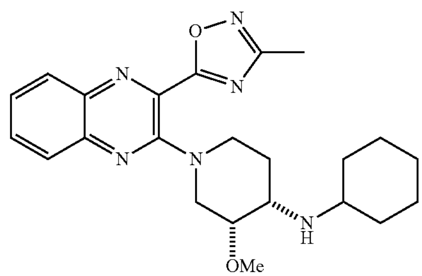 [SMILES: CO[C@@H]1CN(c2nc3ccccc3nc2-c2nc(C)no2)CC[C@@H]1NC1CCCCC1] | 161 |
| 335 | 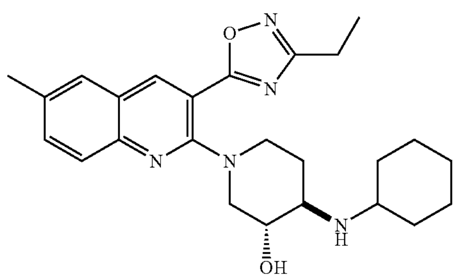 [SMILES: CCc1noc(-c2cc3cc(C)ccc3nc2N2CC[C@@H](NC3CCCCC3)[C@H](O)C2)n1] | 113 |
| C91 | trans-rac | 17700 |
| 336 | trans-rac | 4360 |

TABLE I-continued

Compounds of the Invention

| Cpd. # | Structure | IC$_{50}$ nM (% inhib if other than 50%) |
|---|---|---|
| 337 | 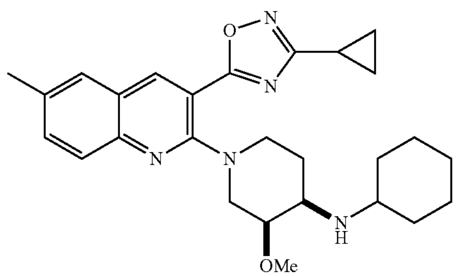 [SMILES: CO[C@H]1CN(c2nc3ccc(C)cc3cc2-c2nc(C3CC3)no2)CC[C@H]1NC1CCCCC1] | 0.73 |
| 338 | 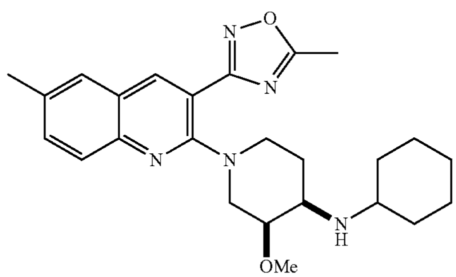 [SMILES: CO[C@H]1CN(c2nc3ccc(C)cc3cc2-c2noc(C)n2)CC[C@H]1NC1CCCCC1] | 0.99 |
| 339 | 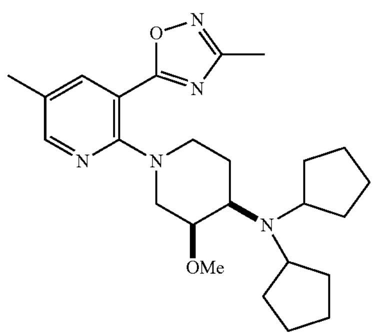 [SMILES: CO[C@H]1CN(c2ncc(C)cc2-c2nc(C)no2)CC[C@H]1N(C1CCCC1)C1CCCC1] | 29 |
| 340 | 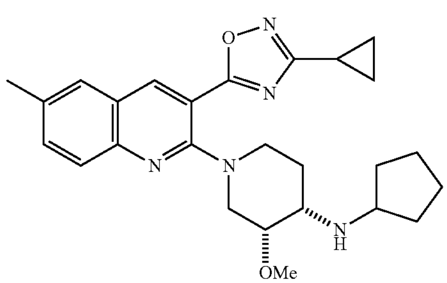 [SMILES: CO[C@@H]1CN(c2nc3ccc(C)cc3cc2-c2nc(C3CC3)no2)CC[C@@H]1NC1CCCC1] | 6 |
| 341 | 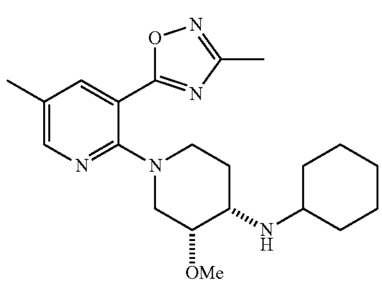 [SMILES: CO[C@@H]1CN(c2ncc(C)cc2-c2nc(C)no2)CC[C@@H]1NC1CCCCC1] | 76 |

TABLE I-continued

Compounds of the Invention

| Cpd. # | Structure | IC$_{50}$ nM (% inhib if other than 50%) |
|---|---|---|
| 342 | 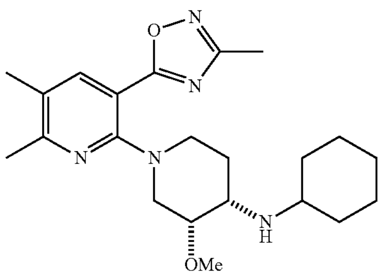 [SMILES: CO[C@@H]1CN(c2nc(C)c(C)cc2-c2nc(C)no2)CC[C@@H]1NC1CCCCC1] | 48 |
| 343 | 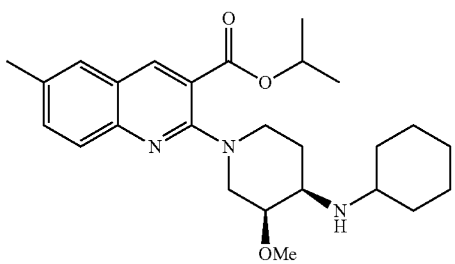 [SMILES: CO[C@H]1CN(c2nc3ccc(C)cc3cc2C(=O)OC(C)C)CC[C@H]1NC1CCCCC1] | 10.6 |
| 344 | 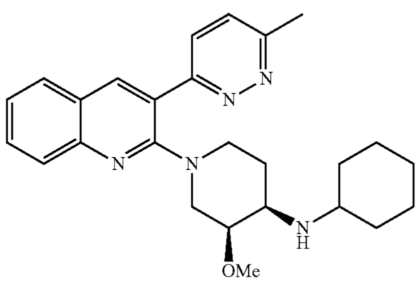 [SMILES: CO[C@H]1CN(c2nc3ccccc3cc2-c2ccc(C)nn2)CC[C@H]1NC1CCCCC1] | 16.8 |
| 345 | 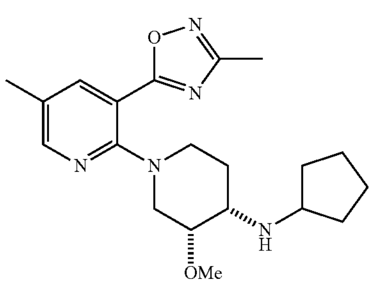 [SMILES: CO[C@@H]1CN(c2ncc(C)cc2-c2nc(C)no2)CC[C@@H]1NC1CCCC1] | 104 |
| 346 | 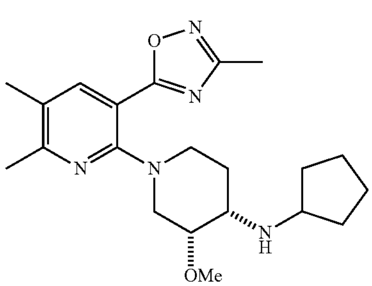 [SMILES: CO[C@@H]1CN(c2nc(C)c(C)cc2-c2nc(C)no2)CC[C@@H]1NC1CCCC1] | 137 |

TABLE I-continued

Compounds of the Invention

| Cpd. # | Structure | IC₅₀ nM (% inhib if other than 50%) |
|---|---|---|
| 347 | 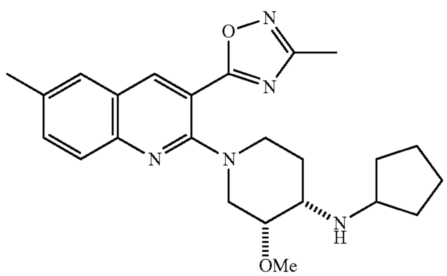 [SMILES: CO[C@@H]1CN(c2nc3ccc(C)cc3cc2-c2nc(C)no2)CC[C@@H]1NC1CCCC1] | 32 |
| 348 | 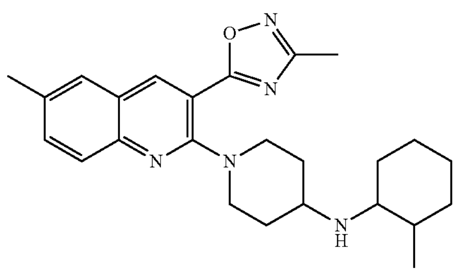 [SMILES: Cc1ccc2nc(N3CCC(NC4CCCCC4C)CC3)c(-c3nc(C)no3)cc2c1] | 1.3 |
| 349 | 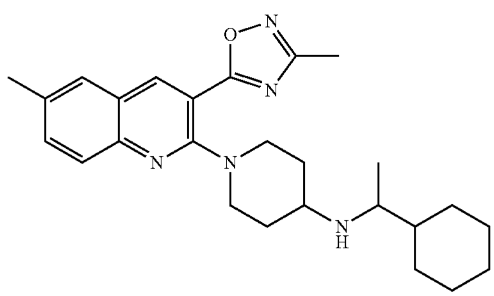 [SMILES: Cc1ccc2nc(N3CCC(NC(C)C4CCCCC4)CC3)c(-c3nc(C)no3)cc2c1] | 21 |
| 350 | 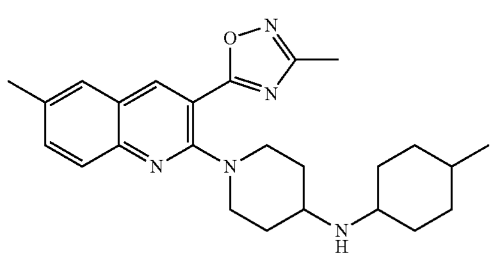 | 0.97 |
| 351 | 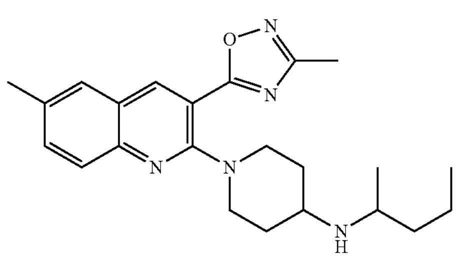 [SMILES: CCCC(C)NC1CCN(c2nc3ccc(C)cc3cc2-c2nc(C)no2)CC1] | 3 |

TABLE I-continued

Compounds of the Invention

| Cpd. # | Structure | IC$_{50}$ nM (% inhib if other than 50%) |
|---|---|---|
| 352 | 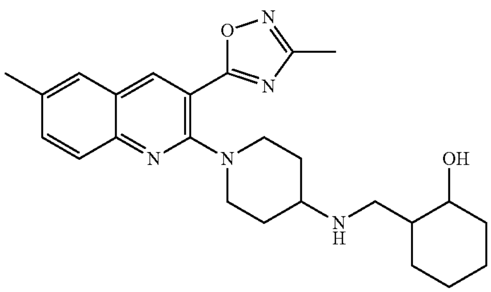 [SMILES: Cc1ccc2nc(N3CCC(NCC4CCCCC4O)CC3)c(-c3nc(C)no3)cc2c1] | 3.1 |
| 353 | cis-rac | 23 |
| 354 | 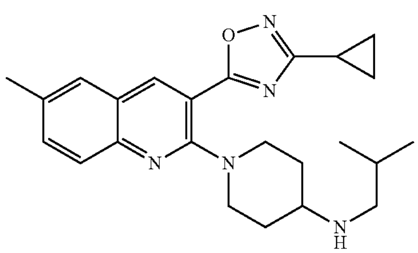 [SMILES: Cc1ccc2nc(N3CCC(NCC(C)C)CC3)c(-c3nc(C4CC4)no3)cc2c1] | 4.2 |
| 355 | 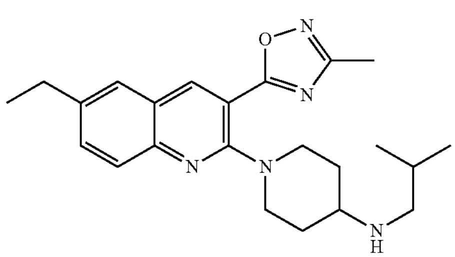 [SMILES: CCc1ccc2nc(N3CCC(NCC(C)C)CC3)c(-c3nc(C)no3)cc2c1] | 1.2 |
| 356 | 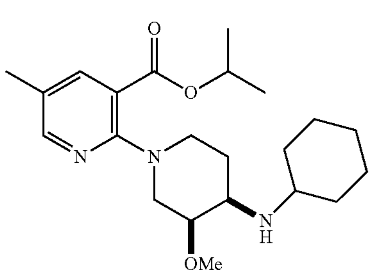 [SMILES: CO[C@H]1CN(c2ncc(C)cc2C(=O)OC(C)C)CC[C@H]1NC1CCCCC1] | 12.5 |

TABLE I-continued

Compounds of the Invention

| Cpd. # | Structure | IC$_{50}$ nM (% inhib if other than 50%) |
|---|---|---|
| 357 | 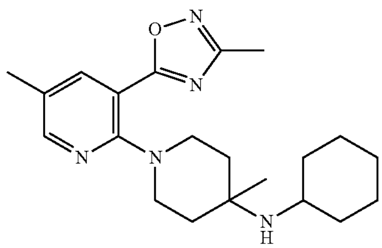 [SMILES: Cc1cnc(N2CCC(C)(NC3CCCCC3)CC2)c(-c2nc(C)no2)c1] | 22.3 |
| 358 | cis-rac | 9 |
| C92 | cis-rac | 58000 |
| 359 | 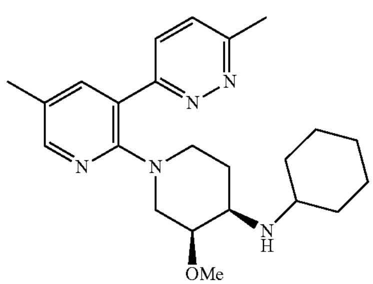 [SMILES: CO[C@H]1CN(c2ncc(C)cc2-c2ccc(C)nn2)CC[C@H]1NC1CCCCC1] | 160 |
| C93 | 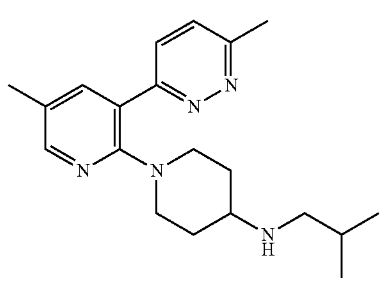 [SMILES: Cc1cnc(N2CCC(NCC(C)C)CC2)c(-c2ccc(C)nn2)c1] | 10181 |

TABLE I-continued

Compounds of the Invention

| Cpd. # | Structure | IC$_{50}$ nM (% inhib if other than 50%) |
|---|---|---|
| 360 | 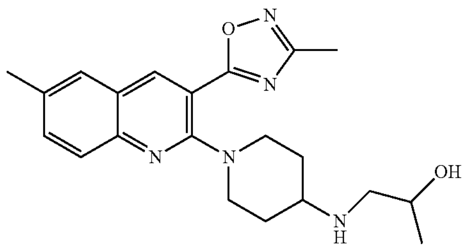 [SMILES: Cc1ccc2nc(N3CCC(NCC(C)O)CC3)c(-c3nc(C)no3)cc2c1] | 8 |
| 361 | 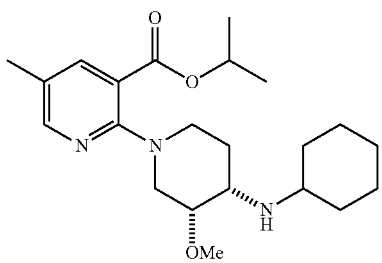 [SMILES: CO[C@@H]1CN(c2ncc(C)cc2C(=O)OC(C)C)CC[C@@H]1NC1CCCCC1] | 1440 |
| 362 | 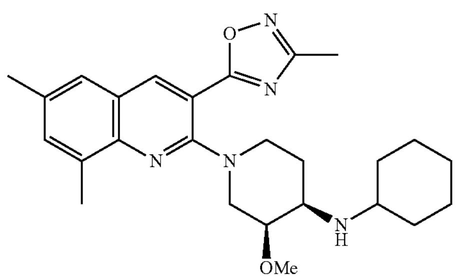 [SMILES: CO[C@H]1CN(c2nc3c(C)cc(C)cc3cc2-c2nc(C)no2)CC[C@H]1NC1CCCCC1] | 3 |
| 363 | 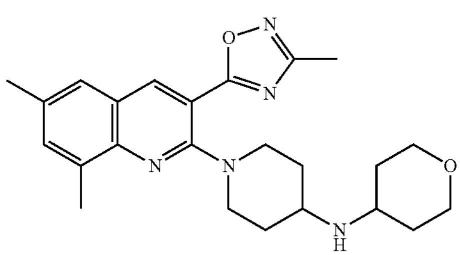 [SMILES: Cc1cc(C)c2nc(N3CCC(NC4CCOCC4)CC3)c(-c3nc(C)no3)cc2c1] | 10 |
| 364 | 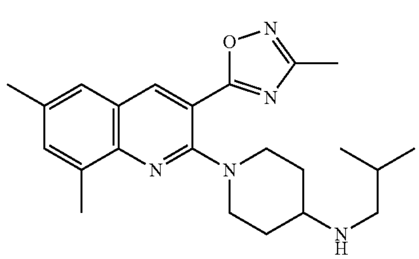 [SMILES: Cc1cc(C)c2nc(N3CCC(NCC(C)C)CC3)c(-c3nc(C)no3)cc2c1] | 18 |

TABLE I-continued

Compounds of the Invention

| Cpd. # | Structure | IC$_{50}$ nM (% inhib if other than 50%) |
|---|---|---|
| 365 | 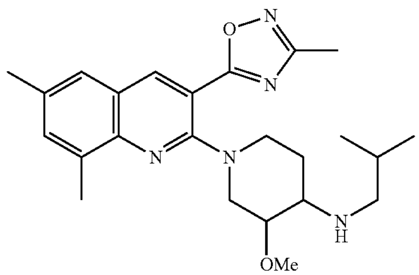 [SMILES: COC1CN(c2nc3c(C)cc(C)cc3cc2-c2nc(C)no2)CCC1NCC(C)C] | 8 |
| 366 | 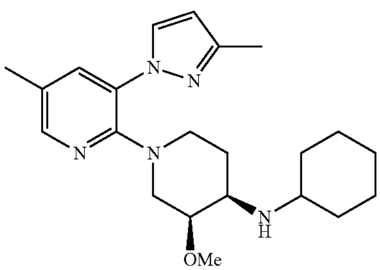 [SMILES: CO[C@H]1CN(c2ncc(C)cc2-n2ccc(C)n2)CC[C@H]1NC1CCCCC1] | 19 |
| 367 | 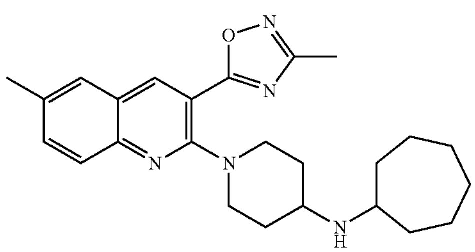 [SMILES: Cc1ccc2nc(N3CCC(NC4CCCCCC4)CC3)c(-c3nc(C)no3)cc2c1] | 2 |
| 368 | (trans-rac) | 7 |
| 369 | 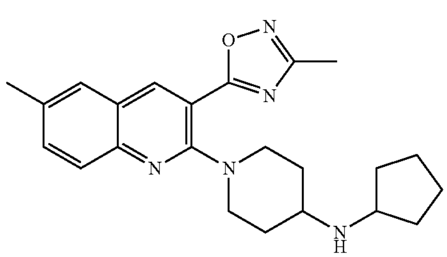 [SMILES: Cc1ccc2nc(N3CCC(NC4CCCC4)CC3)c(-c3nc(C)no3)cc2c1] | 2 |

TABLE I-continued

Compounds of the Invention

| Cpd. # | Structure | IC₅₀ nM (% inhib if other than 50%) |
|---|---|---|
| 370 | 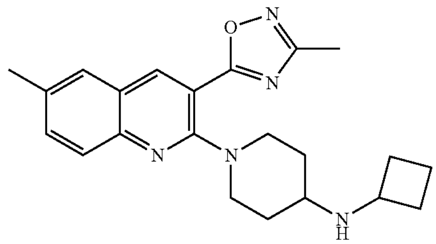 [SMILES: Cc1ccc2nc(N3CCC(NC4CCC4)CC3)c(-c3nc(C)no3)cc2c1] | 37 |
| 371 | cis-rac | 1 |
| 372 | 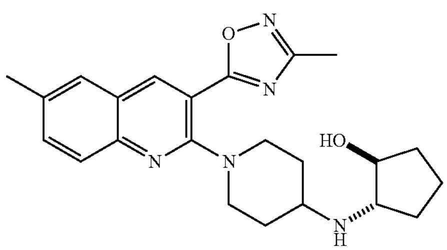 | 15 |
| 373 | trans-rac | 63 |
| 374 | cis-rac | 45 |

TABLE I-continued
Compounds of the Invention
| Cpd. # | Structure | IC$_{50}$ nM (% inhib if other than 50%) |
|---|---|---|
| 375 | 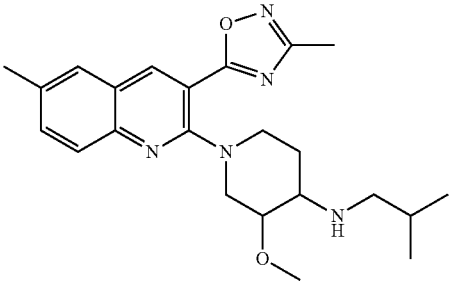 cis-rac | 12 |
| 376 | 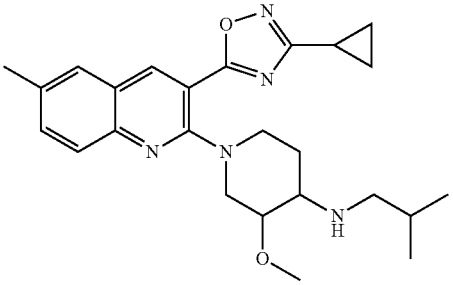 cis-rac | 14 |
| 377 | 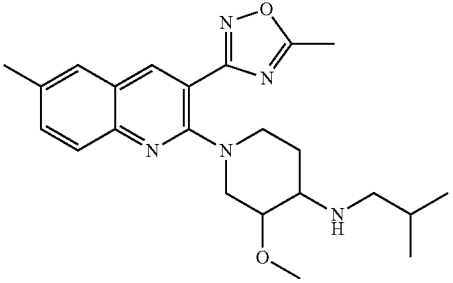 cis-rac | 69 |
| 378 | 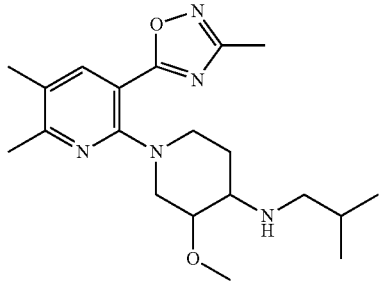 cis-rac | 256 |

TABLE I-continued

Compounds of the Invention

| Cpd. # | Structure | IC$_{50}$ nM (% inhib if other than 50%) |
|---|---|---|
| 379 | cis-rac | 525 |
| 380 | cis-rac | 128 |
| 381 | 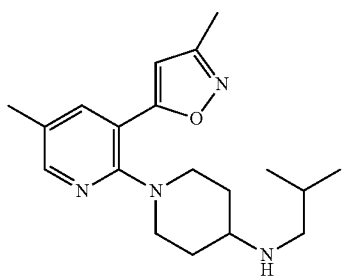 [SMILES: Cc1cnc(N2CCC(NCC(C)C)CC2)c(-c2cc(C)no2)c1] | 860 |
| 382 | 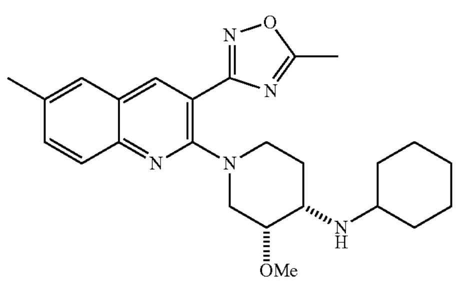 [SMILES: CO[C@@H]1CN(c2nc3ccc(C)cc3cc2-c2noc(C)n2)CC[C@@H]1NC1CCCCC1] | 83 |
| 383 | 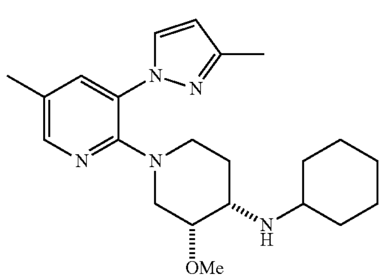 [SMILES: CO[C@@H]1CN(c2ncc(C)cc2-n2ccc(C)n2)CC[C@@H]1NC1CCCCC1] | 1161 |

TABLE I-continued

Compounds of the Invention

| Cpd. # | Structure | IC$_{50}$ nM (% inhib if other than 50%) |
|---|---|---|
| 384 | cis-rac | 16700 |
| 385 | 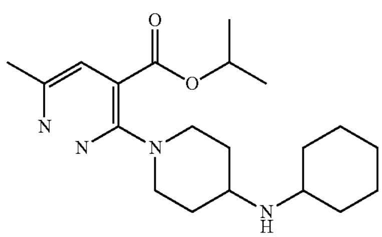 [SMILES: C/C(N)=C/C(C(=O)OC(C)C)=C(\N)N1CCC(NC2CCCCC2)CC1] | 1 |
| 386 | trans-rac | 31 |
| 387 | 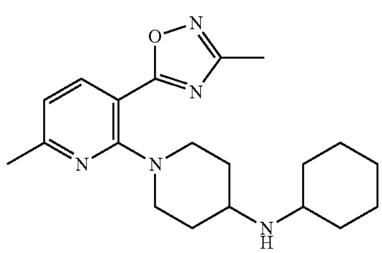 [SMILES: Cc1ccc(-c2nc(C)no2)c(N2CCC(NC3CCCCC3)CC2)n1] | 89 |
| 388 | 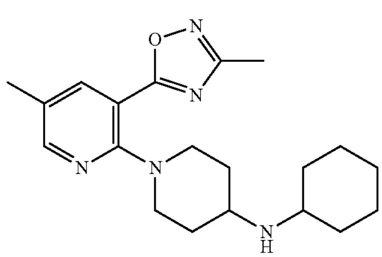 [SMILES: Cc1cnc(N2CCC(NC3CCCCC3)CC2)c(-c2nc(C)no2)c1] | 20 |

TABLE I-continued

Compounds of the Invention

| Cpd. # | Structure | IC$_{50}$ nM (% inhib if other than 50%) |
|---|---|---|
| 389 | 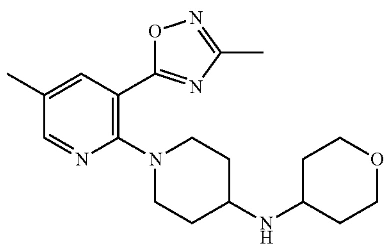 [SMILES: Cc1cnc(N2CCC(NC3CCOCC3)CC2)c(-c2nc(C)no2)c1] | 153 |
| 390 | cis-rac | 1920 |
| 391 | cis-rac | 105 |
| 392 | cis-rac | 2960 |
| 393 | 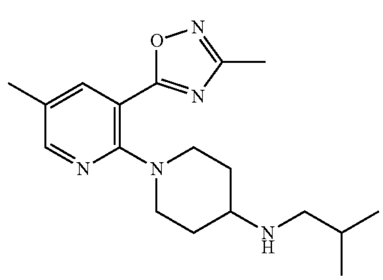 [SMILES: Cc1cnc(N2CCC(NCC(C)C)CC2)c(-c2nc(C)no2)c1] | 346 |

TABLE I-continued

Compounds of the Invention

| Cpd. # | Structure | IC$_{50}$ nM (% inhib if other than 50%) |
|---|---|---|
| 394 | 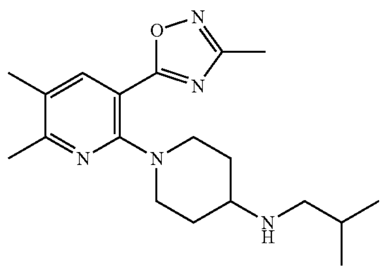 [SMILES: Cc1noc(-c2cc(C)c(C)nc2N2CCC(NCC(C)C)CC2)n1] | 161 |
| 395 | 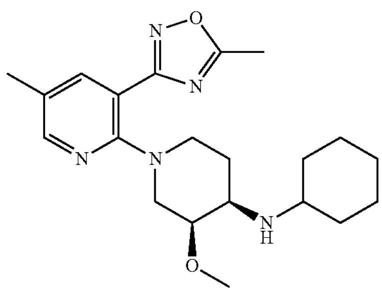 [SMILES: CO[C@H]1CN(c2ncc(C)cc2-c2noc(C)n2)CC[C@H]1NC1CCCCC1] | 49 |
| 396 | 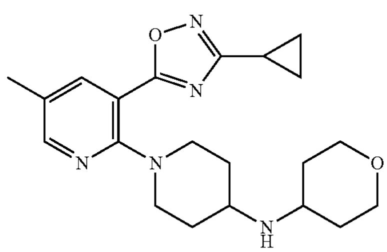 [SMILES: Cc1cnc(N2CCC(NC3CCOCC3)CC2)c(-c2nc(C3CC3)no2)c1] | 2263 |
| 397 | 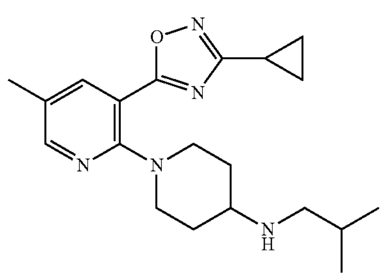 [SMILES: Cc1cnc(N2CCC(NCC(C)C)CC2)c(-c2nc(C3CC3)no2)c1] | 1280 |
| 398 | 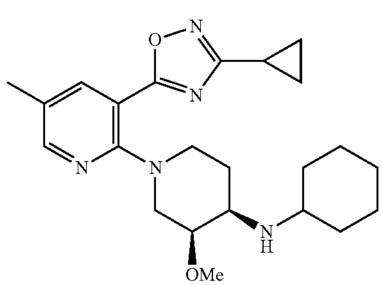 | 18 |

TABLE I-continued

Compounds of the Invention

| Cpd. # | Structure | IC$_{50}$ nM (% inhib if other than 50%) |
|---|---|---|
| 399 | 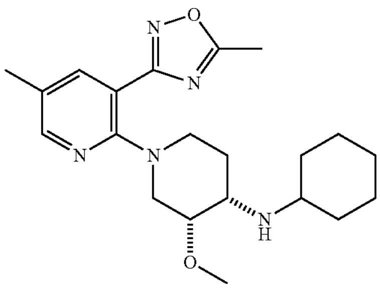 [SMILES: CO[C@@H]1CN(c2ncc(C)cc2-c2noc(C)n2)CC[C@@H]1NC1CCCCC1] | 953 |
| 400 | 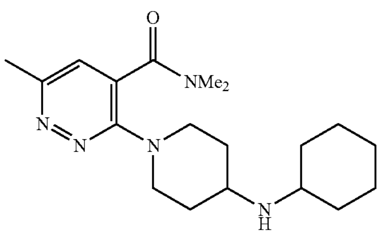 [SMILES: Cc1cc(C(=O)N(C)C)c(N2CCC(NC3CCCCC3)CC2)nn1] | 279 |
| 401 | cis-rac | 67 |
| 402 | 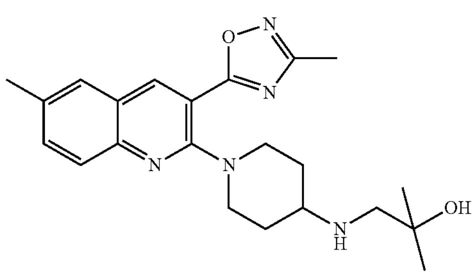 [SMILES: Cc1ccc2nc(N3CCC(NCC(C)(C)O)CC3)c(-c3nc(C)no3)cc2c1] | 16 |
| 403 | 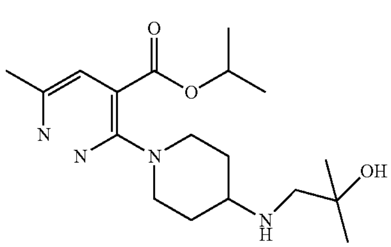 [SMILES: C/C(N)=C/C(C(=O)OC(C)C)=C(\N)N1CCC(NCC(C)(C)O)CC1] | 322 |

TABLE I-continued

Compounds of the Invention

| Cpd. # | Structure | IC$_{50}$ nM (% inhib if other than 50%) |
|---|---|---|
| 404 | 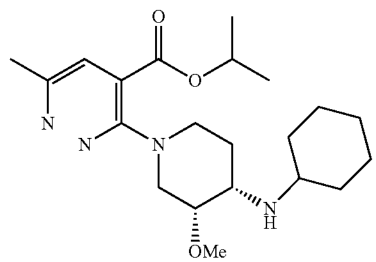 [SMILES: CO[C@@H]1CN(/C(N)=C(/C=C(/C)N)C(=O)OC(C)C)CC[C@@H]1NC1CCCCC1] | 63 |
| 405 | 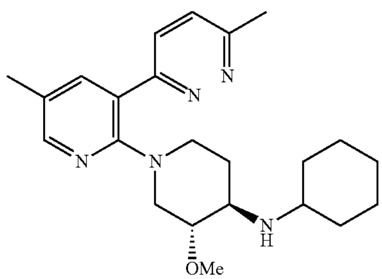 [SMILES: CO[C@@H]1CN(c2ncc(C)cc2C(=N)/C=C\C(C)=N)CC[C@H]1NC1CCCCC1] | 21400 |
| 406 | 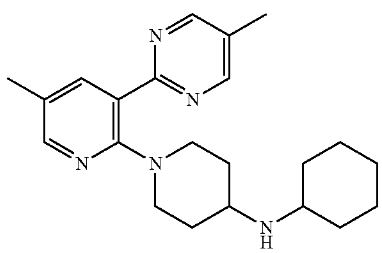 [SMILES: Cc1cnc(-c2cc(C)cnc2N2CCC(NC3CCCCC3)CC2)nc1] | 7680 |
| 407 | 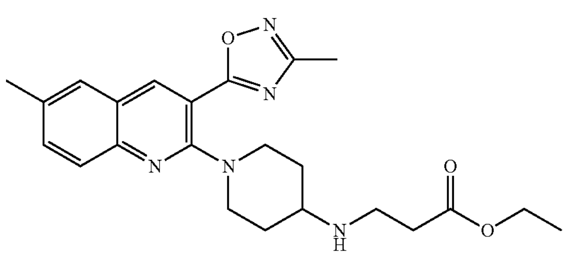 [SMILES: CCOC(=O)CCNC1CCN(c2nc3ccc(C)cc3cc2-c2nc(C)no2)CC1] | 341 |
| 408 | cis-rac | 57 |

TABLE I-continued

Compounds of the Invention

| Cpd. # | Structure | IC$_{50}$ nM (% inhib if other than 50%) |
|---|---|---|
| 409 | 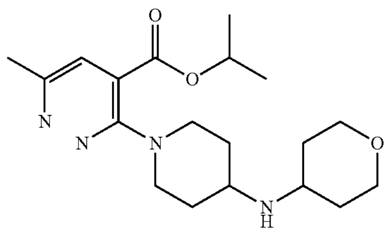 [SMILES: C/C(N)=C/C(C(=O)OC(C)C)=C(\N)N1CCC(NC2CCOCC2)CC1] | 129 |
| 410 | 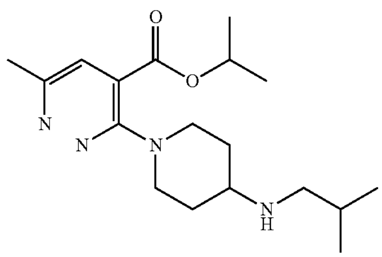 [SMILES: C/C(N)=C/C(C(=O)OC(C)C)=C(\N)N1CCC(NCC(C)C)CC1] | 78 |
| 411 | 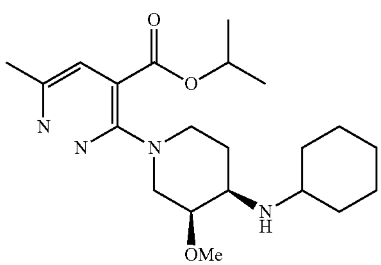 [SMILES: CO[C@H]1CN(/C(N)=C(/C=C(/C)N)C(=O)OC(C)C)CC[C@H]1NC1CCCCC1] | 10 |
| 412 | 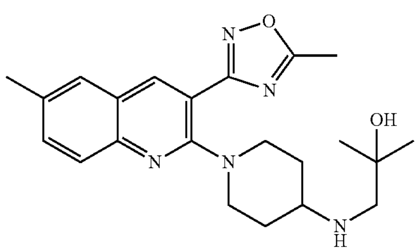 [SMILES: Cc1ccc2nc(N3CCC(NCC(C)(C)O)CC3)c(-c3noc(C)n3)cc2c1] | 476 |
| 413 | 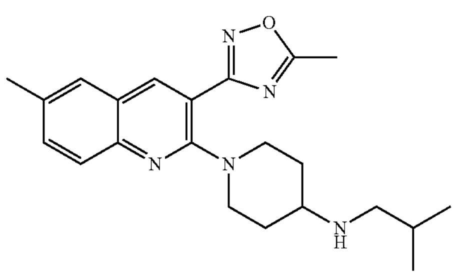 [SMILES: Cc1ccc2nc(N3CCC(NCC(C)C)CC3)c(-c3noc(C)n3)cc2c1] | 22 |
| 414 | 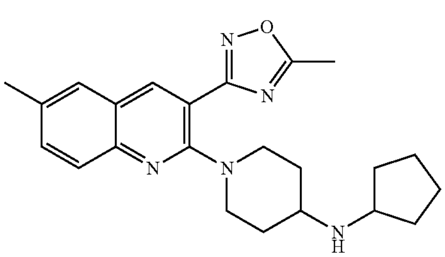 [SMILES: Cc1ccc2nc(N3CCC(NC4CCCC4)CC3)c(-c3noc(C)n3)cc2c1] | 9 |

TABLE I-continued

Compounds of the Invention

| Cpd. # | Structure | IC$_{50}$ nM (% inhib if other than 50%) |
|---|---|---|
| 415 | 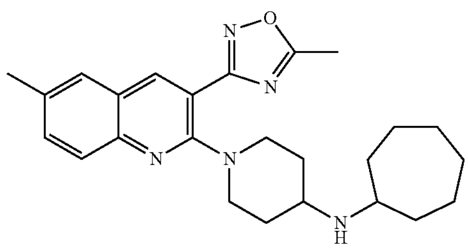 [SMILES: Cc1ccc2nc(N3CCC(NC4CCCCCC4)CC3)c(-c3noc(C)n3)cc2c1] | 3 |
| 416 | 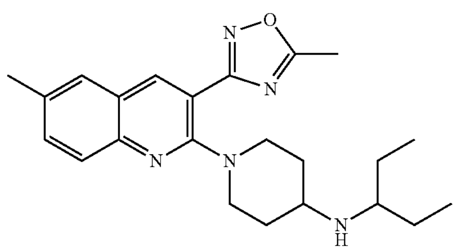 [SMILES: CCC(CC)NC1CCN(c2nc3ccc(C)cc3cc2-c2noc(C)n2)CC1] | 4 |
| 417 | 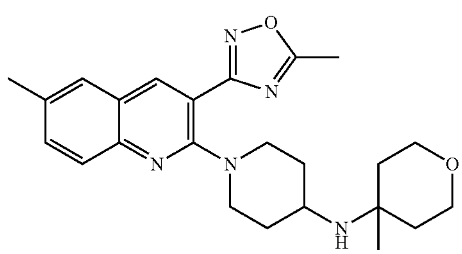 [SMILES: Cc1ccc2nc(N3CCC(NC4(C)CCOCC4)CC3)c(-c3noc(C)n3)cc2c1] | 105 |
| 418 | 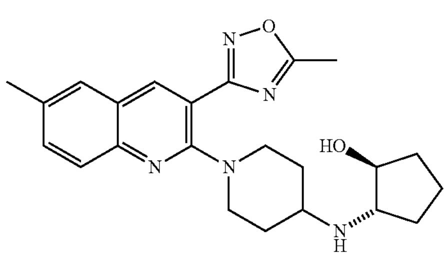 | 50 |
| 419 | rac | 2 |

TABLE I-continued
Compounds of the Invention
| Cpd. # | Structure | IC$_{50}$ nM (% inhib if other than 50%) |
|---|---|---|
| 420 | 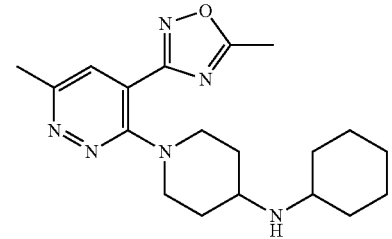 [SMILES: Cc1cc(-c2noc(C)n2)c(N2CCC(NC3CCCCC3)CC2)nn1] | 3 |
| 421 | 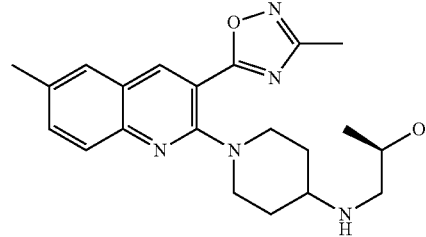 | 48 |
| 422 | 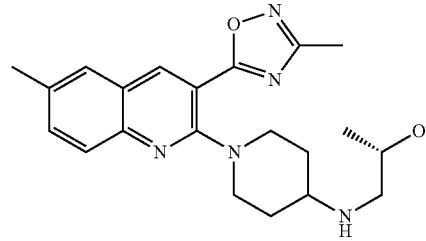 | 106 |
| 423 | 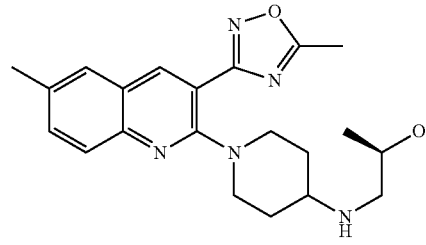 | 191 |
| 424 | 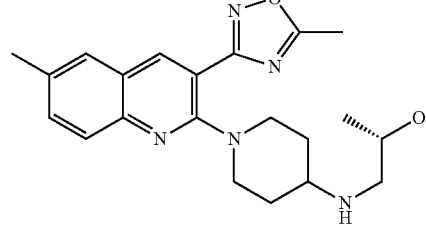 | 422 |

TABLE I-continued

Compounds of the Invention

| Cpd. # | Structure | IC$_{50}$ nM (% inhib if other than 50%) |
|---|---|---|
| 425 | cis-rac | 60 |
| 426 | 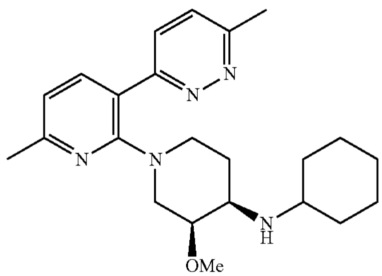 [SMILES: CO[C@H]1CN(c2nc(C)ccc2-c2ccc(C)nn2)CC[C@H]1NC1CCCCC1] | 1970 |
| 427 | 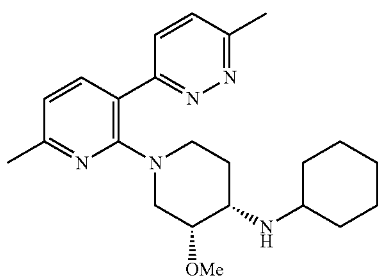 [SMILES: CO[C@@H]1CN(c2nc(C)ccc2-c2ccc(C)nn2)CC[C@@H]1NC1CCCCC1] | 4600 |
| 428 | 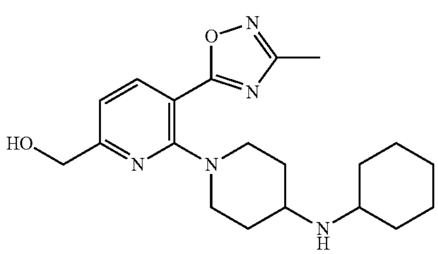 [SMILES: Cc1noc(-c2ccc(CO)nc2N2CCC(NC3CCCCC3)CC2)n1] | 101 |
| 429 | 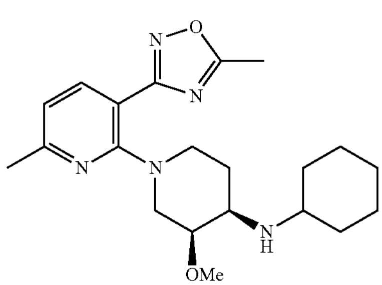 [SMILES: CO[C@H]1CN(c2nc(C)ccc2-c2noc(C)n2)CC[C@H]1NC1CCCCC1] | 214 |

TABLE I-continued

Compounds of the Invention

| Cpd. # | Structure | IC$_{50}$ nM (% inhib if other than 50%) |
|---|---|---|
| 430 | 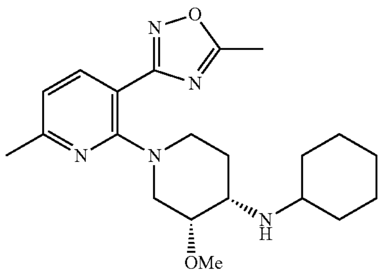 [SMILES: CO[C@@H]1CN(c2nc(C)ccc2-c2noc(C)n2)CC[C@@H]1NC1CCCCC1] | 1000 |
| 431 | 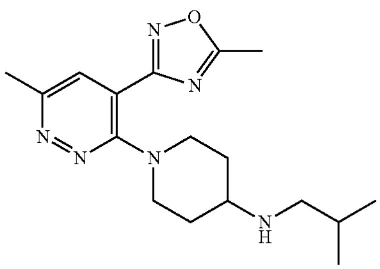 [SMILES: Cc1cc(-c2noc(C)n2)c(N2CCC(NCC(C)C)CC2)nn1] | 22 |
| 432 | 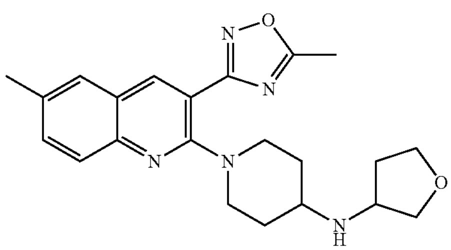 | 22 |
| 433 | 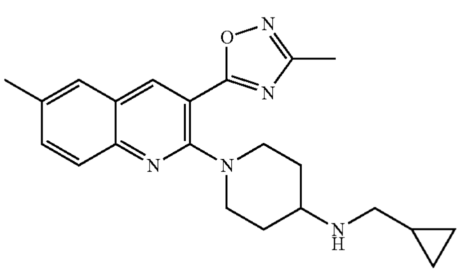 [SMILES: Cc1ccc2nc(N3CCC(NCC4CC4)CC3)c(-c3nc(C)no3)cc2c1] | 7 |
| 434 | 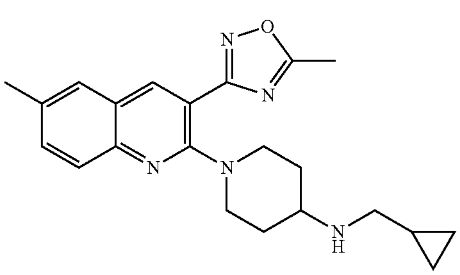 [SMILES: Cc1ccc2nc(N3CCC(NCC4CC4)CC3)c(-c3noc(C)n3)cc2c1] | 43 |

TABLE I-continued

Compounds of the Invention

| Cpd. # | Structure | IC$_{50}$ nM (% inhib if other than 50%) |
|---|---|---|
| 435 | 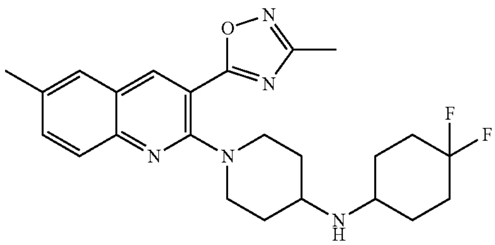 [SMILES: Cc1ccc2nc(N3CCC(NC4CCC(F)(F)CC4)CC3)c(-c3nc(C)no3)cc2c1] | 6 |
| 436 | 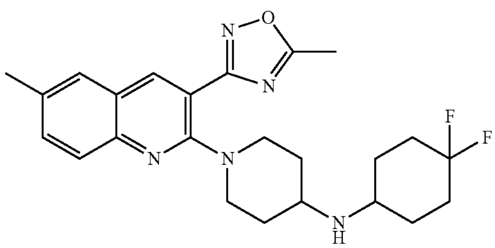 [SMILES: Cc1ccc2nc(N3CCC(NC4CCC(F)(F)CC4)CC3)c(-c3noc(C)n3)cc2c1] | 26 |
| 437 | 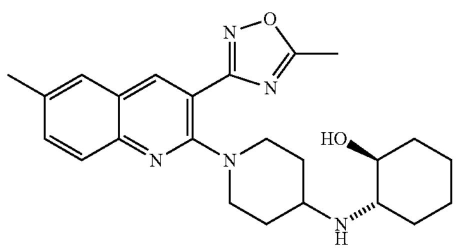 | 17 |
| 438 | 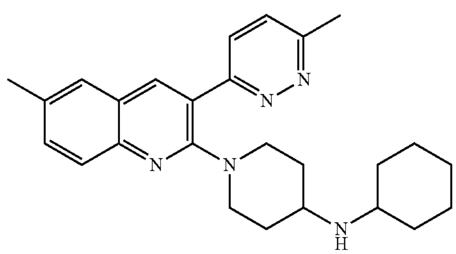 [SMILES: Cc1ccc2nc(N3CCC(NC4CCCCC4)CC3)c(-c3ccc(C)nn3)cc2c1] | 75 |
| 439 | 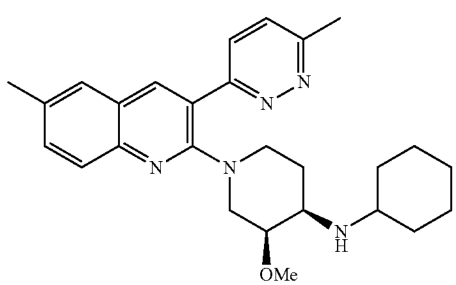 [SMILES: CO[C@H]1CN(c2nc3ccc(C)cc3cc2-c2ccc(C)nn2)CC[C@H]1NC1CCCCC1] | 231 |
| 440 | 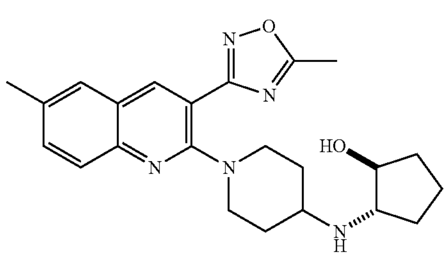 | 70 |

TABLE I-continued

Compounds of the Invention

| Cpd. # | Structure | IC$_{50}$ nM (% inhib if other than 50%) |
|---|---|---|
| 441 | 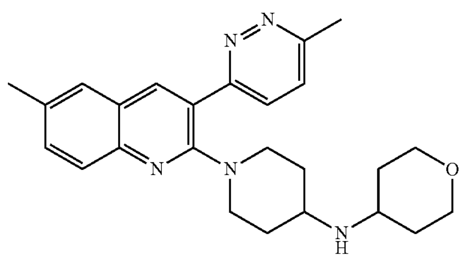 [SMILES: Cc1ccc2nc(N3CCC(NC4CCOCC4)CC3)c(-c3ccc(C)nn3)cc2c1] | 392 |
| 442 | 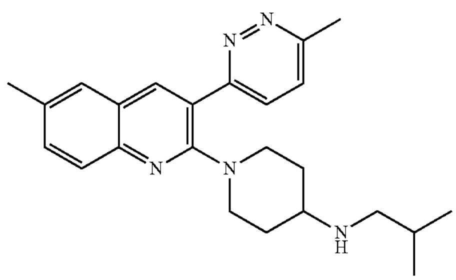 [SMILES: Cc1ccc2nc(N3CCC(NCC(C)C)CC3)c(-c3ccc(C)nn3)cc2c1] | 324 |
| 443 | 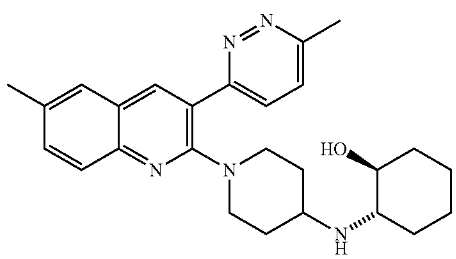 | 33 |
| 444 | 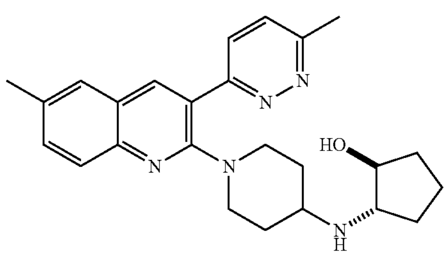 | 634 |
| 445 | 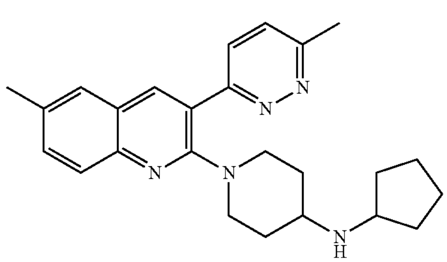 [SMILES: Cc1ccc2nc(N3CCC(NC4CCCC4)CC3)c(-c3ccc(C)nn3)cc2c1] | 55 |

TABLE I-continued

Compounds of the Invention

| Cpd. # | Structure | IC$_{50}$ nM (% inhib if other than 50%) |
|---|---|---|
| 446 | 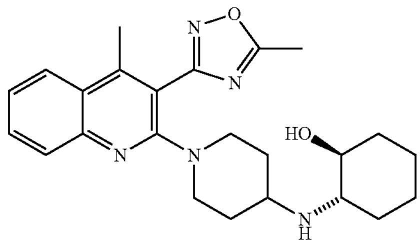 | 72 |
| 447 | 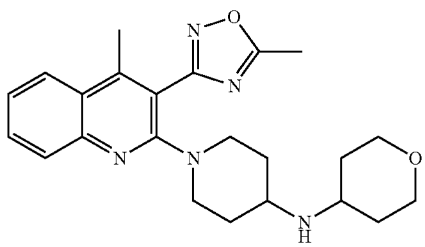 [SMILES: Cc1nc(-c2c(N3CCC(NC4CCOCC4)CC3)nc3ccccc3c2C)no1] | 1150 |
| 448 | 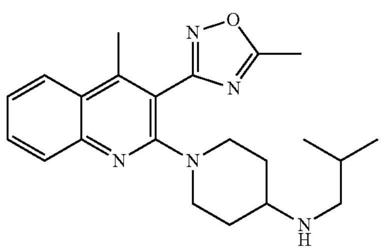 [SMILES: Cc1nc(-c2c(N3CCC(NCC(C)C)CC3)nc3ccccc3c2C)no1] | 226 |
| 449 | 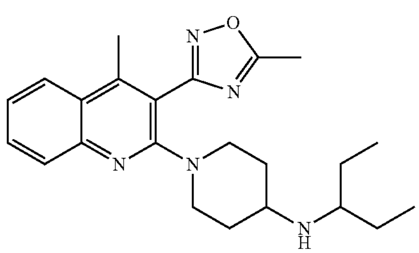 [SMILES: CCC(CC)NC1CCN(c2nc3ccccc3c(C)c2-c2noc(C)n2)CC1] | 129 |
| 450 | cis-rac | 11 |

US 9,682,966 B2
TABLE I-continued
Compounds of the Invention
| Cpd. # | Structure | IC$_{50}$ nM (% inhib if other than 50%) |
|---|---|---|
| 451 | 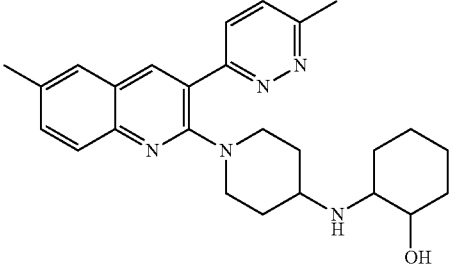 cis-rac | 94 |
| 452 | 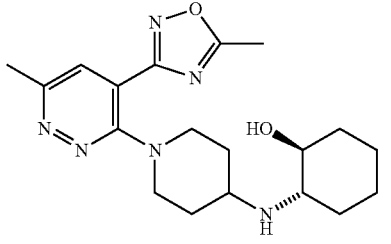 | 47 |
| 453 | 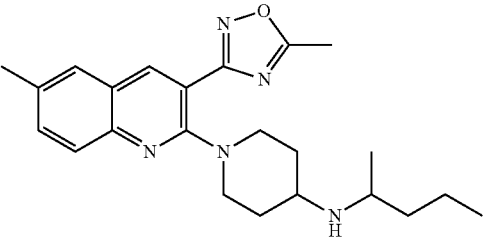 rac | 85 |
| 454 | 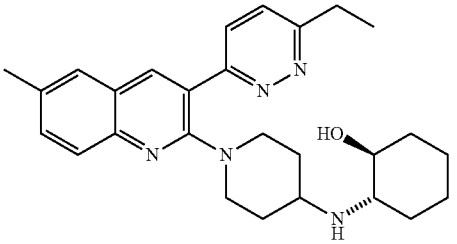 | 783 |
| 455 | 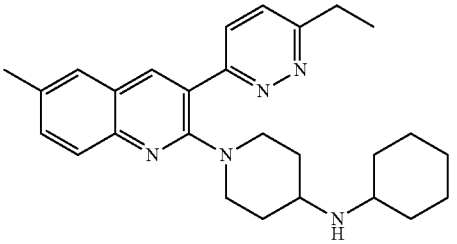 [SMILES: CCc1ccc(-c2cc3cc(C)ccc3nc2N2CCC(NC3CCCCC3)CC2)nn1] | 1640 |

TABLE I-continued
Compounds of the Invention
| Cpd. # | Structure | IC$_{50}$ nM (% inhib if other than 50%) |
|---|---|---|
| 456 | 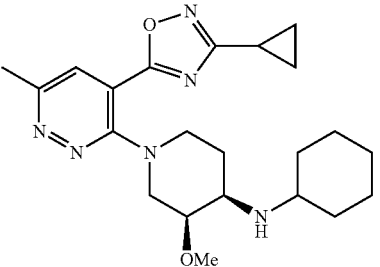 [SMILES: CO[C@H]1CN(c2nnc(C)cc2-c2nc(C3CC3)no2)CC[C@H]1NC1CCCCC1] | 6 |
| 457 | 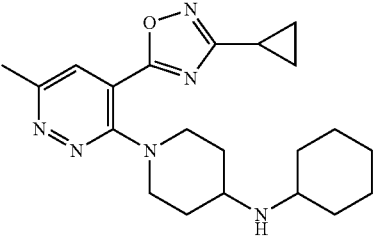 [SMILES: Cc1cc(-c2nc(C3CC3)no2)c(N2CCC(NC3CCCCC3)CC2)nn1] | 24 |
| 458 | 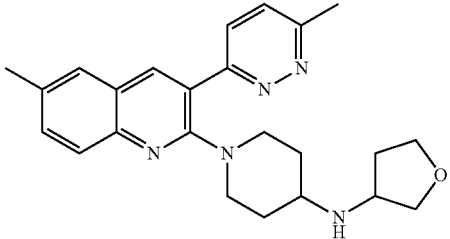 rac | 440 |
| 459 | 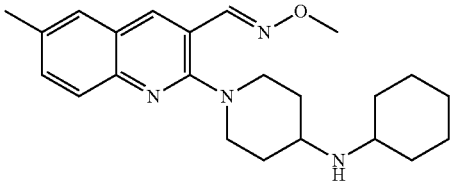 [SMILES: CO/N=C/c1cc2cc(C)ccc2nc1N1CCC(NC2CCCCC2)CC1] | 15 |
| 460 | 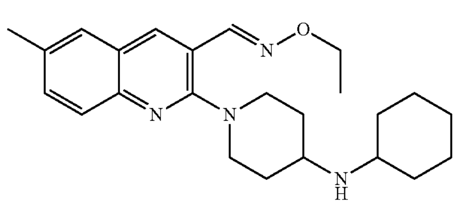 [SMILES: CCO/N=C/c1cc2cc(C)ccc2nc1N1CCC(NC2CCCCC2)CC1] | 141 |

TABLE I-continued
Compounds of the Invention
| Cpd. # | Structure | IC$_{50}$ nM (% inhib if other than 50%) |
|---|---|---|
| 461 | 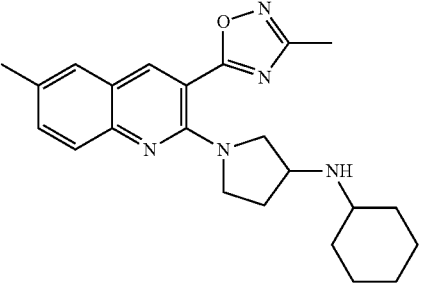 rac | 52 |
| 462 | 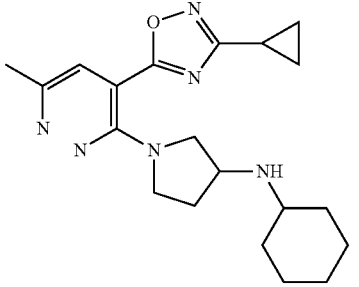 rac | 320 |
| 463 | 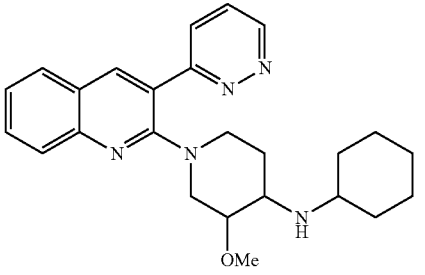 cis-rac | 54 |
| 464 | 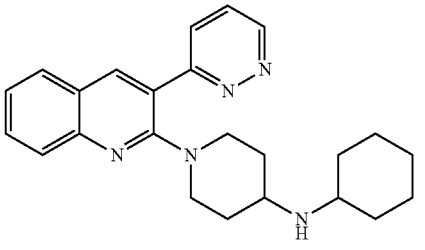 [SMILES: c1cnnc(-c2cc3ccccc3nc2N2CCC(NC3CCCCC3)CC2)c1] | 87 |

US 9,682,966 B2
TABLE I-continued
Compounds of the Invention
| Cpd. # | Structure | IC$_{50}$ nM (% inhib if other than 50%) |
|---|---|---|
| 465 | 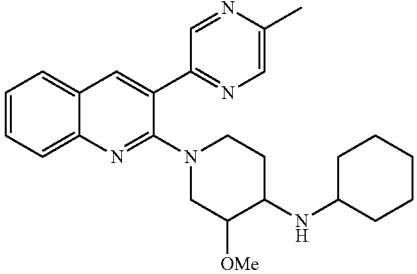<br>cis-rac | 18 |
| 466 | 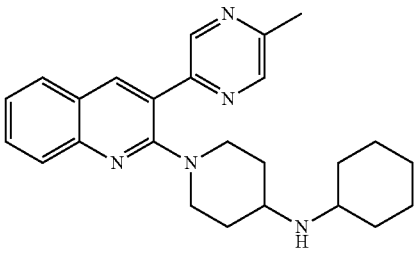 [SMILES: Cc1cnc(-c2cc3ccccc3nc2N2CCC(NC3CCCCC3)CC2)cn1] | 24 |
| 467 | 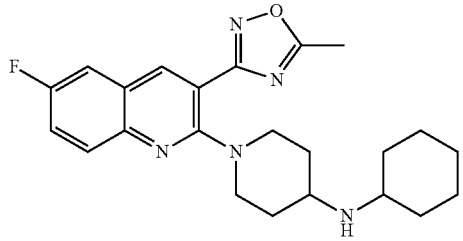 [SMILES: Cc1nc(-c2cc3cc(F)ccc3nc2N2CCC(NC3CCCCC3)CC2)no1] | 431 |
| 468 | 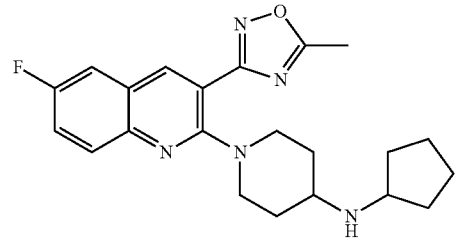 [SMILES: Cc1nc(-c2cc3cc(F)ccc3nc2N2CCC(NC3CCCC3)CC2)no1] | 175 |
| 469 | 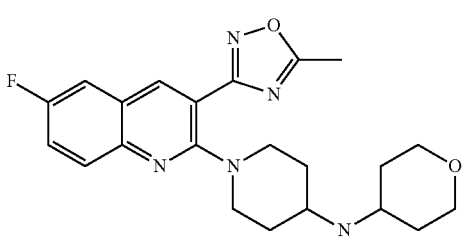 | 440 |

TABLE I-continued
Compounds of the Invention
| Cpd. # | Structure | IC$_{50}$ nM (% inhib if other than 50%) |
|---|---|---|
| 470 | 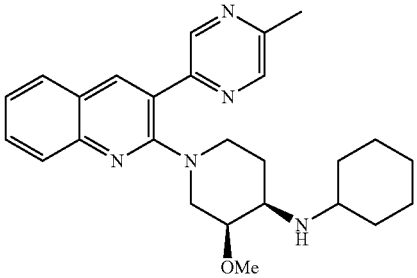 [SMILES: CO[C@H]1CN(c2nc3ccccc3cc2-c2cnc(C)cn2)CC[C@H]1NC1CCCCC1] | 40 |
| 471 | 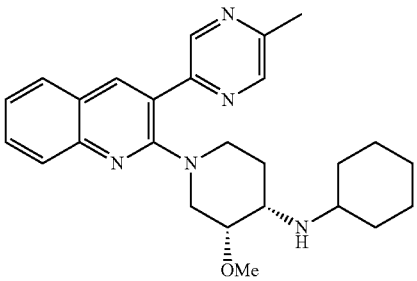 [SMILES: CO[C@@H]1CN(c2nc3ccccc3cc2-c2cnc(C)cn2)CC[C@@H]1NC1CCCCC1] | 170 |
| 472 | 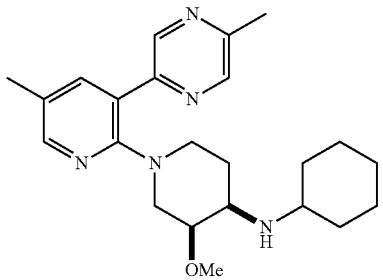 [SMILES: CO[C@H]1CN(c2ncc(C)cc2-c2cnc(C)cn2)CC[C@H]1NC1CCCCC1] | 105 |
| 473 | 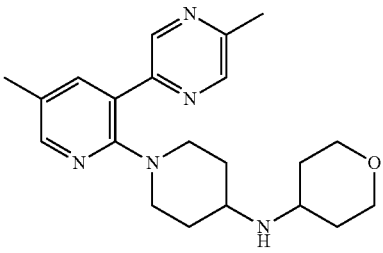 [SMILES: Cc1cnc(N2CCC(NC3CCOCC3)CC2)c(-c2cnc(C)cn2)c1] | 3210 |
| 474 | 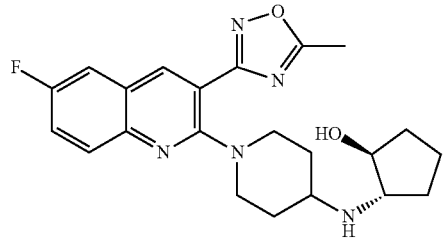 [SMILES: Cc1nc(-c2cc3cc(F)ccc3nc2N2CCC(N[C@H]3CCC[C@@H]3O)CC2)no1] | 1900 |

TABLE I-continued

Compounds of the Invention

| Cpd. # | Structure | IC$_{50}$ nM (% inhib if other than 50%) |
|---|---|---|
| 475 | 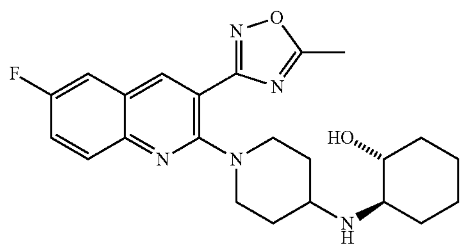 [SMILES: Cc1nc(-c2cc3cc(F)ccc3nc2N2CCC(N[C@@H]3CCCC[C@H]3O)CC2)no1] | 101 |
| 476 | 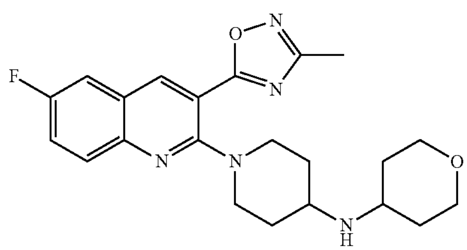 [SMILES: Cc1noc(-c2cc3cc(F)ccc3nc2N2CCC(NC3CCOCC3)CC2)n1] | 430 |
| 477 | 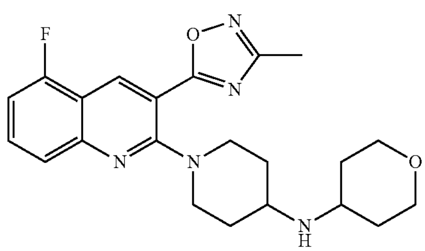 [SMILES: Cc1noc(-c2cc3c(F)cccc3nc2N2CCC(NC3CCOCC3)CC2)n1] | 42 |
| 478 | 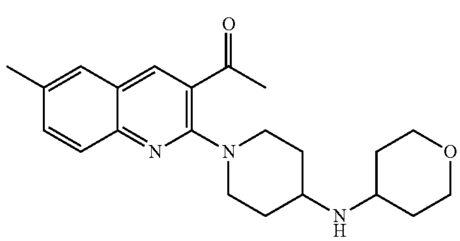 [SMILES: CC(=O)c1cc2cc(C)ccc2nc1N1CCC(NC2CCOCC2)CC1] | 900 |
| 479 | 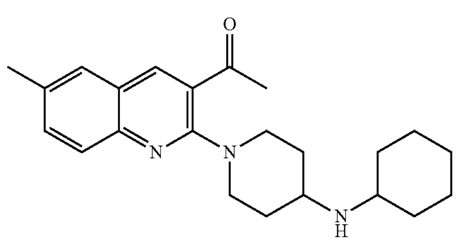 [SMILES: CC(=O)c1cc2cc(C)ccc2nc1N1CCC(NC2CCCCC2)CC1] | 211 |
| 480 | 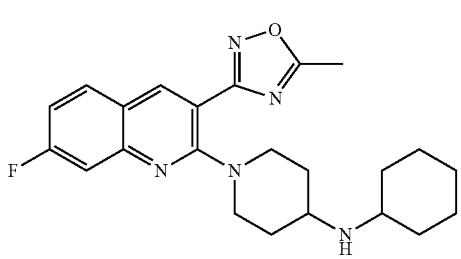 [SMILES: Cc1nc(-c2cc3ccc(F)cc3nc2N2CCC(NC3CCCCC3)CC2)no1] | 8 |

TABLE I-continued
Compounds of the Invention
| Cpd. # | Structure | IC$_{50}$ nM (% inhib if other than 50%) |
|---|---|---|
| 481 | 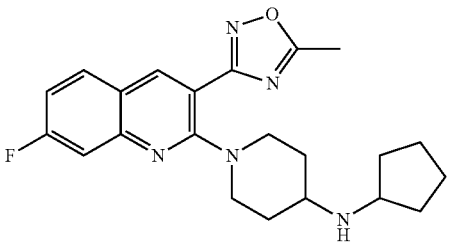 [SMILES: Cc1nc(-c2cc3ccc(F)cc3nc2N2CCC(NC3CCCC3)CC2)no1] | 10 |
| 482 | 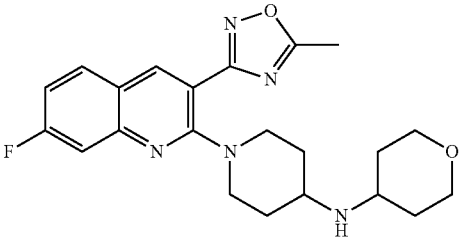 [SMILES: Cc1nc(-c2cc3ccc(F)cc3nc2N2CCC(NC3CCOCC3)CC2)no1] | 75 |
| 483 | 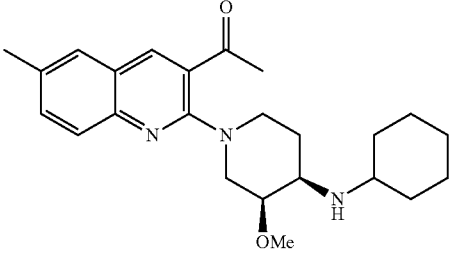 [SMILES: CO[C@H]1CN(c2nc3ccc(C)cc3cc2C(C)=O)CC[C@H]1NC1CCCCC1] | 315 |
| 484 | 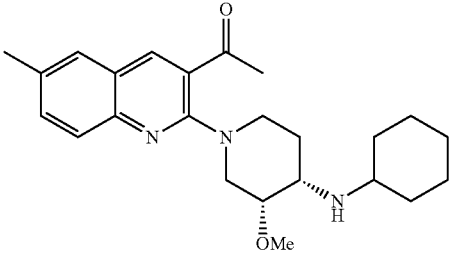 [SMILES: CO[C@@H]1CN(c2nc3ccc(C)cc3cc2C(C)=O)CC[C@@H]1NC1CCCCC1] | 347 |
| 485 | 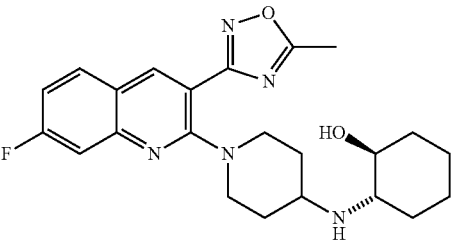 | 673 |

TABLE I-continued

Compounds of the Invention

| Cpd. # | Structure | IC$_{50}$ nM (% inhib if other than 50%) |
|---|---|---|
| 486 | 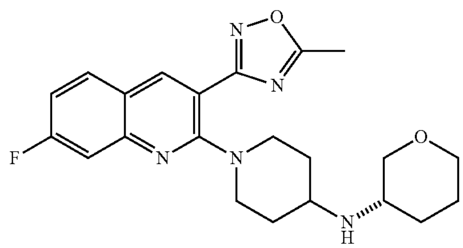 | 1070 |
| 487 | 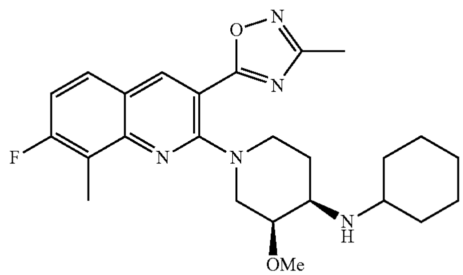 [SMILES: CO[C@H]1CN(c2nc3c(C)c(F)ccc3cc2-c2nc(C)no2)CC[C@H]1NC1CCCCC1] | 15 |
| 488 | 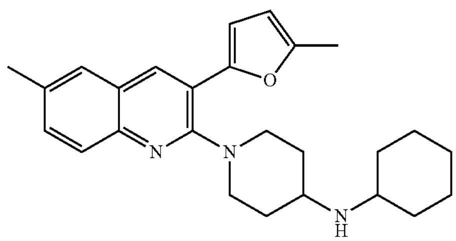 [SMILES: Cc1ccc2nc(N3CCC(NC4CCCCC4)CC3)c(-c3ccc(C)o3)cc2c1] | 19 |
| 489 | 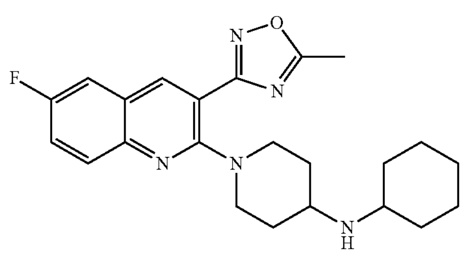 [SMILES: Cc1nc(-c2cc3cc(F)ccc3nc2N2CCC(NC3CCCCC3)CC2)no1] | 616 |
| 490 | 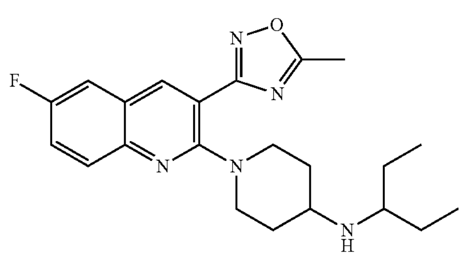 [SMILES: CCC(CC)NC1CCN(c2nc3ccc(F)cc3cc2-c2noc(C)n2)CC1] | 248 |
| 491 | 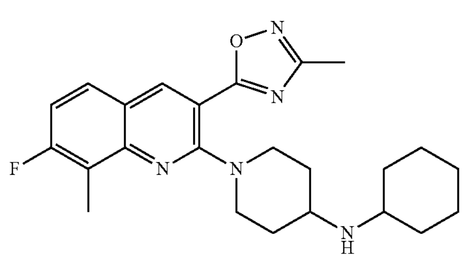 [SMILES: Cc1noc(-c2cc3ccc(F)c(C)c3nc2N2CCC(NC3CCCCC3)CC2)n1] | 33 |

TABLE I-continued

Compounds of the Invention

| Cpd. # | Structure | IC$_{50}$ nM (% inhib if other than 50%) |
|---|---|---|
| 492 | 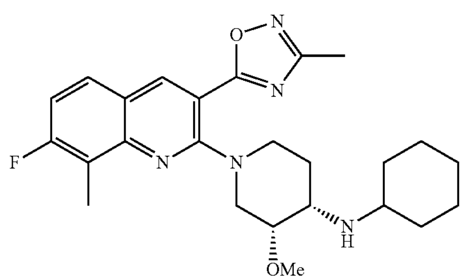 [SMILES: CO[C@@H]1CN(c2nc3c(C)c(F)ccc3cc2-c2nc(C)no2)CC[C@@H]1NC1CCCCC1] | 74 |
| 493 | 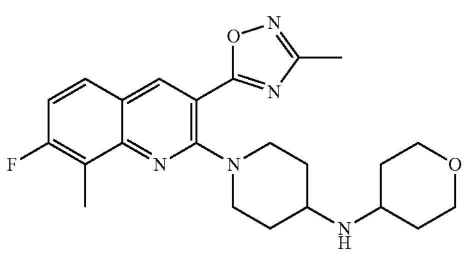 [SMILES: Cc1noc(-c2cc3ccc(F)c(C)c3nc2N2CCC(NC3CCOCC3)CC2)n1] | 132 |
| 494 | 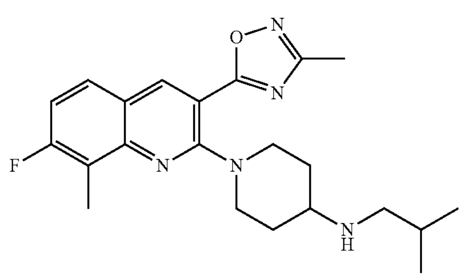 [SMILES: Cc1noc(-c2cc3ccc(F)c(C)c3nc2N2CCC(NCC(C)C)CC2)n1] | 64 |
| 495 | 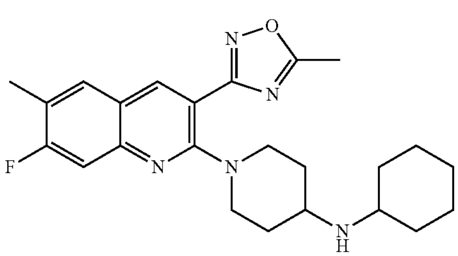 [SMILES: Cc1nc(-c2cc3cc(C)c(F)cc3nc2N2CCC(NC3CCCCC3)CC2)no1] | 13 |
| 496 | 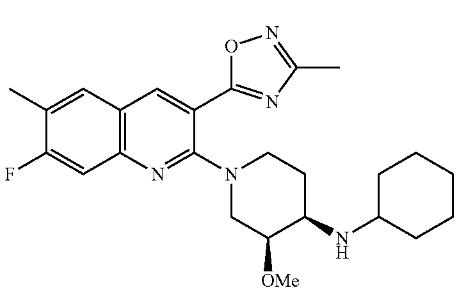 [SMILES: CO[C@H]1CN(c2nc3cc(F)c(C)cc3cc2-c2nc(C)no2)CC[C@H]1NC1CCCCC1] | 54 |

TABLE I-continued

Compounds of the Invention

| Cpd. # | Structure | IC$_{50}$ nM (% inhib if other than 50%) |
|---|---|---|
| 497 | 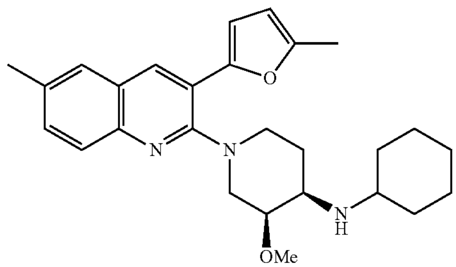 [SMILES: CO[C@H]1CN(c2nc3ccc(C)cc3cc2-c2ccc(C)o2)CC[C@H]1NC1CCCCC1] | 48 |
| 498 | 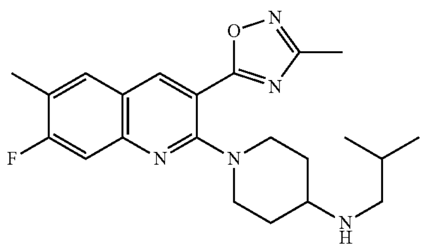 [SMILES: Cc1noc(-c2cc3cc(C)c(F)cc3nc2N2CCC(NCC(C)C)CC2)n1] | 33 |
| 499 | 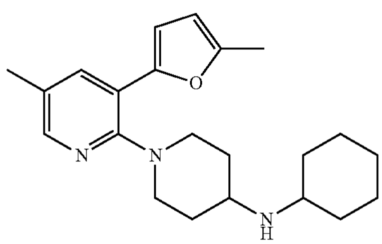 [SMILES: Cc1cnc(N2CCC(NC3CCCCC3)CC2)c(-c2ccc(C)o2)c1] | 116 |
| 500 | 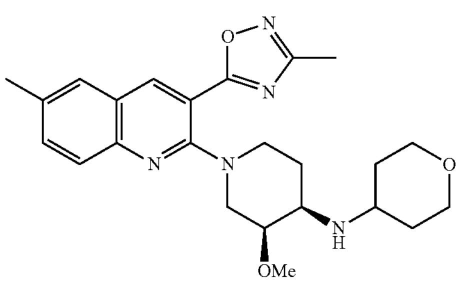 [SMILES: CO[C@H]1CN(c2nc3ccc(C)cc3cc2-c2nc(C)no2)CC[C@H]1NC1CCOCC1] | 423 |
| 501 | 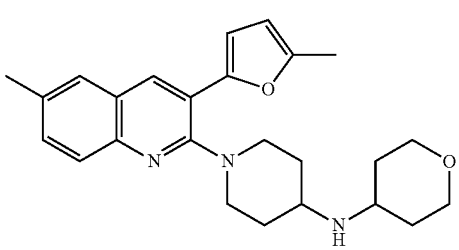 [SMILES: Cc1ccc2nc(N3CCC(NC4CCOCC4)CC3)c(-c3ccc(C)o3)cc2c1] | 331 |

TABLE I-continued
Compounds of the Invention
| Cpd. # | Structure | IC$_{50}$ nM (% inhib if other than 50%) |
|---|---|---|
| 502 | 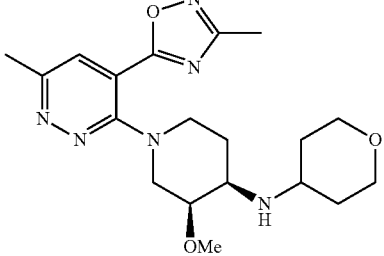 | 3109 |
| 503 | 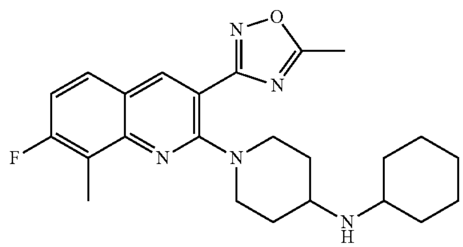 [SMILES: Cc1nc(-c2cc3ccc(F)c(C)c3nc2N2CCC(NC3CCCCC3)CC2)no1] | 74 |
| 504 | 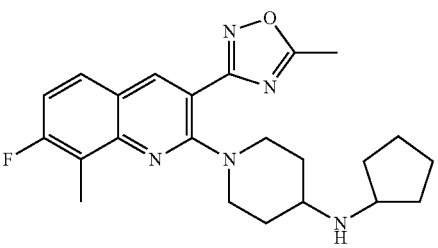 [SMILES: Cc1nc(-c2cc3ccc(F)c(C)c3nc2N2CCC(NC3CCCC3)CC2)no1] | 45 |
| 505 | 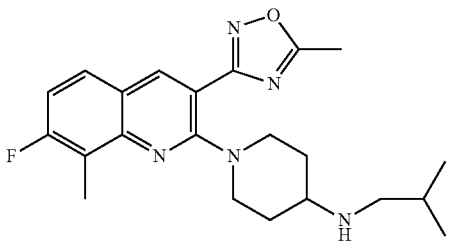 [SMILES: Cc1nc(-c2cc3ccc(F)c(C)c3nc2N2CCC(NCC(C)C)CC2)no1] | 126 |
| 506 | 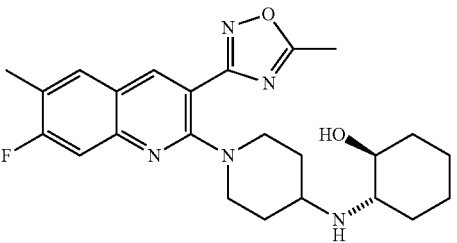 | 48 |
| 507 | 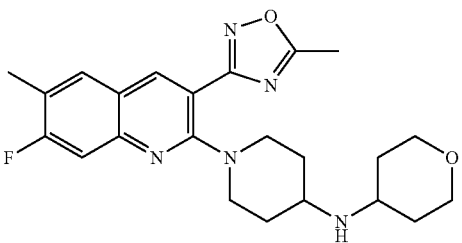 [SMILES: Cc1nc(-c2cc3cc(C)c(F)cc3nc2N2CCC(NC3CCOCC3)CC2)no1] | 43 |

TABLE I-continued

Compounds of the Invention

| Cpd. # | Structure | IC$_{50}$ nM (% inhib if other than 50%) |
|---|---|---|
| 508 | 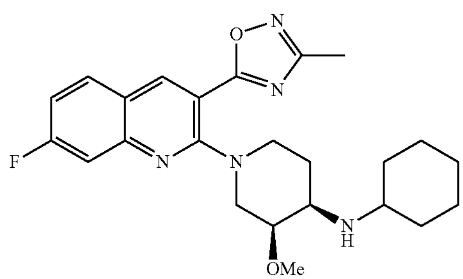 [SMILES: CO[C@H]1CN(c2nc3cc(F)ccc3cc2-c2nc(C)no2)CC[C@H]1NC1CCCCC1] | 5 |
| 509 | 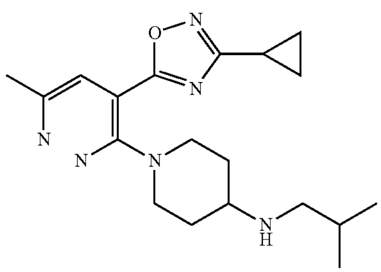 [SMILES: C/C(N)=C/C(=C(\N)N1CCC(NCC(C)C)CC1)c1nc(C2CC2)no1] | 30 |
| 510 | 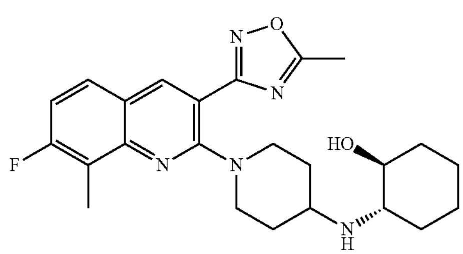 [SMILES: Cc1nc(-c2cc3ccc(F)c(C)c3nc2N2CCC(N[C@H]3CCCC[C@@H]3O)CC2)no1] | 115 |
| 511 | 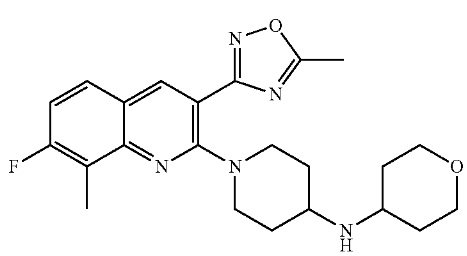 [SMILES: Cc1nc(-c2cc3ccc(F)c(C)c3nc2N2CCC(NC3CCOCC3)CC2)no1] | 227 |
| 512 | 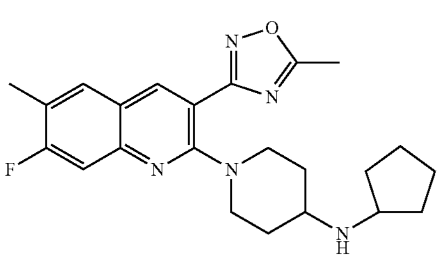 [SMILES: Cc1nc(-c2cc3cc(C)c(F)cc3nc2N2CCC(NC3CCCC3)CC2)no1] | 12 |

TABLE I-continued

Compounds of the Invention

| Cpd. # | Structure | IC$_{50}$ nM (% inhib if other than 50%) |
|---|---|---|
| 513 | 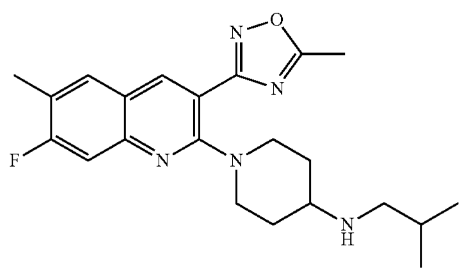 [SMILES: Cc1nc(-c2cc3cc(C)c(F)cc3nc2N2CCC(NCC(C)C)CC2)no1] | 27 |
| 514 | 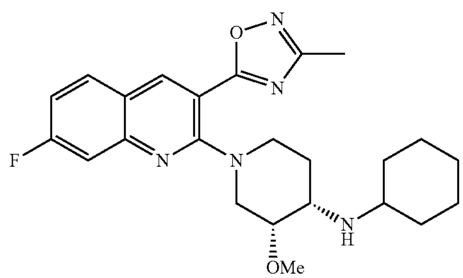 [SMILES: CO[C@@H]1CN(c2nc3cc(F)ccc3cc2-c2nc(C)no2)CC[C@@H]1NC1CCCCC1] | 55 |
| 515 | 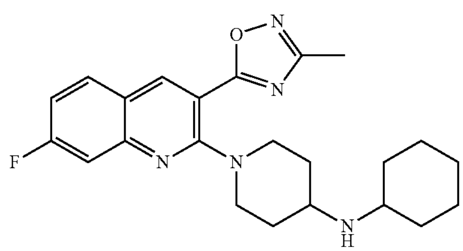 [SMILES: Cc1noc(-c2cc3ccc(F)cc3nc2N2CCC(NC3CCCCC3)CC2)n1] | 7 |
| 516 | 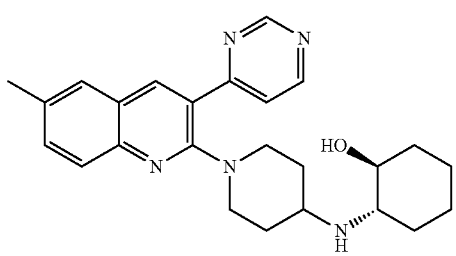 [SMILES: Cc1ccc2nc(N3CCC(N[C@H]4CCCC[C@@H]4O)CC3)c(-c3ccncn3)cc2c1] | 564 |
| 517 | 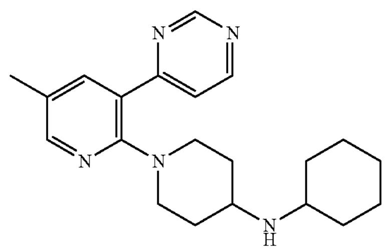 [SMILES: Cc1cnc(N2CCC(NC3CCCCC3)CC2)c(-c2ccncn2)c1] | 1142 |

261
262
TABLE I-continued
Compounds of the Invention
| Cpd. # | Structure | IC$_{50}$ nM (% inhib if other than 50%) |
|---|---|---|
| 518 | 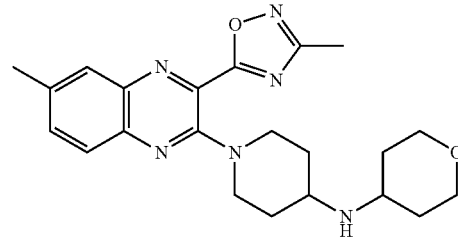 | 410 |
| 519 | 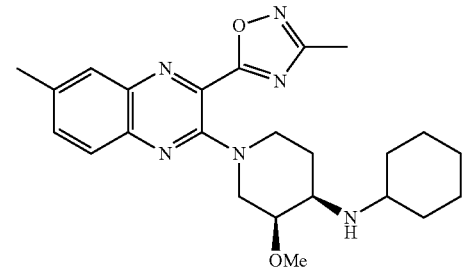 [SMILES: CO[C@H]1CN(c2nc3ccc(C)cc3nc2-c2nc(C)no2)CC[C@H]1NC1CCCCC1] | 95 |
| 520 | 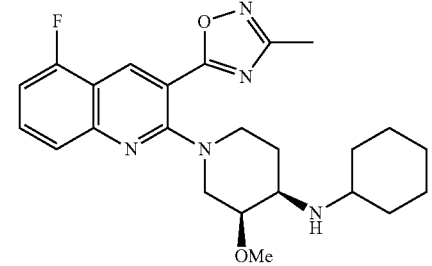 [SMILES: CO[C@H]1CN(c2nc3cccc(F)c3cc2-c2nc(C)no2)CC[C@H]1NC1CCCCC1] | 19 |
| 521 | 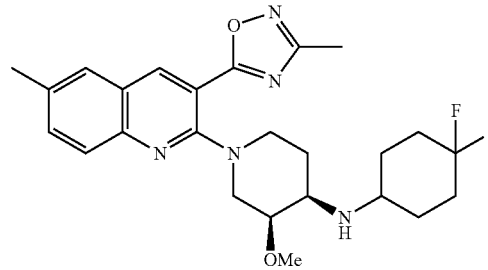 | 278 |
| 522 | 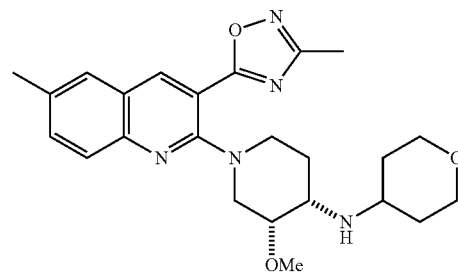 | 67 |

TABLE I-continued
Compounds of the Invention
| Cpd. # | Structure | IC$_{50}$ nM (% inhib if other than 50%) |
|---|---|---|
| 523 | 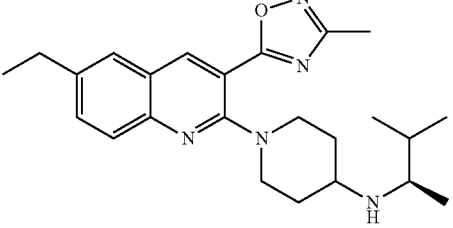 | 7 |
| 524 | 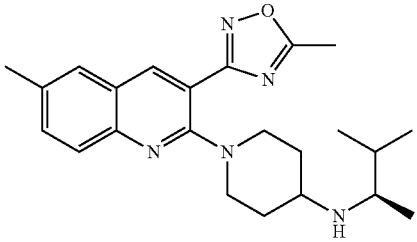 [SMILES: Cc1ccc2nc(N3CCC(N[C@H](C)C(C)C)CC3)c(-c3noc(C)n3)cc2c1] | 57 |
| 525 | 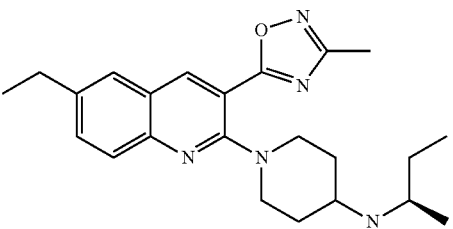 | 17 |
| 526 | 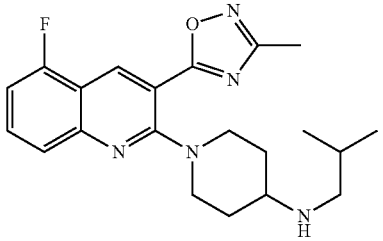 [SMILES: Cc1noc(-c2cc3c(F)cccc3nc2N2CCC(NCC(C)C)CC2)n1] | 49 |
| 527 | 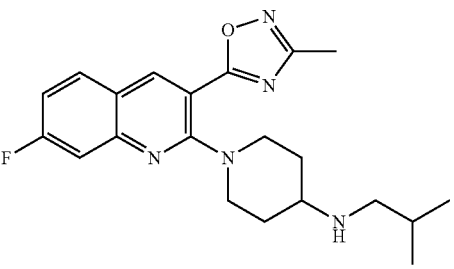 [SMILES: Cc1noc(-c2cc3ccc(F)cc3nc2N2CCC(NCC(C)C)CC2)n1] | 20 |
| 528 | 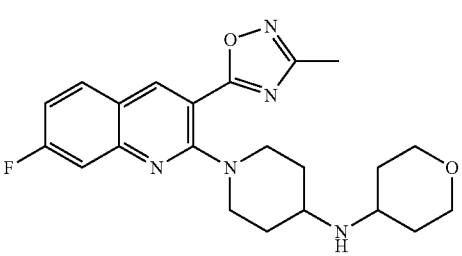 [SMILES: Cc1noc(-c2cc3ccc(F)cc3nc2N2CCC(NC3CCOCC3)CC2)n1] | 23 |

TABLE I-continued

Compounds of the Invention

| Cpd. # | Structure | IC$_{50}$ nM (% inhib if other than 50%) |
|---|---|---|
| 529 | 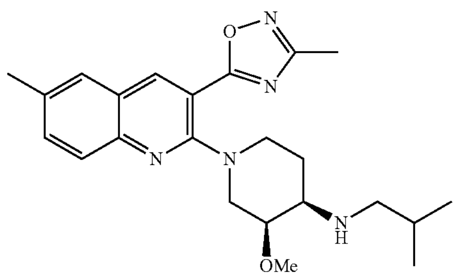 [SMILES: CO[C@H]1CN(c2nc3ccc(C)cc3cc2-c2nc(C)no2)CC[C@H]1NCC(C)C] | 369 |
| 530 | 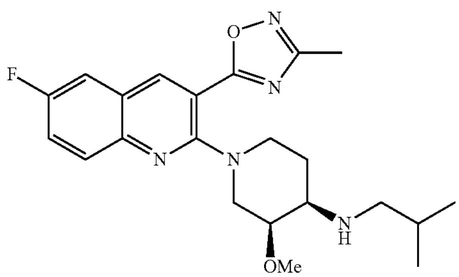 [SMILES: CO[C@H]1CN(c2nc3ccc(F)cc3cc2-c2nc(C)no2)CC[C@H]1NCC(C)C] | 5100 |
| 531 | 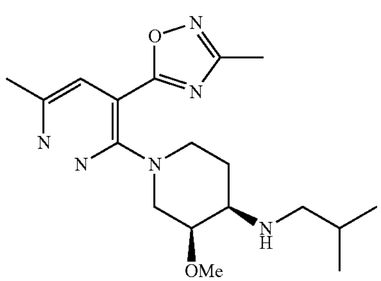 [SMILES: CO[C@H]1CN(/C(N)=C(/C=C(/C)N)c2nc(C)no2)CC[C@H]1NCC(C)C] | 996 |
| 532 | 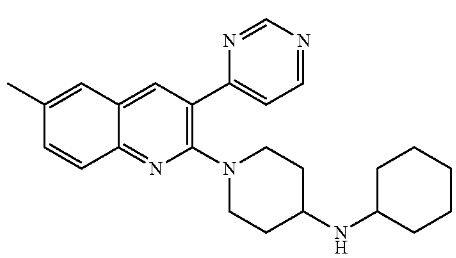 [SMILES: Cc1ccc2nc(N3CCC(NC4CCCCC4)CC3)c(-c3ccncn3)cc2c1] | 334 |
| 533 | 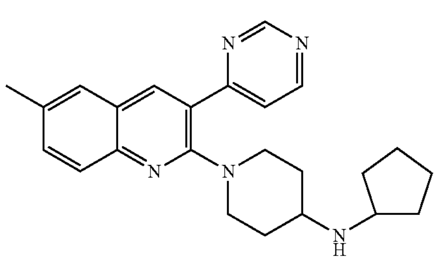 [SMILES: Cc1ccc2nc(N3CCC(NC4CCCC4)CC3)c(-c3ccncn3)cc2c1] | 263 |

TABLE I-continued

Compounds of the Invention

| Cpd. # | Structure | IC$_{50}$ nM (% inhib if other than 50%) |
|---|---|---|
| 534 | 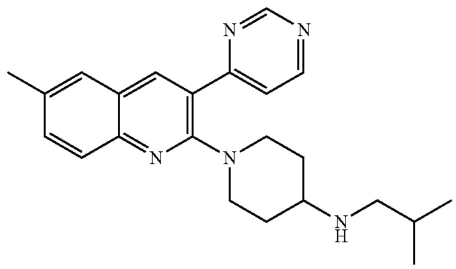 [SMILES: Cc1ccc2nc(N3CCC(NCC(C)C)CC3)c(-c3ccncn3)cc2c1] | 600 |
| 535 | 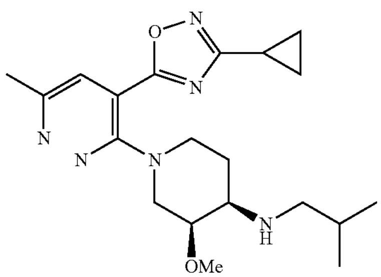 [SMILES: CO[C@H]1CN(/C(N)=C(/C=C(/C)N)c2nc(C3CC3)no2)CC[C@H]1NCC(C)C] | 465 |
| 536 | 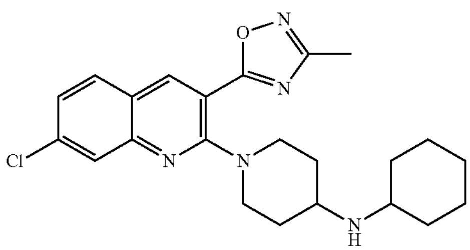 [SMILES: Cc1noc(-c2cc3ccc(Cl)cc3nc2N2CCC(NC3CCCCC3)CC2)n1] | 19 |
| 537 | 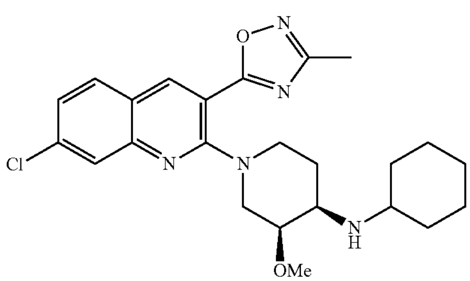 [SMILES: CO[C@H]1CN(c2nc3cc(Cl)ccc3cc2-c2nc(C)no2)CC[C@H]1NC1CCCCC1] | 12 |
| 538 | 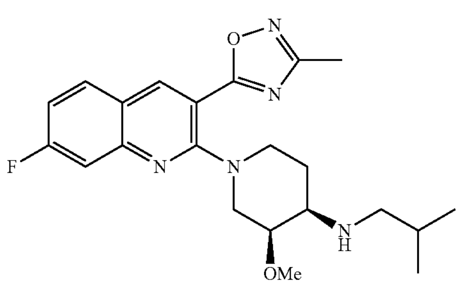 [SMILES: CO[C@H]1CN(c2nc3cc(F)ccc3cc2-c2nc(C)no2)CC[C@H]1NCC(C)C] | 970 |

TABLE I-continued
Compounds of the Invention
| Cpd. # | Structure | IC$_{50}$ nM (% inhib if other than 50%) |
|---|---|---|
| 539 | 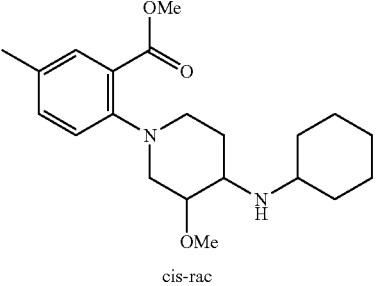 [SMILES: COC(=O)c1cc(C)ccc1N1CCC(NC2CCCCC2)C(OC)C1] cis-rac | 3700 |
| 540 | 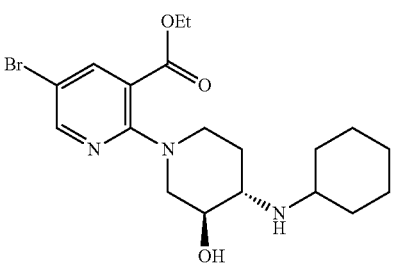 [SMILES: CCOC(=O)c1cc(Br)cnc1N1CC[C@H](NC2CCCCC2)[C@@H](O)C1] | 16 |
| 541 | 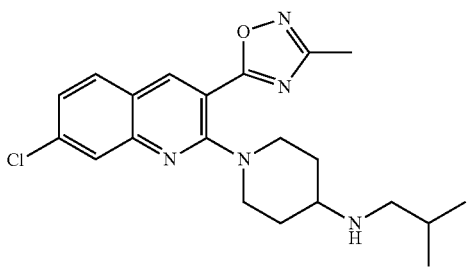 [SMILES: Cc1noc(-c2cc3ccc(Cl)cc3nc2N2CCC(NCC(C)C)CC2)n1] | 45 |
| 542 | 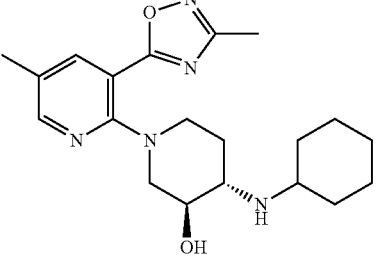 | 32 |
| 543 | 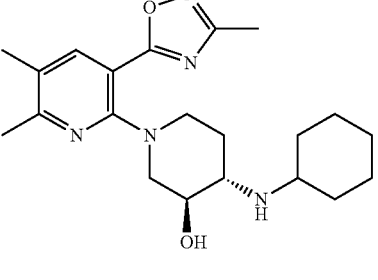 | 32 |

TABLE I-continued

Compounds of the Invention

| Cpd. # | Structure | IC$_{50}$ nM (% inhib if other than 50%) |
| --- | --- | --- |
| 544 | [structure: 5-bromo-2-(3-hydroxy-4-(cyclohexylamino)piperidin-1-yl)nicotinic acid methyl ester] | 10 |

Me = methyl, Et = ethyl, Boc = t-butoxycarbonyl, Ph = phenyl, iPr = isopropyl, straight or wavy line = either stereochemical option unless otherwise specified, bold line or solid wedge = bond "up", hashed line or hashed wedge = bond "down",
Cis-rac = racemic mixture of two cis isomers.
Trans-rac = racemic mixture of two trans isomers.
NA = not active at concentrations up to 10 μM.
C# = comparative compound, IC50 > 10 μM Methods of Synthesis The following abbreviations are used throughout this document.
Ac acetyl
AcOH acetic acid
Boc tert-Butoxycarbonyl
Bn benzyl
Bz benzoyl
BOP Benzotriazol-1-yl-oxy-tris-(dimethylamino)phosphonium hexafluorophosphate
Cbz benzyloxycarbonyl
CC column chromatography
CDI Carbonyl diimidazole
DBU Diazabicycloundecane
DCM Dichloromethane
DIAD Diisopropylazodicarboxylate
DIPEA, $^i$Pr$_2$EtN N,N-Diisopropylethylamine
DMAP 4-(N,N-dimethylamino)pyridine
DMF N,N-Dimethylformamide
DMSO Dimethylsulfoxide
EDAC, EDCI 1-Ethyl-3-(3-dimethylaminopropyl)carbodiimide hydrochloride
eq, equiv Equivalents
Et$_2$O Diethyl ether
EtOAc Ethyl acetate
h, hr Hours
HATU O-(7-Azabenzotriazole-1-yl)-N,N,N'N'-tetramethyluronium PF$_6^-$
HCl Hydrochloric acid
HOAT Hydroxyazabenztriazole
HOBt Hydroxybenzotriazole
LiHDMS Lithium hexamethyldisilazide
LiOH Lithium hydroxide
mg Milligrams
min Minutes
mL Milliliters
μL Microliters
mM millimolar
μM micromolar
μw microwave heating
nM nanomolar
mmole Millimoles
MS Mass spectroscopy
MeOH Methanol
NaBH$_3$CN Sodium cyanoborohydride
NaH Sodium hydride
NaIO$_4$ Sodium periodate
NMM N-Methylmorpholine
rb Round-bottom
RT Room temperature
sat. Saturated
TEA Triethylamine
TFA Trifluoroacetic acid
THF Tetrahydrofuran
~ approximately (~10° C.) or, to (range, e.g., X~Y=X to Y)

Example 1. Synthesis of Compound 5

-continued

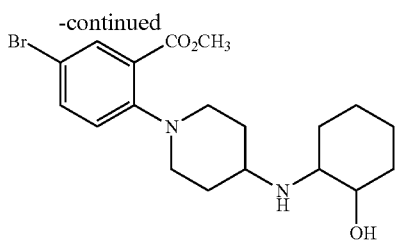

5 a) I (1.1 equiv.) plus II (1 equiv.), Bi(OTf)₃·4H₂O (0.01 equiv.), microwave 150° C., 30 min.
b) TFA (20 equiv.), CH₂Cl₂, rt, 30 min.
c) III (1 equiv.) plus IV (1.2 equiv.), DIPEA (1.2 equivl) EtOH, microwave, 150° C., 35 min.

In a capped microwave vial, a mixture of N-Boc-4aminopiperidine I, epoxide II, and Bi(OTf)₃.4H₂O was heated at 150° C. for 30 min under microwave irradiation. Upon addition of ethyl ether, the reaction mixture was stirred for 5 minutes, then filtered over celite, washed with ethyl ether and concentrated under vacuum. The residue was dissolved in ethyl acetate and washed with brine (2×).

To the product N-Boc-protected aminoalcohol dissolved in CH₂Cl₂ was added TFA at room temperature. The reaction mixture was stirred for 30 min, then concentrated under reduced pressure. The residue was dissolved in 1M NaOH and the product extracted with EtOAc (5×). The organic phase was dried over sodium sulfate and concentrated under reduced pressure. The product was purified by column chromatography (CC) using CH₂Cl₂/MeOH to furnish amino alcohol III.

In a microwave vial a solution of III, pyridine IV and DIPEA in ethanol was heated at 150° C. for 35 min under microwave irradiation. The organic solvent was removed under reduced pressure and the product was purified by CC using CH₂Cl₂/MeOH to afford Compound 5.

Example 2. Synthesis of Compound 33

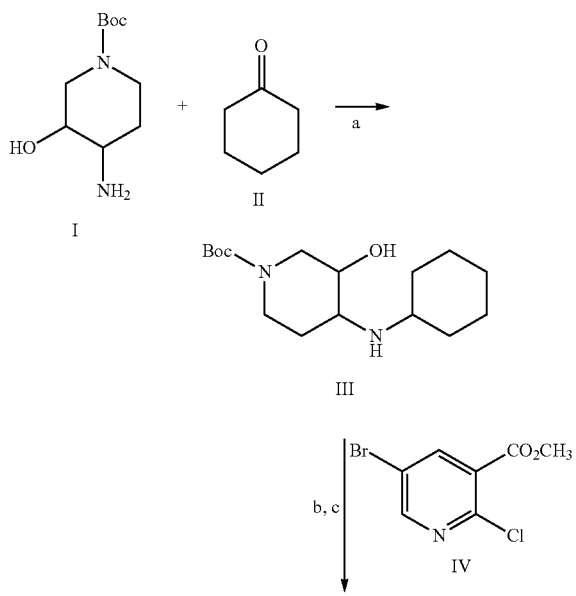

-continued

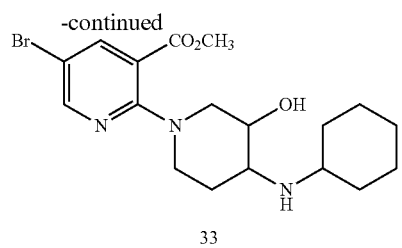

33

Reagents and Conditions: (a) I (1 equiv.) plus II (1.3 equivl), NaBH(OAc)₃ (1.5 equiv.), AcOH (1.5 equiv.), DCE, rt, 12 hr; (b) III (1 equiv.), TFA (20 equiv.) CH₂Cl₂, rt, 30 min; (c) IV (1 equiv.), DIPEA (2 equiv.), microwave, 145° C., 35 min.

To a stirred solution of N-Boc-4aminopiperidine I and cyclohexanone II in DCE were added NaBH(OAc)₃ and AcOH. The reaction mixture was stirred for 12 h at room temperature. The mixture was diluted with ethyl acetate and washed with brine (2×). The organic phase was concentrated, and the product purified by CC using CH₂Cl₂/MeOH (9:1) furnishing amine III.

To a solution of III in CH₂Cl₂ was added TFA and the reaction mixture was stirred for 30 min at room temperature. The mixture was concentrated under reduced pressure, diluted in ethanol followed by addition of DIPEA and pyridine IV. The reaction mixture was heated at 145° C. for 35 min under microwave irradiation. The crude was concentrated under reduced pressure and the product purified by HPLC furnishing the pure Compound 33.

Example 3. Synthesis of Compound 7

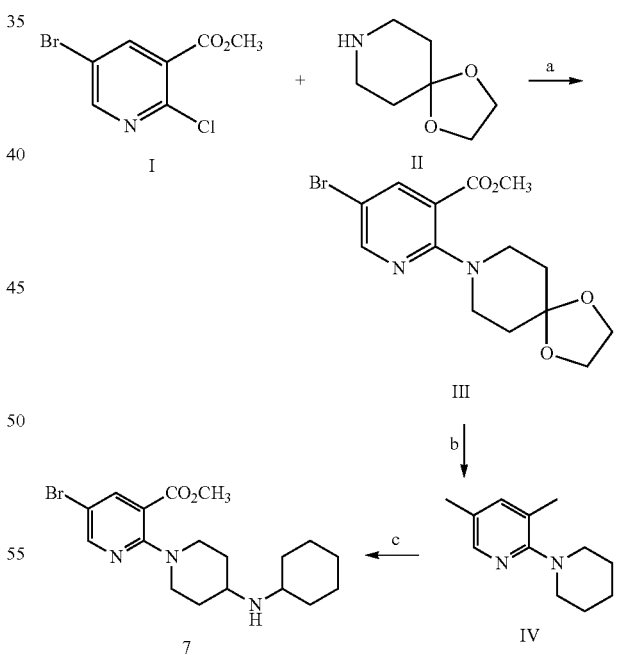

Reagents and Conditions: (a) I (1 equiv.) plus II (1 equiv.), DIPEA (1 equiv.) EtOH, microwave, 125° C., 45 min; (b) 5% HCl, THF, 40° C., 6 hr; (c) IV (1 equivl) plus cyclohexylamine (1.2 equiv.), NaBH(OAc)₃ (1.5 equiv.), AcOH (1.5 equiv.), DCE, rt, 16 hr.

In a microwave vial pyridine I, 4-piperidinone ethyl ketal II and DIPEA were dissolved in ethanol and heated at 125° C. for 45 min under microwave irradiation. The organic solvent was removed under reduced pressure and the product was purified by CC using CH$_2$Cl$_2$/MeOH to afford the pyridine derivative III.

A solution of III in THF was added to 5% HCl and heated at 40° C. for 6 h. The organic solvent was removed under reduced pressure. The crude was dissolved in ethyl acetate and washed with 0.5M NaOH (2×). The organic solvent was dried over sodium sulfate and concentrated under reduced pressure. The product was purified by CC using hexanes/EtOAc to afford the ketone derivative IV.

To a stirred solution of IV, cyclohexylamine and AcOH in DCE was added at room temperature NaBH(OAc)$_3$. The reaction was stirred for 16 h at room temperature. Upon reaction completion the mixture was diluted in ethyl acetate and washed with brine (2×). The organic phase was dried over sodium sulfate and the product purified by CC using CH$_2$Cl$_2$/MeOH to furnish Compound 7.

Example 4. Synthesis of Compound 235

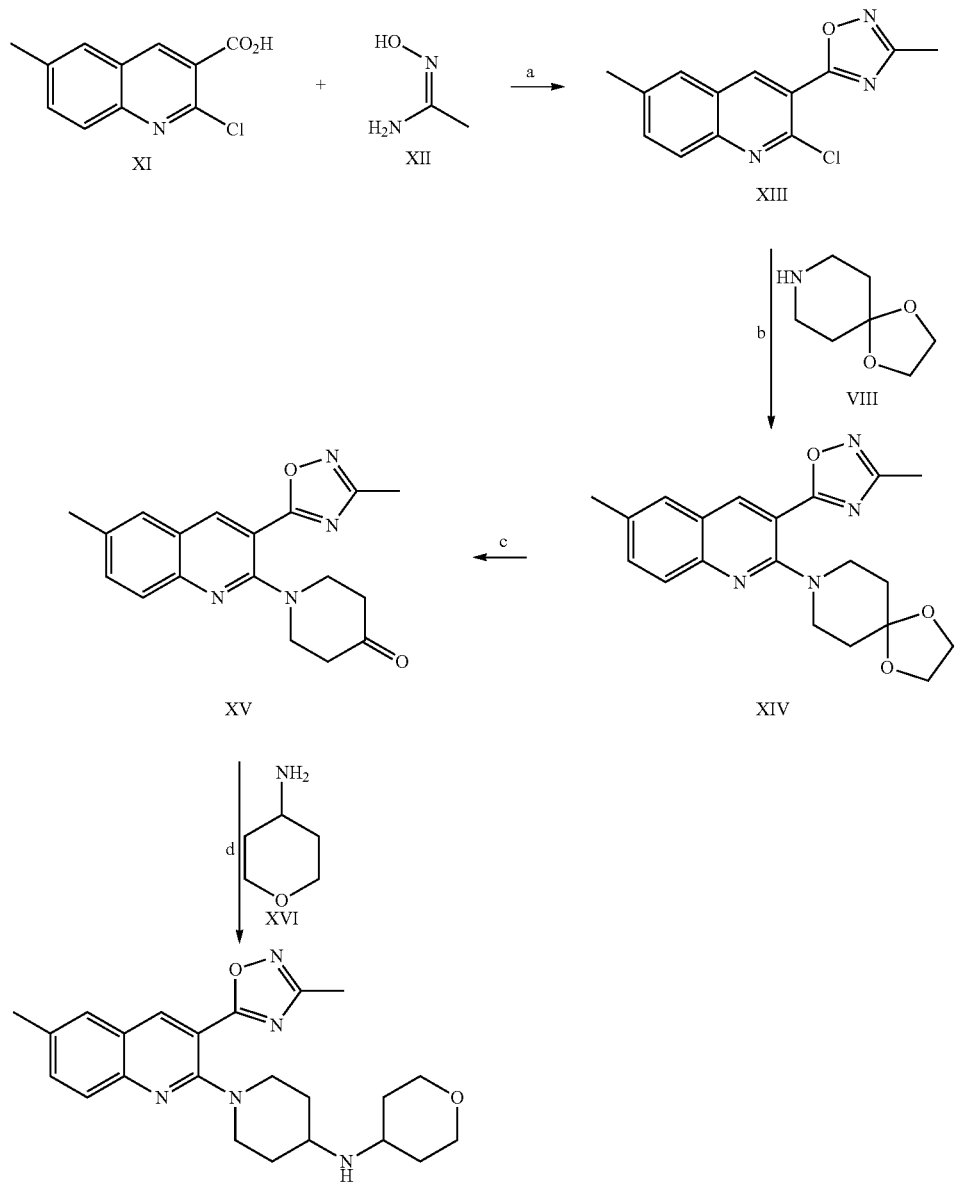

Reagents and conditions: (a) XI (1 equiv.), XII (1.2 equivl), EDCI (1.3 equiv.), HOBt 91.3 equiv.), dioxane, rt to 100° C., μw, 35 min, 70%; (b) XIII (1 equiv.), VIII (1.2 equiv.), DIPEA (1 equiv.), EtOH, μw, 125° C., 45 min, 85%; (c) XIV (1 equiv.), 5% HCl, THF, 40° C., 6 hr, 62%; (d) XV (1 equiv.), XVI (1.2 equiv.), NaBH(OAc)$_3$ (1.5 equiv.), AcOH (1.5 equiv.), DCE, rt, 5 hr, 76%

In a microwave vial, a stirring solution of acid XI in 1,4-dioxane was treated with HOBt and EDCI at room temperature. The reaction was stirred for 20 min followed by addition, in a single portion, of amidoxime XII. The reaction was stirred for additional 30 min at room temperature and then heated to 100° C. under microwave irradiation for 35 min. The reaction mixture was diluted with EtOAc and washed with brine (2×). The organic phase was dried over Na₂SO₄ anhydrous and concentrated under reduced pressure. The product was purified by C.C. using CH₂Cl₂:MeOH (99:1) to furnish XIII in 70% yield.

In a microwave vial quinoline XIII, 4-piperidinone ethyl ketal VIII and DIPEA were dissolved in ethanol and heated at 125° C. for 45 min under microwave irradiation. The organic solvent was removed under reduced pressure and the product was purified by CC using CH₂Cl₂/MeOH to furnish quinoline XIV in 85% yield.

A solution of XIV in THF was added to 5% HCl and heated at 40° C. for 6 h. The solvent was removed under reduced pressure. The crude was dissolved in EtOAc and washed with 0.5M NaOH (2×). The organic solvent was dried over sodium sulfate and concentrated under reduced pressure. The product XV was purified by CC using hexanes/EtOAc in 62% yield.

To a stirred solution of XV, 4-aminotetrahydropyrane XVI and AcOH in DCE was added at room temperature NaBH(OAc)₃ and the mixture was stirred for 5 h at room temperature. The mixture was diluted in EtOAc and washed with brine (2×). The organic phase was dried over sodium sulfate and the product purified by CC using CH₂Cl₂/MeOH to furnish Compound 235 in 76% yield.

Example 5: Synthesis of 296

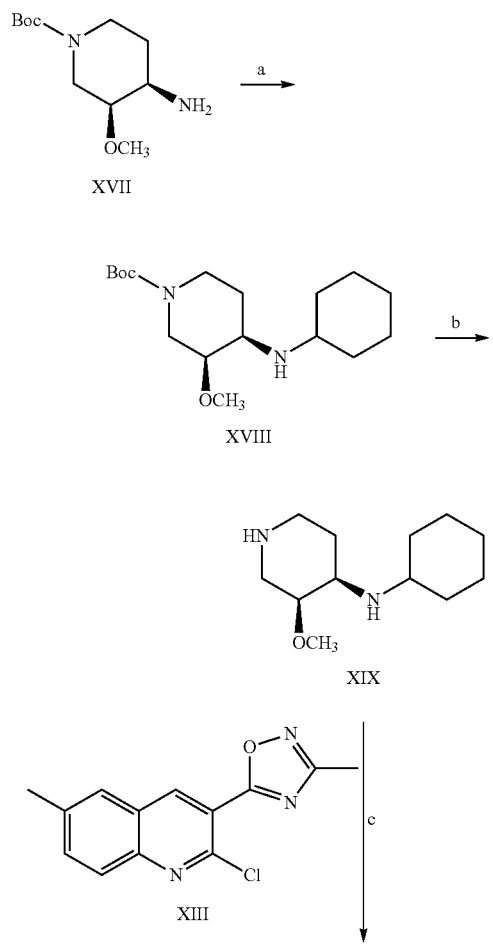

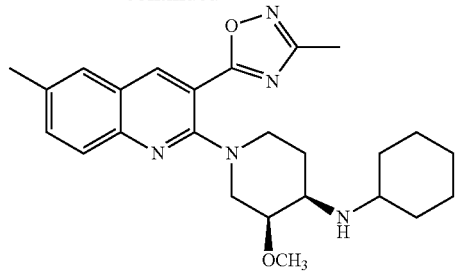

296

Reagents and conditions: (a) XVII (1.0 equiv.), cyclohexanone (1.4 equiv.), NaBH(OAc)₃ (1.4 equiv.), AcOH (1.4 equiv.), DCE, rt, overnight, 75%; (b) XVIII (1 equiv.), TFA (20 equiv.), CH₂Cl₂, rt, 30 min; (c) XIII (1.1 equiv.), DIPEA (2.2 equiv.), EtOH, μw, 130° C., 35 min, 65%.

To a stirred solution of (3S,4R)piperidine XVII and cyclohexanone in DCE were added NaBH(OAc)₃ and AcOH and the reaction mixture was stirred overnight at room temperature. The mixture was diluted with ethyl acetate and washed with brine (2×). The organic phase was concentrated, and the product purified by CC using CH₂Cl₂/MeOH (9:1) to furnish amine XVIII in 75% yield.

To a solution of XVIII in CH₂Cl₂ was added TFA and the reaction mixture was stirred for 30 min at room temperature. The mixture was concentrated under reduced pressure, diluted with EtOAc and washed with NaOH (1M). The aqueous phase was extracted with EtOAc (3×). The organic phase was concentrated under reduced pressure and the product XIX was used without further purification.

In a microwave vial, a solution of XIX, quinoline XIII and DIPEA in ethanol was heated at 130° C. for 35 min under microwave irradiation. The crude was concentrated under reduced pressure and the product purified by HPLC to furnish Compound CYM51427 in 65% yield.

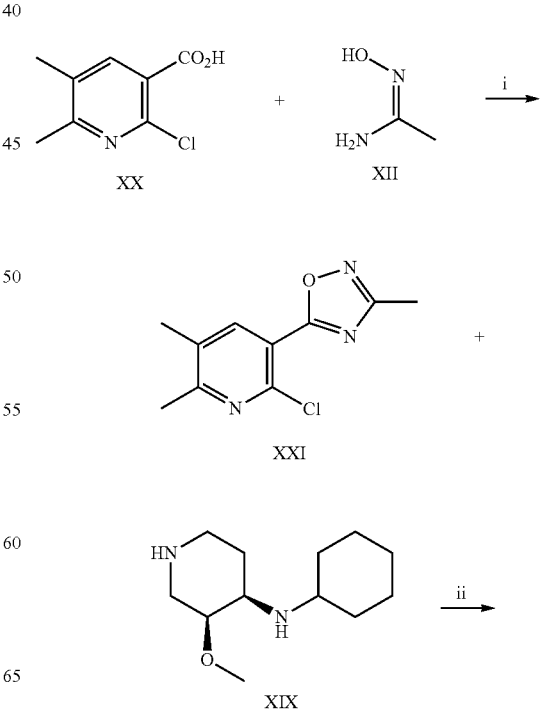

-continued

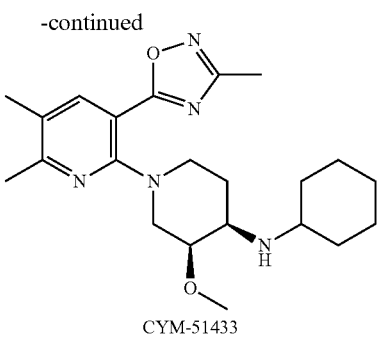

CYM-51433

Reagents and conditions: (i) (a) XX (1 equiv.), XII (1.2 equiv.), EDCI (1.3 equiv.), HOBt (1.3 equiv.), dioxane, 100° C., MW, 35 min; (ii) XXI (1 equiv.), XIX (1.2 equiv.), DIPEA (1 equiv.), EtOH, µw, 145° C., 2 h, 80%.

In a microwave vial, a stirring solution of acid XX in 1,4-dioxane was treated with HOBt and EDCI at room temperature. The reaction was stirred for 20 min followed by addition, in a single portion, of amidoxime XII. The reaction was stirred for additional 30 min at room temperature and then heated to 100° C. under microwave irradiation for 35 min. The reaction mixture was diluted with EtOAc and washed with brine (2×). The organic phase was dried over $Na_2SO_4$ anhydrous and concentrated under reduced pressure. The product XXI was purified by C.C. using $CH_2Cl_2$: MeOH (99:1).

In a microwave vial pyridine XXI, amine XIX and DIPEA were dissolved in ethanol and heated at 145° C. for 2 hours under microwave irradiation. The organic solvent was removed under reduced pressure and the product was purified by HPLC to furnish CYM51433.

Other compounds of formula (I) can be prepared by the person of ordinary skill using techniques and approaches described herein in conjunction with the chemical literature.
Pharmaceutical Compositions and Uses Another aspect of an embodiment of the invention provides compositions of the compounds of the invention, alone or in combination with another medicament. As set forth herein, compounds of the invention include stereoisomers, tautomers, solvates, prodrugs, pharmaceutically acceptable salts and mixtures thereof. Compositions containing a compound of the invention can be prepared by conventional techniques, e.g. as described in Remington: *The Science and Practice of Pharmacy,* 19th Ed., 1995, or later versions thereof, incorporated by reference herein. The compositions can appear in conventional forms, for example capsules, tablets, aerosols, solutions, suspensions or topical applications.

Typical compositions include a compound of the invention and a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances preserving agents, sweetening agents or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

If a solid carrier is used for oral administration, the preparation can be tableted, placed in a hard gelatin capsule in powder or pellet form or it can be in the form of a troche or lozenge. If a liquid carrier is used, the preparation can be in the form of a syrup, emulsion, soft gelatin capsule or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is non-volatile, including natural or synthetic oils, fatty acids, mono-, di- or tri-glycerides.

For injection, the formulation can also be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly(anhydrides).

For nasal administration, the preparation can contain a compound of the invention, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet that can be prepared by conventional tabletting techniques can contain:

| Core: | |
|---|---|
| Active compound (as free compound or salt thereof) | 250 mg |
| Colloidal silicon dioxide (Aerosil) ® | 1.5 mg |
| Cellulose, microcryst. (Avicel) ® | 70 mg |
| Modified cellulose gum (Ac-Di-Sol) ® | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

A typical capsule for oral administration contains compounds of the invention (250 mg), lactose (75 mg) and magnesium stearate (15 mg). The mixture is passed through a 60 mesh sieve and packed into a No. 1 gelatin capsule. A typical injectable preparation is produced by aseptically placing 250 mg of compounds of the invention into a vial, aseptically freeze-drying and sealing. For use, the contents of the vial are mixed with 2 mL of sterile physiological saline, to produce an injectable preparation.

The compounds of the invention can be administered to a mammal, especially a human in need of such treatment, prevention, elimination, alleviation or amelioration of a malcondition. Such mammals include also animals, both domestic animals, e.g. household pets, farm animals, and non-domestic animals such as wildlife.

The compounds of the invention are effective over a wide dosage range. For example, in the treatment of adult humans, dosages from about 0.05 to about 5000 mg, preferably from about 1 to about 2000 mg, and more preferably between about 2 and about 2000 mg per day can be used. A typical dosage is about 10 mg to about 1000 mg per day. In choosing a regimen for patients it can frequently be necessary to begin with a higher dosage and when the condition is under control to reduce the dosage. The exact dosage will depend upon the activity of the compound, mode of administration, on the therapy desired, form in which administered, the subject to be treated and the body weight of the subject to be treated, and the preference and experience of the physician or veterinarian in charge.

Generally, the compounds of the invention are dispensed in unit dosage form including from about 0.05 mg to about 1000 mg of active ingredient together with a pharmaceutically acceptable carrier per unit dosage.

Usually, dosage forms suitable for oral, nasal, pulmonal or transdermal administration include from about 125 µg to about 1250 mg, preferably from about 250 µg to about 500 mg, and more preferably from about 2.5 mg to about 250 mg, of the compounds admixed with a pharmaceutically acceptable carrier or diluent.

Dosage forms can be administered daily, or more than once a day, such as twice or thrice daily. Alternatively dosage forms can be administered less frequently than daily, such as every other day, or weekly, if found to be advisable by a prescribing physician.

In various embodiments, the invention is directed to a method of modulating a Kappa opioid receptor, comprising contacting the receptor with an effective amount or concentration of a compound of formula (I) of the invention. For example, the Kappa opioid receptor can be disposed within the living tissue of a human. More specifically, the human can be suffering from a dissociative disorder or pain.

In various embodiments, the invention provides a method of treatment of a dissociative disorder or pain in a patient in need thereof, comprising administering to the patient an effective amount or concentration of a compound of formula (I) the invention at a frequency and for a duration to provide a beneficial effect to the patient.

For example, in various embodiments, a method of providing neuroprotection to a patient comprising administering to the patient an effective amount or concentration of a compound of formula (I) of the invention, at a frequency and for a duration to provide a beneficial effect to the patient, is provided.

For example, in various embodiments, a method of modulating the immune system in a patient, comprising administering to the patient an effective amount or concentration of a compound of formula (I) of the invention, at a frequency and for a duration to provide a beneficial effect to the patient, is provided.

For example, in various embodiments, a method of inducing diuresis in a patient, comprising administering to the patient an effective amount or concentration of a compound of formula (I) of the invention, at a frequency and for a duration to provide a beneficial effect to the patient, is provided.

It is within ordinary skill to evaluate any compound disclosed and claimed herein for effectiveness in modulation of or binding to a Kappa opioid receptor and in the various cellular assays using the procedures described above or found in the scientific literature. Accordingly, the person of ordinary skill can prepare and evaluate any of the claimed compounds without undue experimentation.

Any compound found to be effective in modulation of or binding to a Kappa opioid receptor can likewise be tested in animal models and in human clinical studies using the skill and experience of the investigator to guide the selection of dosages and treatment regimens.

It is believed by the inventors herein, and based on information publicly available (see cited documents), that modulators of Kappa opioid receptors can be used for treatment of the following medical conditions:

Affective Disorders: Depression, Stress/Anxiety
a) Duman R S, Monteggia L M (2006) "A neurotrophic model for stress-related mood disorders" *Biol Psychiatry* 59(12): 1116-1127
b) Zhang H, Shi Y G, Woods J H, Watson S J, Ko M C (2007) "Central kappa-opioid receptor mediated antidepressant-like effects of nor Binaltorphimine: behavioral and BDNF mRNA expression studies" *Eur J Pharmacol* 570(1-3): 89-96 c) Land B B, Bruchas M R, Lemos J C, Xu M, Melief E J, Chavkin C (2008) "The dysphoric component of stress is encoded by activation of the dynorphin kappa-opioid system" *J Neurosci* 28(2):407-414 d) Filho C B, DelFabbro L, deGomes M G, Goes A T R, Souza L C, Boeira S P, Jesse C R (2013) "Kappa-opioid receptors mediate the antidepressant-like activity of hesperidin in the mouse forced swimming test" *Eur J Pharmacol* 698 (1-3): 286-291 e) Van't Veer A, Carlezon Jr W A (2013) "Role of kappa-opioid receptors in stress and anxiety-related behavior" *Psychopharmacology* doi 10.1007/s00213-013-3195-5

Addictive Disorders a) Blum K, Braverman E R, Holder J M, Lubar J F, Monastra V J, Miller D, Lubar J O, Chen T J, Comings D E (2000) "Reward deficiency syndrome: a biogenetic model for the diagnosis and treatment of impulsive, addictive, and compulsive behaviors" *Journal of psychoactive drugs* 32 Suppl: i-iv, 1-112 b) McLaughlin J P, Marton-Popovici M, Chavkin C. (2003) "Kappa opioid receptor antagonism and prodynophin gene disruption block stress-induced behavioral responses" *The Journal of Neuroscience* 23 (13): 5674-83 c) Hasebe K, Kawai K, Suzuki T, Kawamura K, Tanaka T, Narita M, Nagase H, Suzuki T (2004) "Possible pharmacotherapy of the opioid kappa receptor agonist for drug dependence" *Annals of the New York Academy of Sciences* 1025: 404-13 d) Beardsley P M, Howard J L, Shelton K L, Carroll F I (2005) "Differential effects of the novel kappa opioid receptor antagonist, JDTic, on reinstatement of cocaine-seeking induced by footshock stressors vs cocaine primes and its antidepressant-like effects in rats" *Psychopharmacology* (Berl.) 183 (1): 118-26 e) Mash, Deborah C. (2006) "Social defeat stress-induced behavioral responses are mediated by the endogenous kappa opioid system" *Neuropsychopharmacology* 31 (4): 787-94 f) Frankel P S, Alburges M E, Bush L, Hanson G R, Kish S J (2008) "Striatal and ventral pallidum dynorphin concentrations are markedly increased in human chronic cocaine users" *Neuropharmacology* 55 (1): 41-6 g) Redila V A, Chavkin C (2008) "Stress-induced reinstatement of cocaine seeking is mediated by the kappa opioid system" *Psychopharmacology* 200 (1): 59-70 h) Shippenberg T S (2009) "The dynorphin/kappa opioid receptor system: a new target for the treatment of addiction and affective disorders?" *Neuropsychopharmacology* 34: 247 i) Graziane N M, Polter A M, Briand L A, Pierce R C, Kauer J A (2013) "Kappa Opioid Receptors Regulate Stress-Induced Cocaine Seeking and Synaptic Plasticity" *Neuron* 77 (5): 942-954

Alcoholism a) Schank J R, Goldstein A L, Rowe K E, King C E, Marusich J A, Wiley J L, Carroll F I, Thorsell A, Heilig M (2012) "The kappa opioid receptor antagonist JDTic attenuates alcohol seeking and withdrawal anxiety" *Addiction Biology* 17(3): 634-647 b) Walker B M, Koob G F (2008) "Pharmacological Evidence for a Motivational Role of κ-Opioid Systems in Ethanol Dependence" *Neuropsychopharmacology* 33(3): 643-652

Walker B M, Zorrilla E P, Koob G F (2011) "Systemic κ-Opioid Receptor Antagonism by Nor-binaltorphimine Reduces Dependence-Induced Excessive Alcohol Self-Administration in Rats" *Addict Biol* 16(1): 116-119

Epilepsy a) De Sarro G B, De Sarro A (1993) "Anticonvulsant properties of non-competitive antagonists of the N-methyl-D-aspartate receptor in genetically epilepsy-prone rats: comparison with CPPene" *Neuropharmacology* 32(1):51-58 b) de Lanerolle N C, Williamson A, Meredith C et al (1997) "Dynorphin and the kappa 1 ligand [3H] U69, 593 binding in the human epileptogenic hippocampus" *Epilepsy Res* 28(3):189-205 c) Bausch S B, Esteb T M, Terman G W, Chavkin C (1998) "Administered and endogenously released kappa opioids decrease pilocarpine-induced seizures and seizure-induced histopathology" *J Pharmacol Exp Ther* 284(3): 1147-1155 d) Gambardella A, Manna I, Labate A, Chifari R, Serra P, La Russa A, LePiane E, Cittadella R, Andreoli V, Sasanelli F, Zappia M, Aguglia U, Quattrone A (2003) "Prodynorphin gene promoter polymorphism and temporal lobe epilepsy" *Epilepsia* 44(9):1255-1256 e). Loacker S, Sayyah M, Wittmann W, Herzog H, Schwarzer C (2007) "Endogenous dynorphin in epileptogenesis and epilepsy: anticonvulsant net effect via kappa opioid receptors" *Brain*130(pt 4): 1017-1028 f) Bortolato M, Solbrig M V (2007) "The price of seizure control: Dynorphins in interictal and postictal psychosis" *Psychiat Res* 151 (1-2): 139-143

Cognition Deficiencies a) Jiang H K, Owyang V V, Hong J S, Gallagher M (1989) "Elevated dynorphin in the hippocampal formation of aged rats: relation to cognitive impairment on a spatial learning task" *Proc Natl Acad Sci USA* 86(8): 2948-2951 b) Daumas S, Betourne A, Halley H, Wolfer D P, Lipp H, Lassalle J, Frances B (2007) "Transient activation of the CA3 Kappa opioid system in the dorsal hippocampus modulates complex memory processing in mice" *Neurobiol Learn Mem* 88(1):94-103 c) Carey A N, Lyons A M, Shay C F, Dunton O, McLaughlin J P (2009) "Endogenous k Opioid Activation Mediates Stress-Induced Deficits in Learning and Memory" *J Neurosci* 29 (13): 4293-4300 d) Nemeth C L, Paine T A, Rittiner J E, Beguin C, Carroll F I, Roth B L, Cohen B M, Carlezon W A Jr (2010) "Role of kappa-opioid receptors in the effects of salvinorin A and ketamine on attention in rats" Psychopharmacology 210 (2):263-274.

Schizophrenia

Tejeda H A, Shippenberg T S, Henriksson R (2012) "The dynorphin/k-opioid receptor system and its role in psychiatric disorders" Cell Mol Life Sci 69 (6): 857-896

Alzheimer's Disease a) Mathieu-Kia A M, Fan L Q, Kreek M J, Simon E J, Hiller J M (2001) "Mu-, delta- and kappa-opioid receptor populations are differentially altered in distinct areas of postmortem brains of Alzheimer's disease patients" *Brain Res* 893(1-2):121-134 b) Yakovleva T, Marinova Z, Kuzmin A, Seidah N G, Haroutunian V, Terenius L, Bakalkin G (2007) "Dysregulation of dynorphins in Alzheimer disease" *Neurobiol Aging* 28 (11):1700-1708

Pain (visceral pain, acute post-operative pain)

Arendt-Nielsen L, Olesen A E, Staahl C, Menzaghi F, Kell S, Wong G Y, Drewes A M (2009) "Analgesic efficacy of peripheral kappa-opioid receptor agonist CR665 compared to oxycodone in a multi-modal, multi-tissue experimental human pain model: selective effect on visceral pain" *Anesthesiology* 111(3): 616-624

Rivière PJ (2004) "Peripheral kappa-opioid agonists for visceral pain" *Brit J Pharmacol* 141 (8) 1331-1334.

Accordingly, the invention can provide a method of treating a condition in a human patient for which modulation of a kappa opioid receptor is medically indicated, comprising administering an effective amount of concentration of a compound of the invention at a frequency and for a duration to provide a beneficial effect to the patient, wherein the condition comprises one or more of an affective disorders comprising depression or stress/anxiety; an addictive disorder; alcoholism, epilepsy, a cognition deficiency, schizophrenia, Alzheimer's disease, or pain, e.g., visceral pain or acute post-operative pain.

Bioassay Procedures

The IC50 of each compound shown in Table was with respect to the kappa opioid receptor was determined.

The cell line for the OPRK1 antagonist assay stably expresses the following elements. The carboxy terminus of the OPRK1 receptor has a 7 amino acid linker, followed by the TEV protease cleavage site and a GAL4-VP16 fusion protein. The cell line also expresses a b-arrestin-2-TEV protease fusion protein and contains a reporter construct consisting of the UAS response element and the b-lactamase (bla) reporter gene. Upon activation of the receptor, g-protein receptor kinase (GRK) phosphorylates specific intracellular residues of OPKR1 and this induces recruitment of B-arrestin2-TEV protease fusion protein. The TEV protease recognizes and cleaves the TEV site, releasing the GAL4-VP16 fusion protein, which then translocates to the nucleus. The GAL4-V16 binds to the UAS element, driving expressing of the b-lactamase gene. B-lactamase expression is detected with the cell permeable, fluorescent substrate, CCF4-AM. This substrate consists of coumarin tethered to fluoroscein via a b-lactam ring. In the absence of b-lactamase, excitation of the dye with 405 nm light results in FRET from the coumarin to fluoroscein and emission of green (525 nm maximum) light. B-lactamase cleavage of the substrate separates the courmarin fluorophore from the fluorescein, and 405 nm excitation results in blue (460 nm maximum) emission. The assay is monitored by the blue/green emission ratio.

The antagonist assay is performed by seeding the cells into 384 well plates and incubating them 16-24 hours at 37° C. Test antagonist compounds are added and incubated for 30 minutes at 37° C. Next an EC80 challenge of U-50488 (OKRK1 agonist) is added and the samples are incubated for 4 hours at 37° C., followed by addition of CCF4-AM substrate. The plates are then incubated 2 hours at room temperature in the dark and the blue/green ratio determined on a fluorescent plate reader. See *J Biomol Screen* April 2009, vol. 14 no. 4, pp 381-394.

Bioassay Results

For the 118 compounds of table 1, 22 were found to have IC50 values of 10-100 nM, 46 had IC50 values of 100-1000 nM, 44 had IC50 values of 1000-10,000 nM, and 6 had IC50 values of greater than 10,000 nM While the invention has been described and exemplified in sufficient detail for those skilled in this art to make and use it, various alternatives, modifications, and improvements will be apparent to those skilled in the art without departing from the spirit and scope of the claims.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A compound of the following formula:

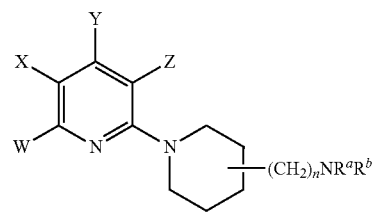

wherein
Y is H, halo, $(C_1-C_6)$alkyl, or $(C_3-C_9)$cycloalkyl;
Z is heteroaryl;
W and X taken together with the atoms to which they are bonded form a fused cycloalkyl or aryl, either of which can be mono- or independently multi-substituted with $(C_1-C_6)$alkyl, $(C_3-C_9)$cycloalkyl, halo, nitro, $NR^aR^b$, $N(R^a)C(=O)(C_1-C_6)$alkyl, $CO_2R$, or heteroaryl;
wherein any alkyl, cycloalkyl, aryl, or heteroaryl of W, X, Y, or Z, can be unsubstituted or can be mono- or independently multi-substituted with $(C_1-C_6)$alkyl, $(C_3-C_9)$cycloalkyl, halo, nitro, $NR^aR^b$, $N(R^a)C(=O)(C_1-C_6)$alkyl, $CO_2R$, or heteroaryl;
$R^a$ and $R^b$ are each independently H, alkyl, cycloalkyl, cycloalkylalkyl, heterocyclyl, or heterocyclylalkyl, wherein any alkyl, cycloalkyl, cycloalkylalkyl, heterocyclyl, or heterocyclylalkyl, is substituted with 0, 1, 2, 3, or 4 independently selected J, and wherein any heterocyclyl or cycloalkyl is mono-, bi-, or tri-cyclic;
or $R^a$ and $R^b$ together with the nitrogen atom to which they are bonded form a heterocyclyl ring substituted with 0, 1, 2, 3, or 4 independently selected J;
n=0, 1, or 2;
J is independently at each occurrence OR, $(C_1-C_6)$alkyl, hydroxy$(C_1-C_6)$alkyl, $(C_3-C_9)$cycloalkyl, $CO_2R$, or halo;
wherein each independently selected R is H, $(C_1-C_6)$alkyl, $(C_3-C_9)$cycloalkyl, $(C_6-C_{10})$aryl, or $(C_6-C_{10})$aryl$(C_1-C_6)$alkyl;
or any pharmaceutically acceptable salt thereof.

2. The compound of claim 1 wherein Y is H.

3. The compound of claim 1 wherein Y is $(C_1-C_6)$alkyl.

4. The compound of claim 1 wherein Y is halo.

5. The compound of claim 1 wherein Z is 3-methyl-1,2,4-oxadiazol-5-yl, 3-ethyl-1,2,4-oxadiazol-5-yl, or 3-cyclopropyl-1,2,4-oxadiazol-5-yl.

6. The compound of claim 1 wherein W and X taken together with the atoms to which they are bonded form a fused aryl which can be mono- or independently multi-substituted with $(C_1-C_6)$alkyl, $(C_3-C_9)$cycloalkyl, or halo.

7. The compound of claim 1 wherein n is 0 or 1; $R^a$ is ethyl, 2-pentyl, 4-methyl-2-pentyl, cyclopropyl, cyclobutyl, cyclopentyl, cyclohexyl, cycloheptyl, cyclooctyl, bicyclo[2.2.1]heptyl, bicyclo[2.2.2]octyl, bornyl, or adamantyl, any of which is substituted with 0, 1, 2, 3, or 4 J; and $R^b$ is H.

8. The compound of claim 1 wherein n is 0 or 1; and $R^a$ and $R^b$ together with the nitrogen atom to which they are bonded form a pyrrolidinyl, piperidinyl, azepinyl, morpholinyl, or thiomorpholinyl ring, any of which is substituted with 0, 1, 2, 3, or 4 J.

9. The compound of claim 1 wherein n is 0.

10. The compound of claim 1 wherein n is 0; $R^a$ is heterocyclyl; and $R^b$ is H.

11. The compound of claim 10 wherein W and X taken together with the atoms to which they are bonded form a fused aryl which can be mono- or independently multi-substituted with $(C_1-C_6)$alkyl or halo; Y is H or $(C_1-C_6)$alkyl; and Z is 3-methyl-1,2,4-oxadiazol-5-yl.

12. The compound of claim 1 wherein the compound is any of the following:

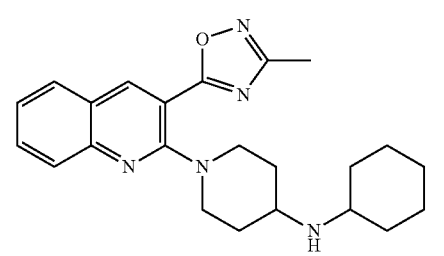
209

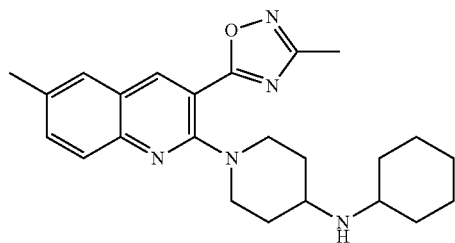
219

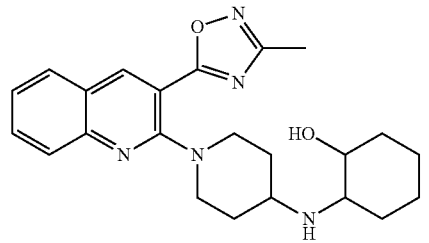
230

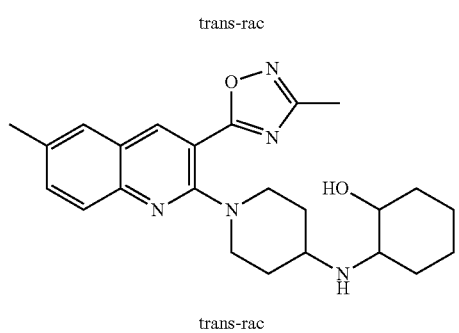
231
trans-rac

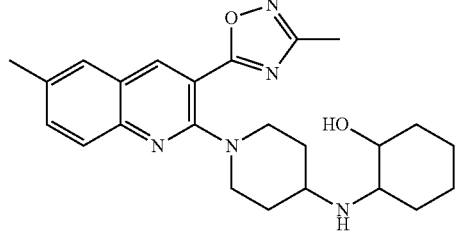
trans-rac

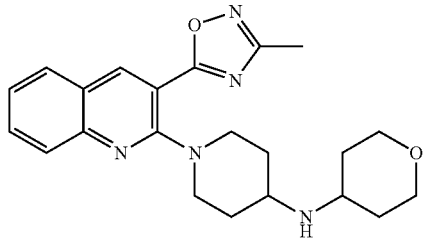
232

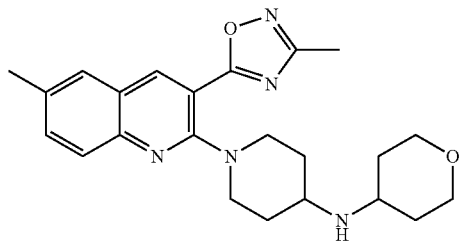
233

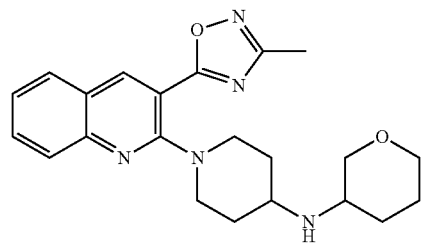
235

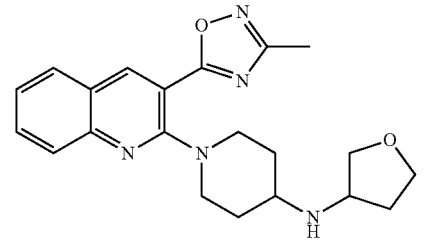
236

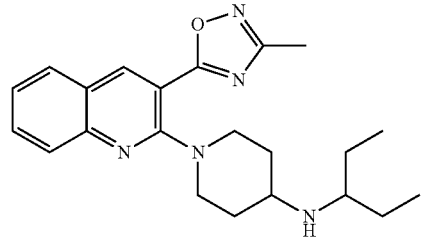
237

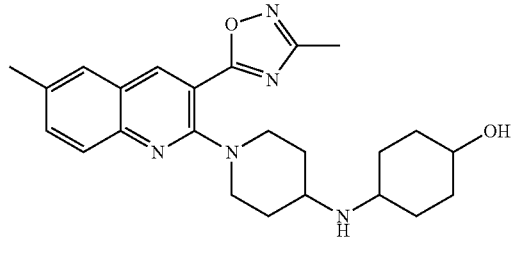
246
trans-rac

247 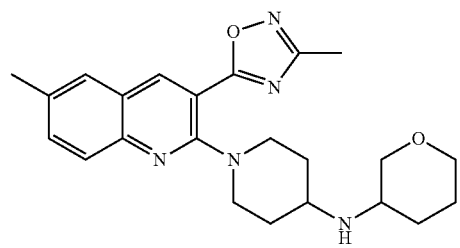
248 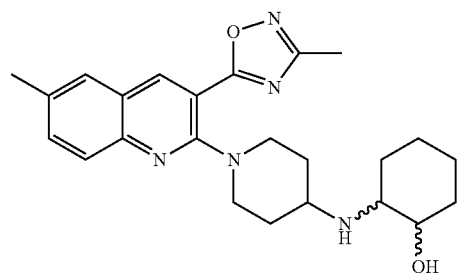
250 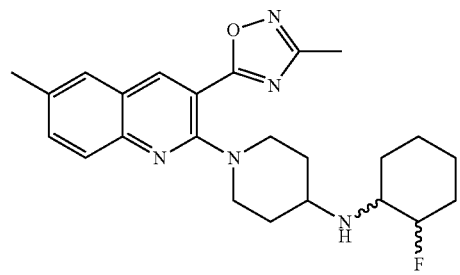
254 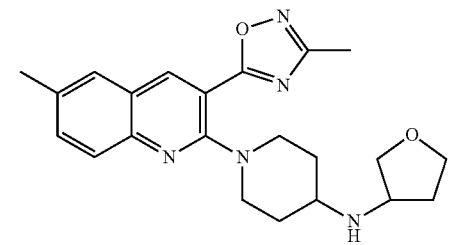
255 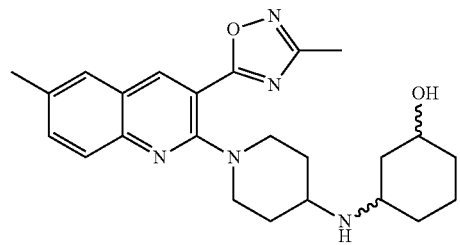
256 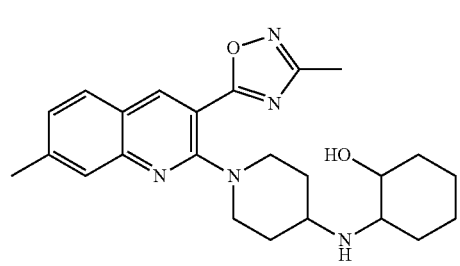
trans-rac
257 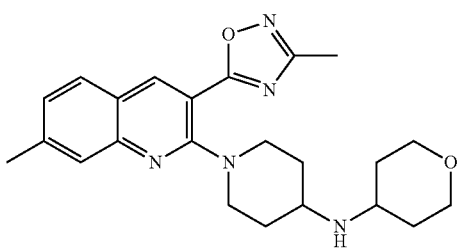
260 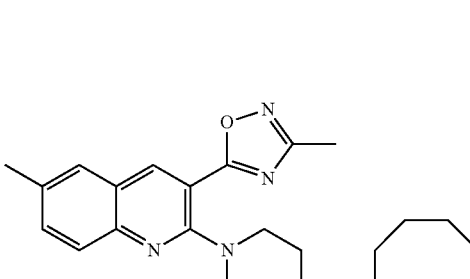
261 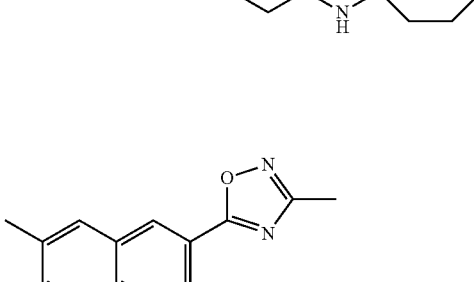
262 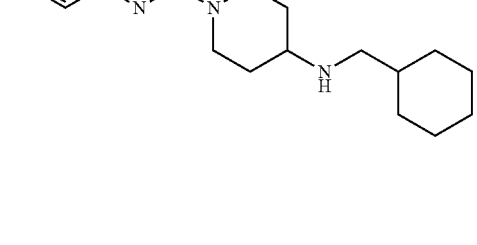
265 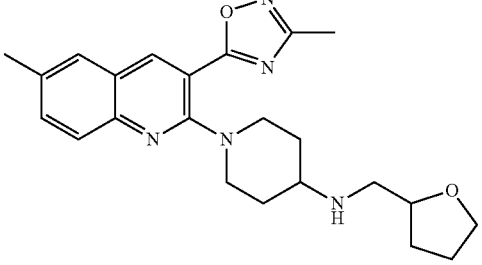
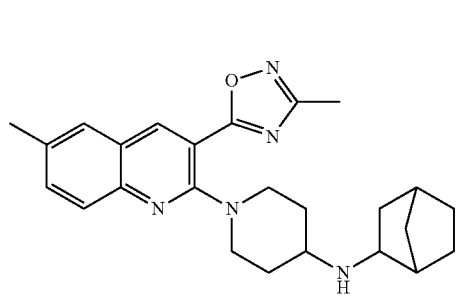

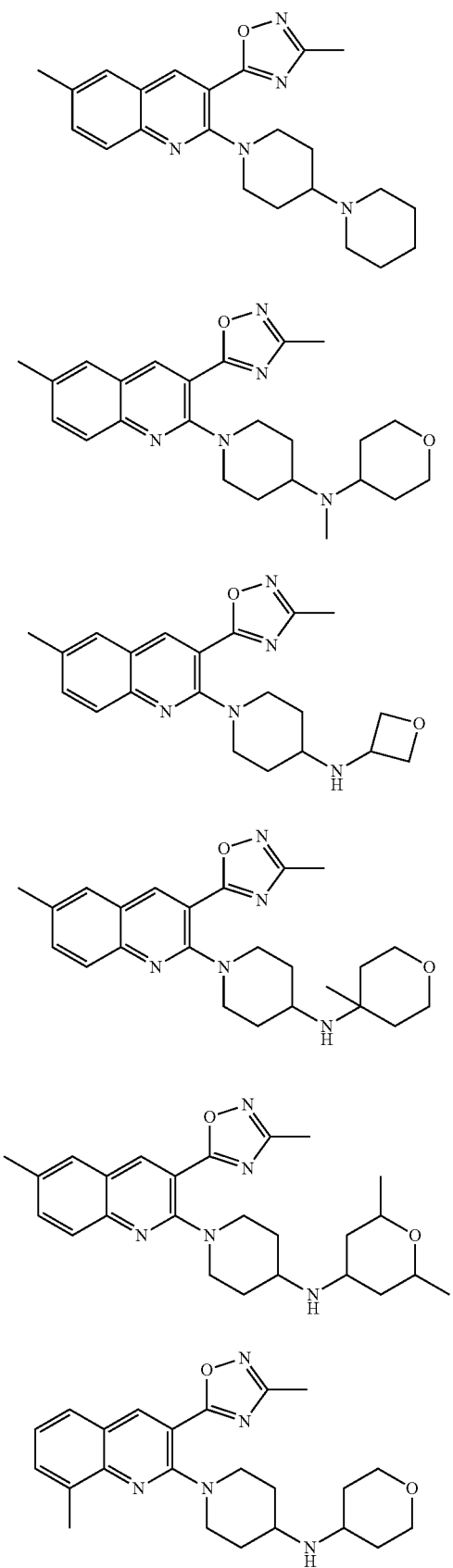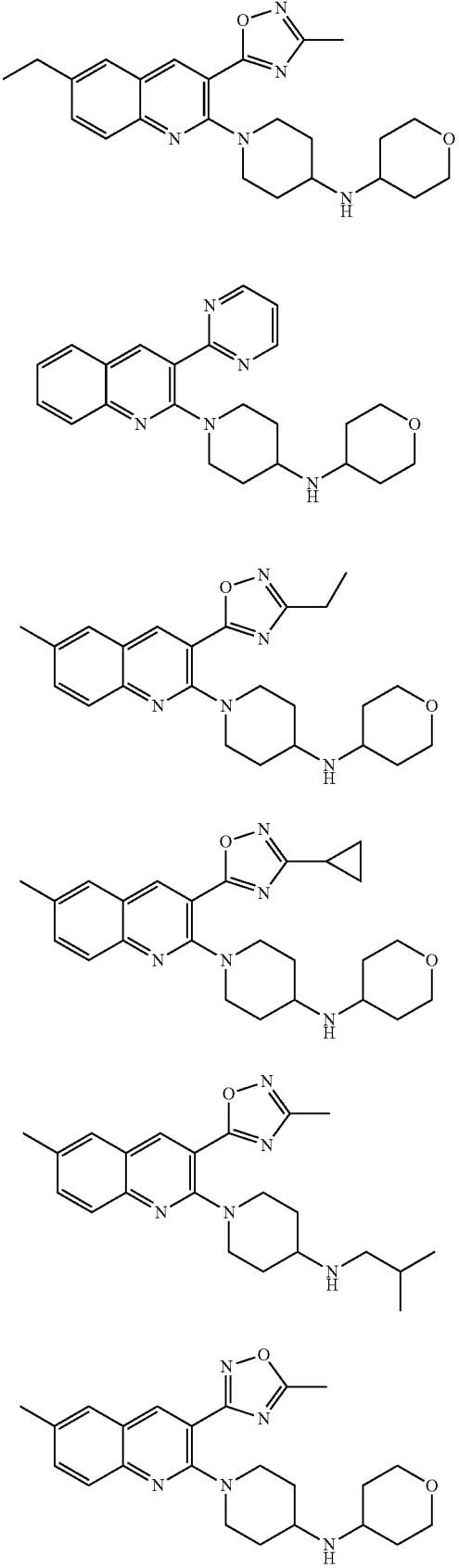

336
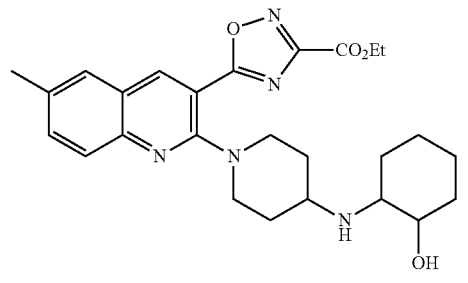
trans-rac
348
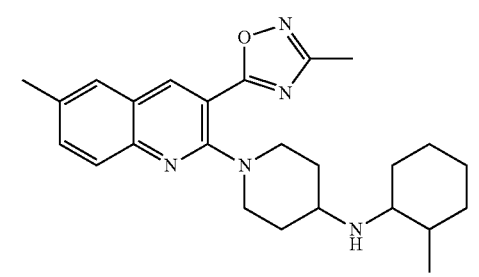
349
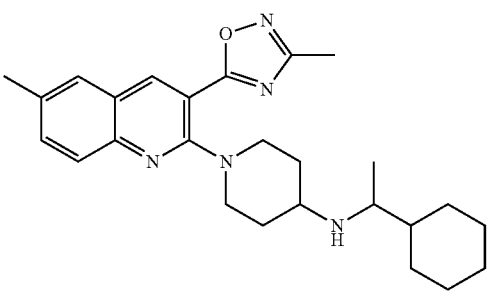
350
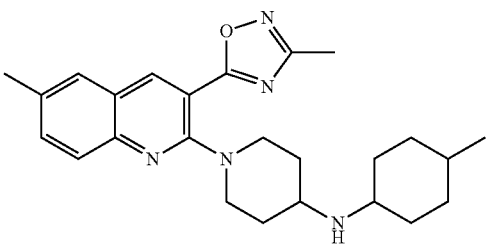
351
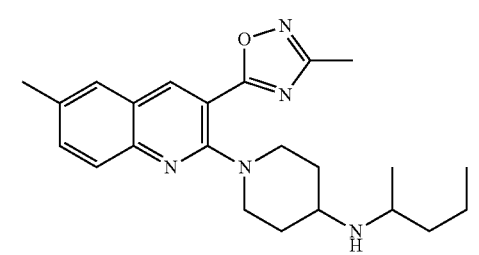
352
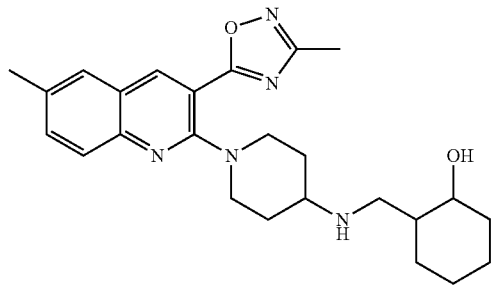
354
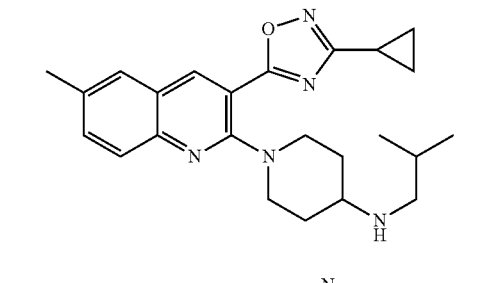
355
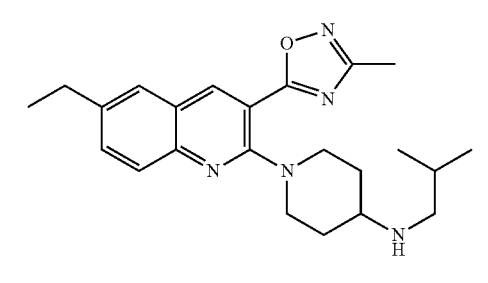
360
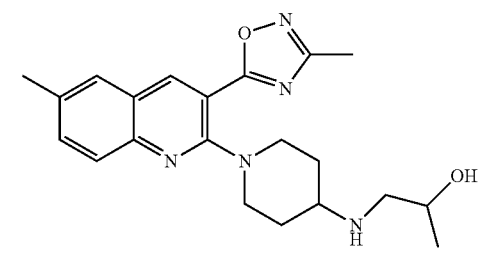
363
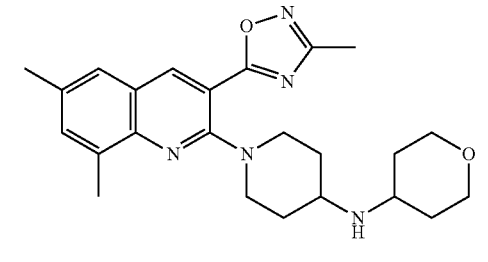
364
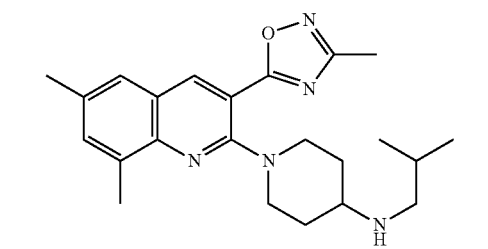

367 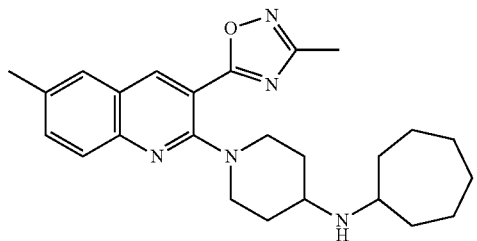
368 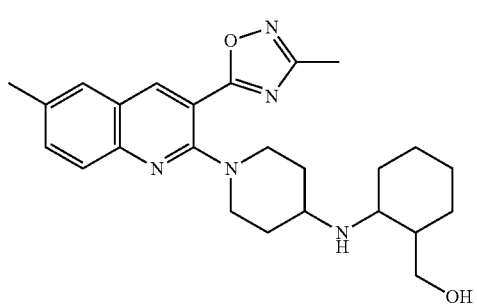
trans-rac
369 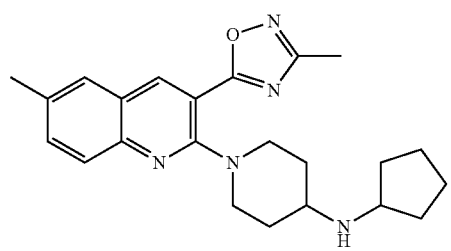
370 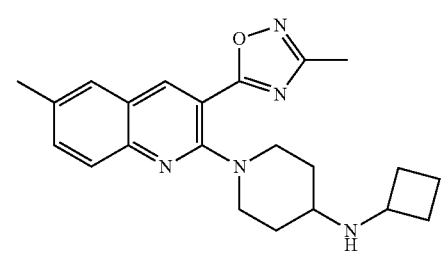
371 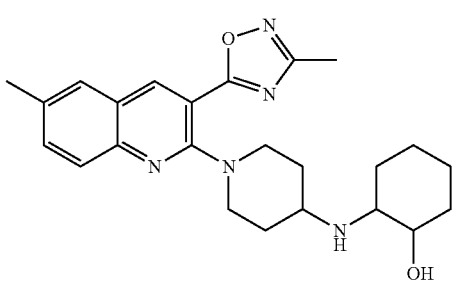
cis-rac
372 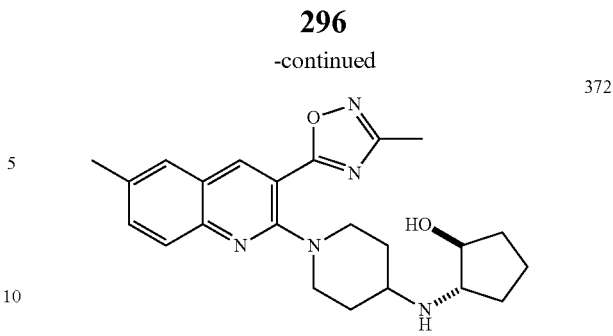
402 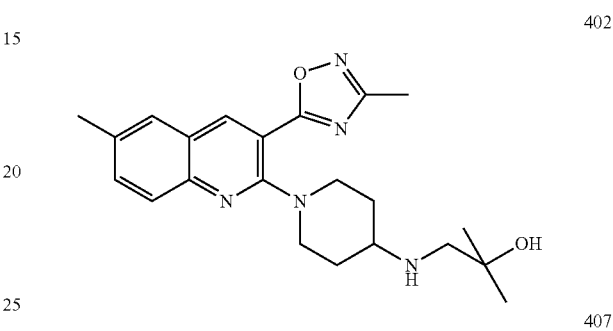
407 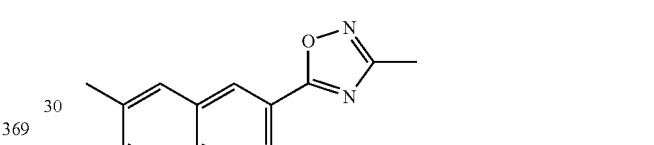
412 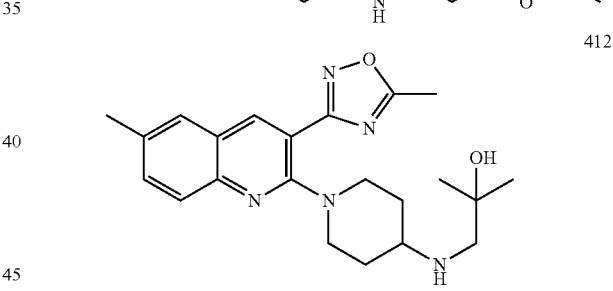
413 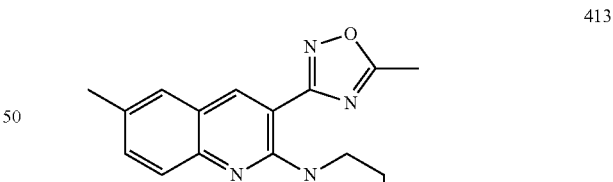
414 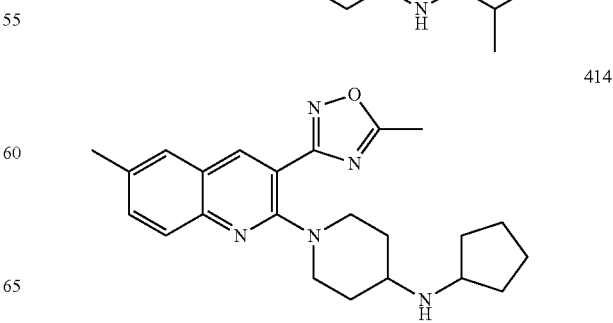

415
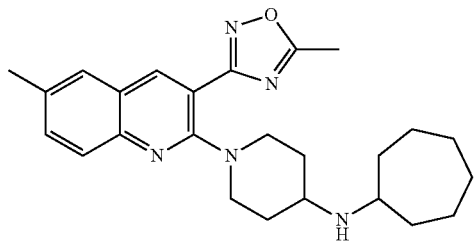
416
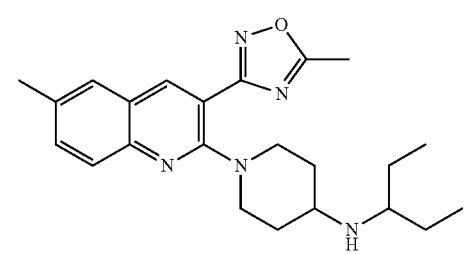
417
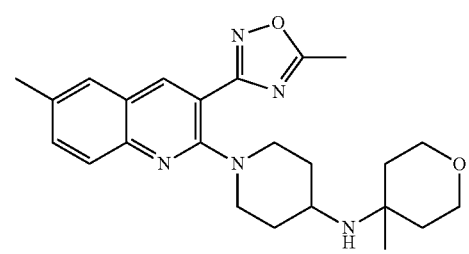
418
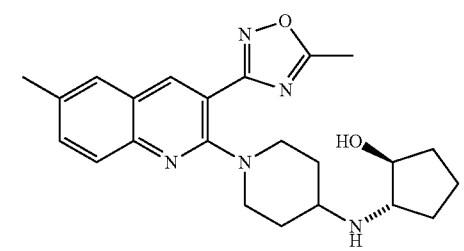
419
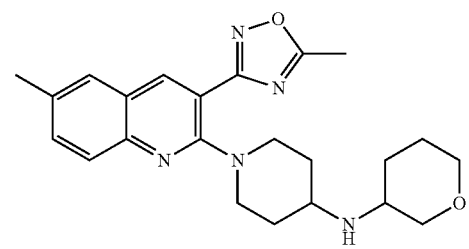
rac
421
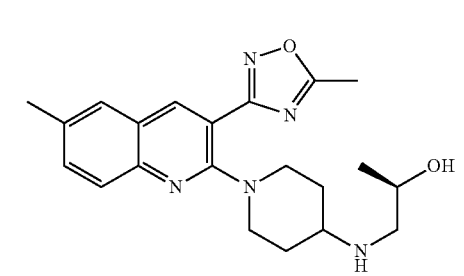
422
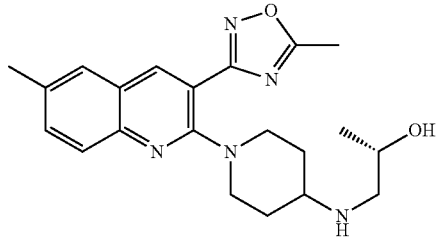
423
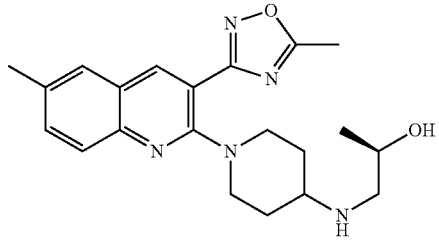
424
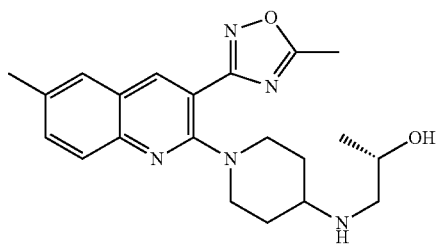
432
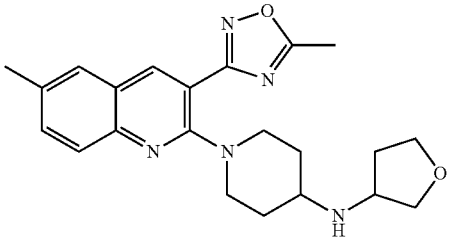
rac
433
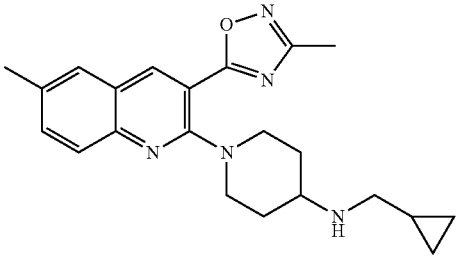
434
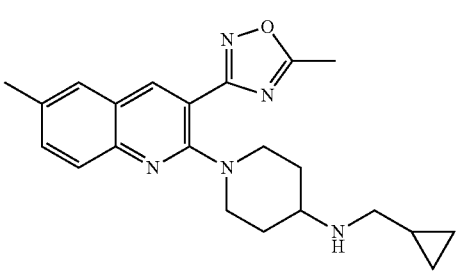

| 435 | 442 |
|---|---|
| 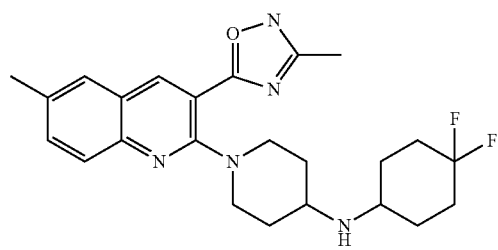 | 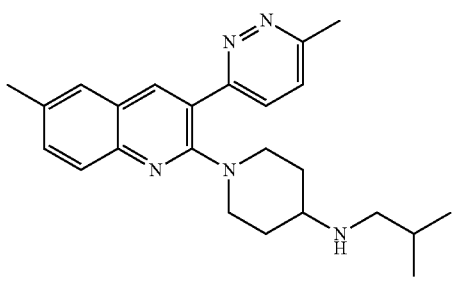 |
| 436 | 443 |
| 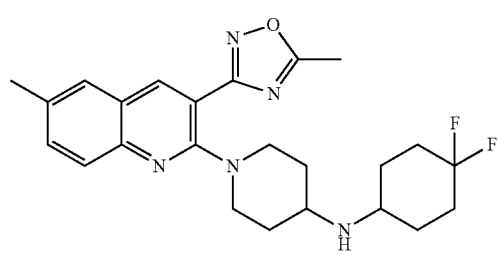 | 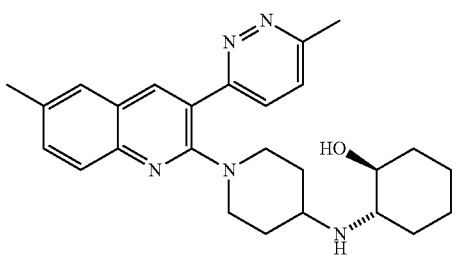 |
| 437 | 444 |
| 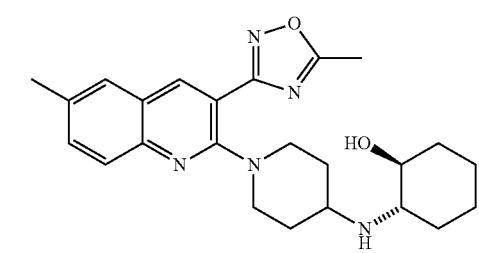 | 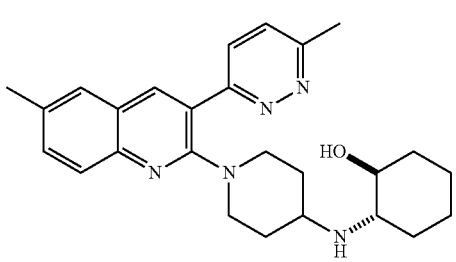 |
| 438 | 445 |
| 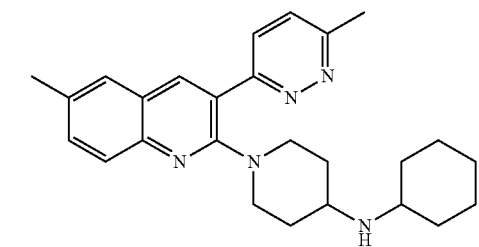 | 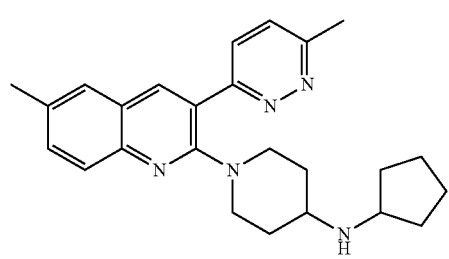 |
| 440 | 446 |
| 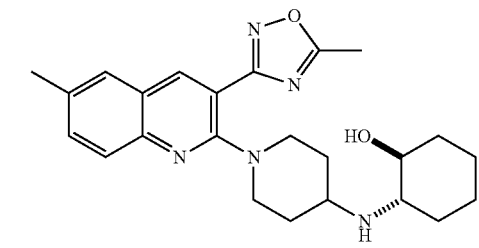 | 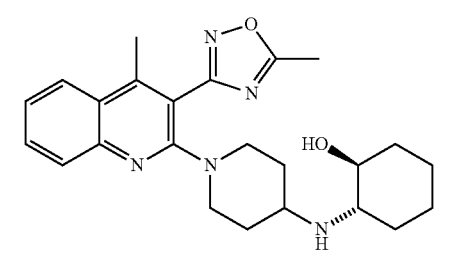 |
| 441 | 447 |
| 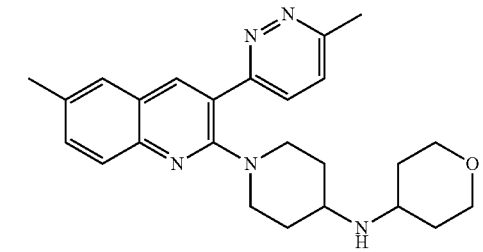 | 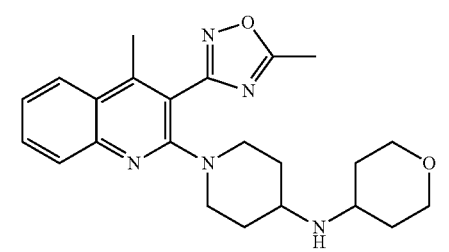 |

-continued

| 448 | 453 |
| 449 | 454 |
| 450 cis-rac | 455 |
| 451 cis-rac | 458 rac |
| 452 | 464 |
|  | 466 |

467
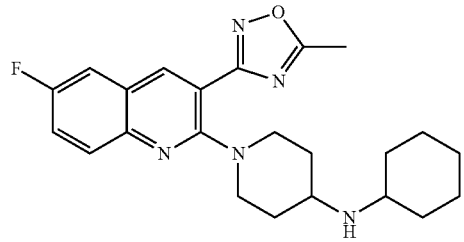
468
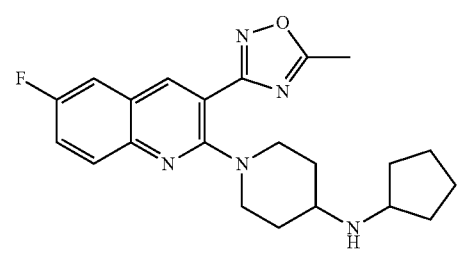
469
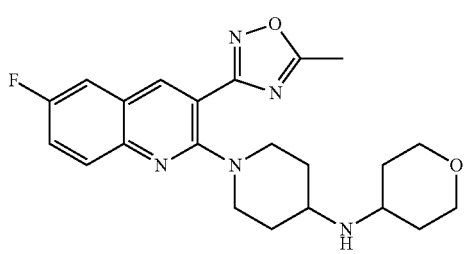
474
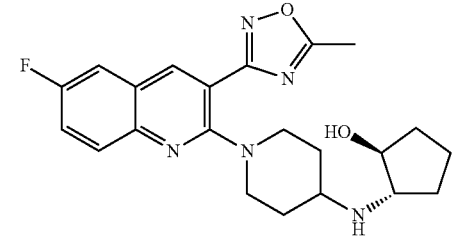
475
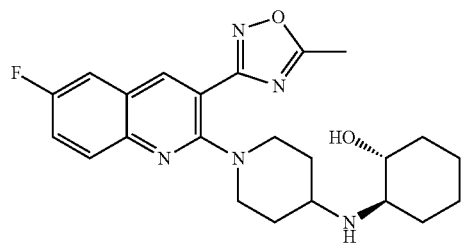
476
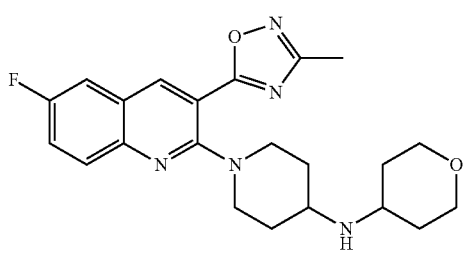
477
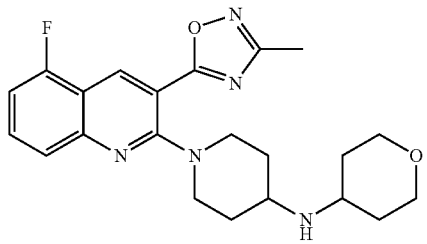
480
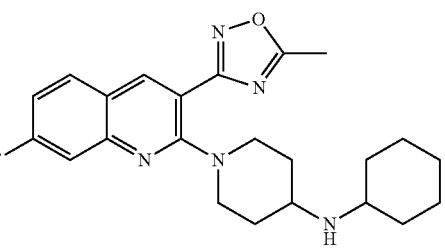
481
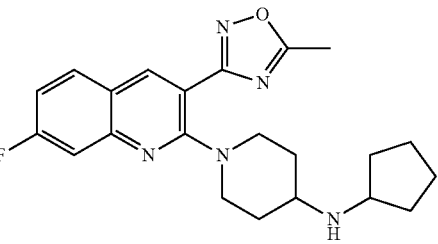
482
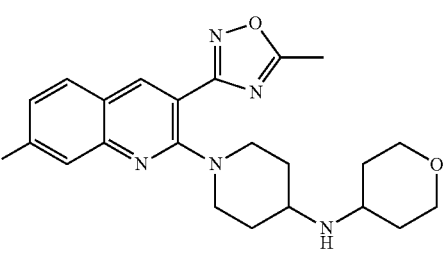
485
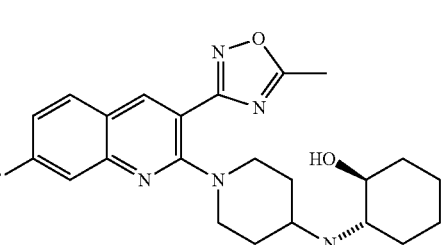
486
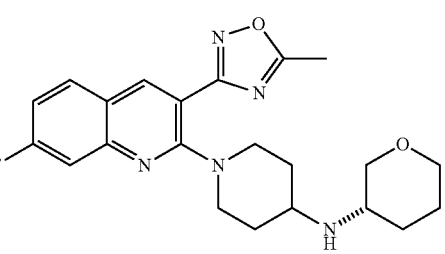

305
-continued
488
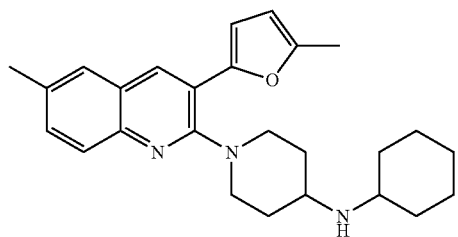
489
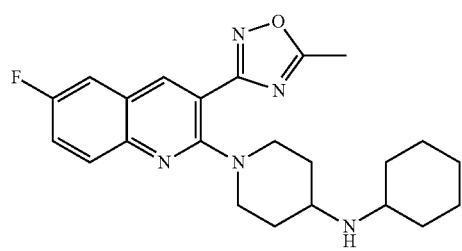
490
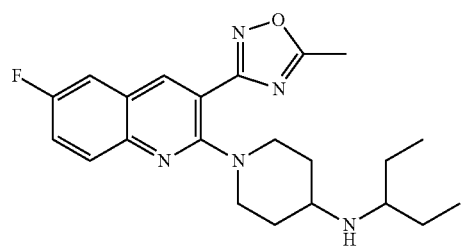
491
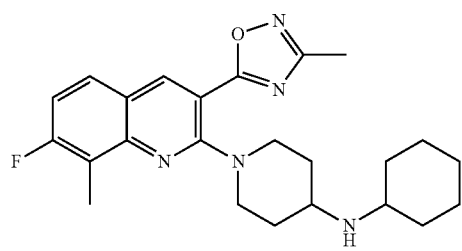
493
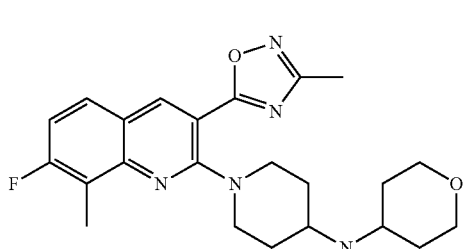
494
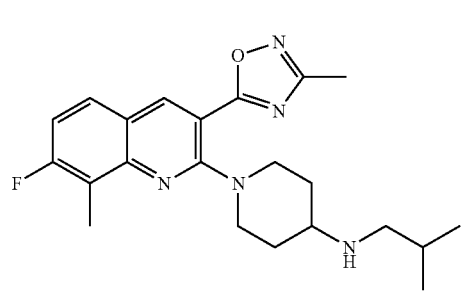
306
-continued
495
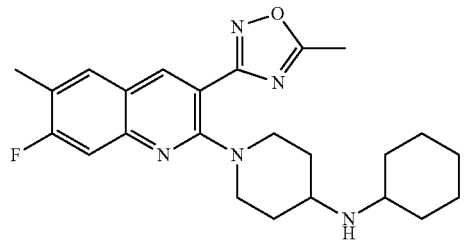
498
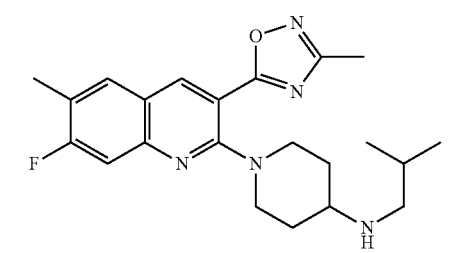
501
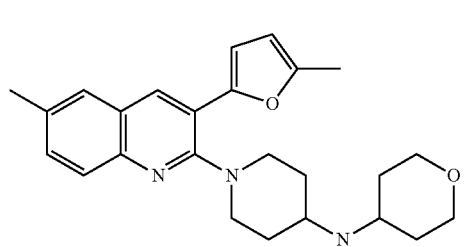
503
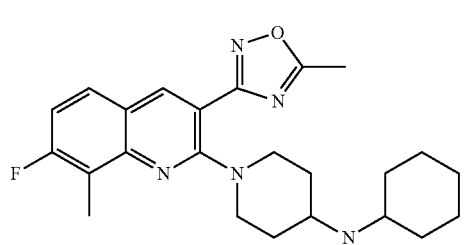
504
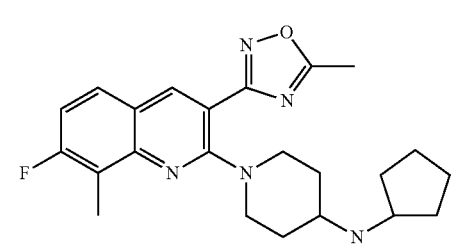
505
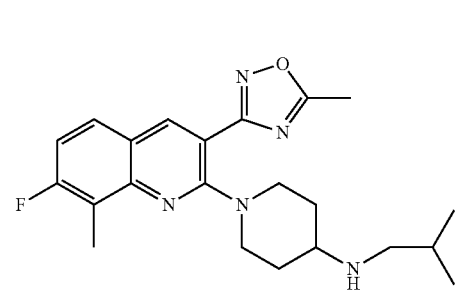

506
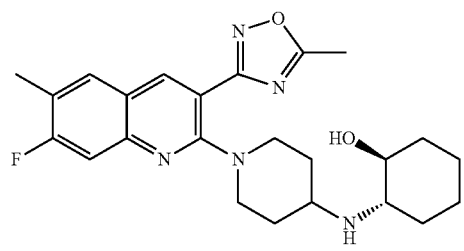
507
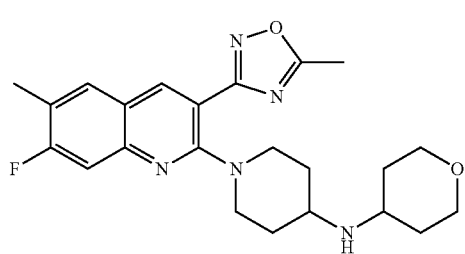
510
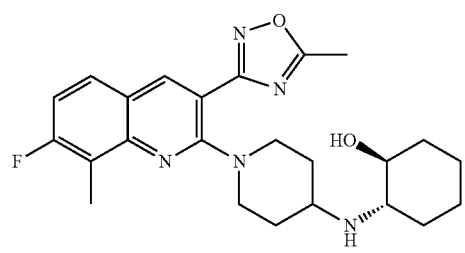
511
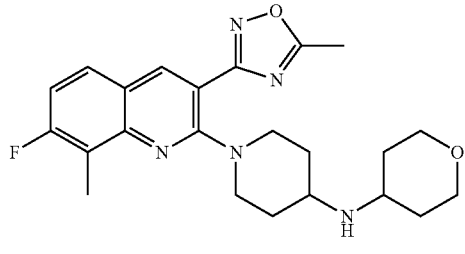
512
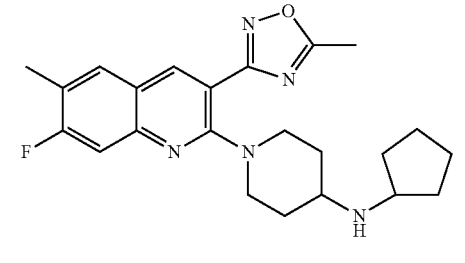
513
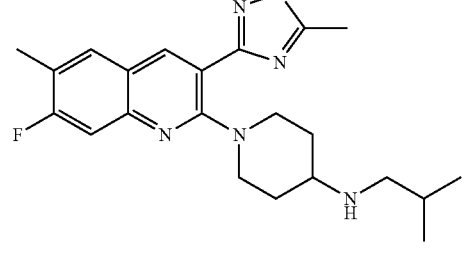
515
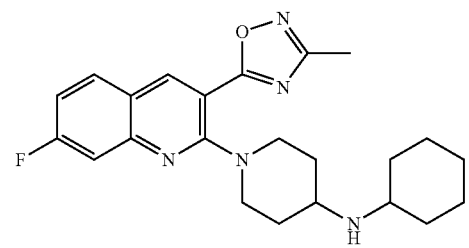
516
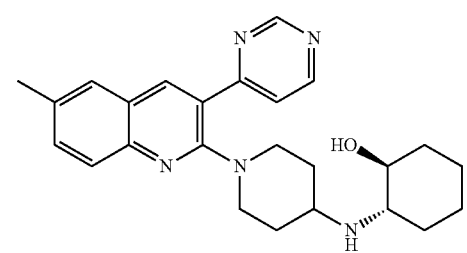
518
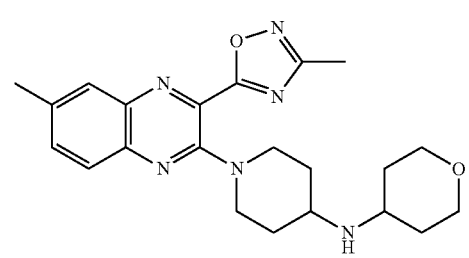
523
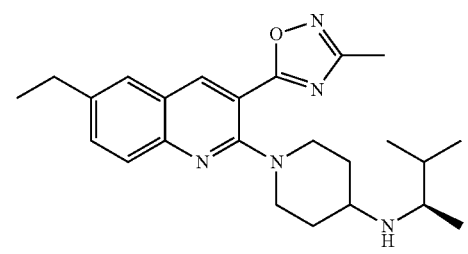
524
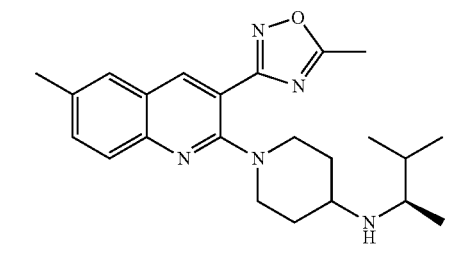
525
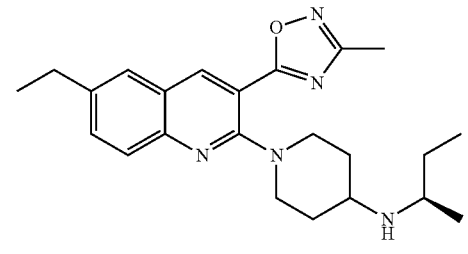

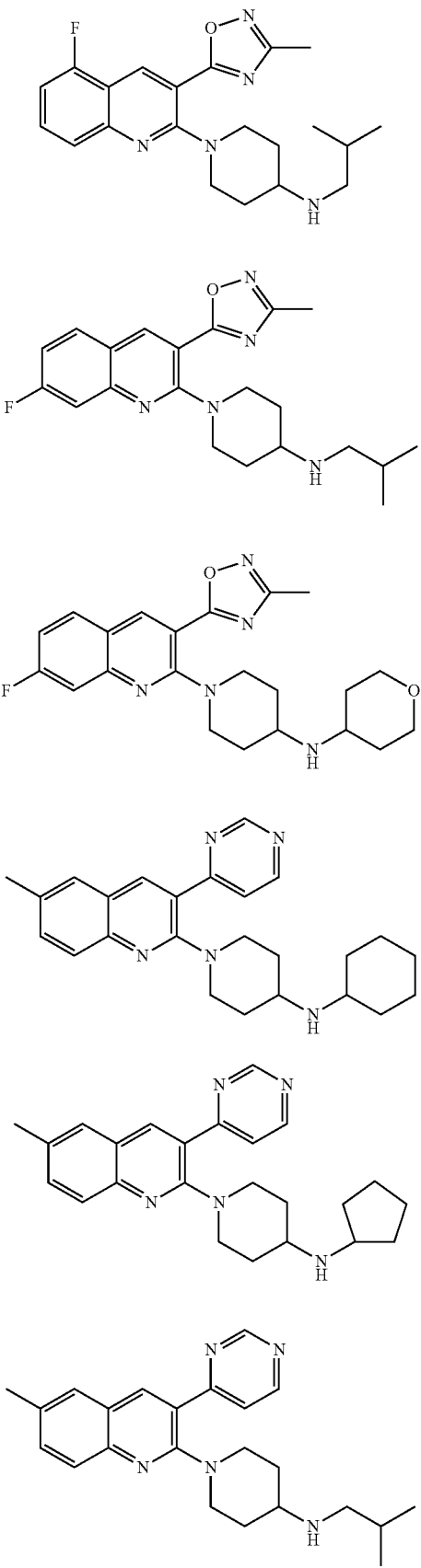

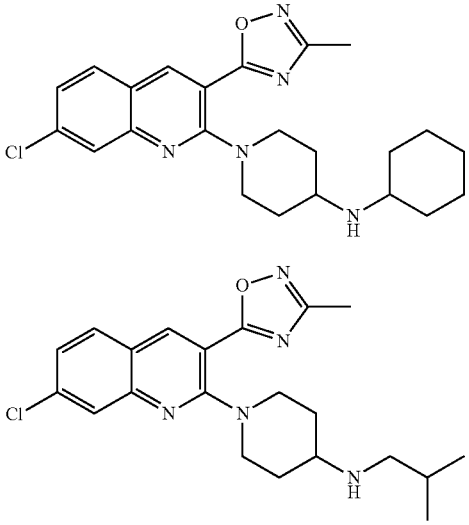

or any pharmaceutically acceptable salt thereof;
wherein rac denotes a racemic mixture, trans-rac denotes a ring trans compound as a racemic mixture, and cis-rac indicates a ring cis compound as a racemic mixture.

13. A pharmaceutical composition comprising a compound of any one of claims 1-12, or a pharmaceutically acceptable salt thereof, and a pharmaceutically acceptable excipient.

14. The compound of claim 10 wherein $R^a$ is tetrahydropyranyl.

15. The compound of claim 14 wherein $R^a$ is

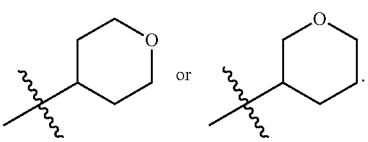 [SMILES: *C1CCOCC1 ; *C1CCCOC1]

16. The compound of claim 10 wherein $R^a$ is tetrahydrofuranyl.

17. The compound of claim 16 wherein $R^a$ is

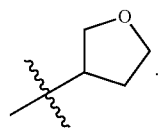 [SMILES: *C1CCOC1]

18. The compound of claim 10 wherein $R^a$ is oxetanyl.
19. The compound of claim 18 wherein $R^a$ is

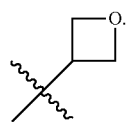

20. The compound of claim 9 wherein $R^a$ is cycloalkylalkyl and $R^b$ is H.

21. The compound of claim 20 wherein $R^a$ is

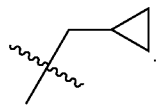

22. The compound of any one of claims 14-21 wherein Y is H; and W and X taken together with the atoms to which they are bonded form the fused aryl quinoline mono- or independently multi-substituted with $(C_1-C_6)$alkyl or halo.

23. The compound of claim 22 wherein Z is 3-methyl-1,2,4-oxadiazol-5-yl, 3-ethyl-1,2,4-oxadiazol-5-yl or 3-cyclopropyl-1,2,4-oxadiazol-5-yl.

24. The compound of any one of claims 14-21 wherein Y is methyl; and W and X taken together with the atoms to which they are bonded form the fused aryl quinoline mono- or independently multi-substituted with $(C_1-C_6)$alkyl or halo.

25. The compound wherein 24 is 3-methyl-1,2,4-oxadiazol-5-yl, 3-ethyl-1,2,4-oxadiazol-5-yl or 3-cyclopropyl-1,2,4-oxadiazol-5-yl.

\* \* \* \* \*

UNITED STATES PATENT AND TRADEMARK OFFICE
CERTIFICATE OF CORRECTION

PATENT NO. : 9,682,966 B2
APPLICATION NO. : 14/421932
DATED : June 20, 2017
INVENTOR(S) : Edward Roberts et al.

It is certified that error appears in the above-identified patent and that said Letters Patent is hereby corrected as shown below:

In the Claims

Column 311, Lines 21-23:
"25. The compound of claim wherein 24 is 3-methyl-1,2,4-oxadiazol-5-yl, 3-ethyl-1,2,4-oxadiazol-5-yl or 3-cyclopropyl-1,2,4-oxadiazol-5-yl." should read, --25. The compound of claim 24 wherein Z is 3-methyl-1,2,4-oxadiazol-5-yl, 3-ethyl-1,2,4-oxadiazol-5-yl or 3-cyclopropyl-1,2,4-oxadiazol-5-yl.--.

Signed and Sealed this
Eleventh Day of December, 2018

Andrei Iancu
*Director of the United States Patent and Trademark Office*